United States Patent
Hung et al.

(10) Patent No.: US 8,304,526 B2
(45) Date of Patent: Nov. 6, 2012

(54) ANTITUMOR EFFECT OF MUTANT BIK

(75) Inventors: Mien-Chie Hung, Houston, TX (US);
Yan Li, Houston, TX (US); Yong Wen, Burlingame, CA (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 12/829,651

(22) Filed: Jul. 2, 2010

(65) Prior Publication Data

US 2011/0020431 A1  Jan. 27, 2011

Related U.S. Application Data

(60) Division of application No. 12/180,730, filed on Jul. 28, 2008, now abandoned, which is a continuation of application No. 10/816,698, filed on Apr. 2, 2004, now abandoned.

(60) Provisional application No. 60/459,901, filed on Apr. 2, 2003.

(51) Int. Cl.
*C07H 21/04* (2006.01)

(52) U.S. Cl. ..................................................... 536/23.5
(58) Field of Classification Search ....................... None
See application file for complete search history.

(56) References Cited

U.S. PATENT DOCUMENTS 6,190,912 B1 * 2/2001 Alnemri ........................ 435/375

OTHER PUBLICATIONS

Azar et al (Apoptosis, 2000, 5:531-542).*
Verma et al, J Biological Chemistry, 2001, 7:4671-4676.*

* cited by examiner

*Primary Examiner* — Laura B Goddard
(74) *Attorney, Agent, or Firm* — Parker Highlander PLLC

(57) ABSTRACT

The present invention regards mutant forms of Bik that comprise anti-cell proliferation and/or pro-apoptotic activities. In particular embodiments, the Bik polypeptides comprise a substitution at Thr33 and Ser35 and, in some embodiments, phosphorylation at these sites is inhibited. In more particular embodiments, these forms are useful for cancer therapy, particularly when administered in combination with liposomes. In embodiments wherein a mutant Bik polynucleotide is administered for cancer therapy, the polynucleotide may be regulated in a tissue-specific manner.

4 Claims, 17 Drawing Sheets

Heart, 200x    Tumor, 400x

SEQUENCE LISTING

```
<160> NUMBER OF SEQ ID NOS: 38

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 1
ggcatgactg acgatgaaga ggacctg                                               27

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 2
gttcttggca tggatgactc tgaacagg                                              28

<210> SEQ ID NO 3
<211> LENGTH: 160
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 3

Met Ser Glu Val Arg Pro Leu Ser Arg Asp Ile Leu Met Glu Thr Leu
  1               5                  10                  15

Leu Tyr Glu Gln Leu Leu Glu Pro Pro Thr Met Glu Val Leu Gly Met
             20                  25                  30

Thr Asp Ser Glu Glu Asp Leu Asp Pro Met Glu Asp Phe Asp Ser Leu
         35                  40                  45

Glu Cys Met Glu Gly Ser Asp Ala Leu Ala Leu Arg Leu Ala Cys Ile
     50                  55                  60

Gly Asp Glu Met Asp Val Ser Leu Arg Ala Pro Arg Leu Ala Gln Leu
 65                  70                  75                  80

Ser Glu Val Ala Met His Ser Leu Gly Leu Ala Phe Ile Tyr Asp Gln
                 85                  90                  95

Thr Glu Asp Ile Arg Asp Val Leu Arg Ser Phe Met Asp Gly Phe Thr
                100                 105                 110
```

```
Thr Leu Lys Glu Asn Ile Met Arg Phe Trp Arg Ser Pro Asn Pro Gly
        115                 120                 125

Ser Trp Val Ser Cys Glu Gln Val Leu Leu Ala Leu Leu Leu Leu Leu
130                 135                 140

Ala Leu Leu Leu Pro Leu Leu Ser Gly Gly Leu His Leu Leu Leu Lys
145                 150                 155                 160

<210> SEQ ID NO 4
<211> LENGTH: 150
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Met Ser Glu Ala Arg Leu Met Ala Arg Asp Val Ile Lys Thr Val Pro
1               5                   10                  15

His Asp Gln Val Pro Gln Pro Val Ala Ser Glu Thr Pro Ser Met
            20                  25                  30

Lys Glu Pro Val Arg Asp Val Asp Leu Met Glu Cys Val Glu Gly Arg
        35                  40                  45

Asn Gln Val Ala Leu Arg Leu Ala Cys Ile Gly Asp Glu Met Asp Leu
    50                  55                  60

Cys Leu Arg Ser Pro Arg Leu Val Gln Leu Pro Gly Ile Ala Ile His
65                  70                  75                  80

Arg Leu Ala Val Thr Tyr Ser Arg Thr Gly Val Arg Gly Ile Phe Arg
                85                  90                  95

Ser Leu Ile Arg Ser Leu Thr Asn Leu Arg Glu Asn Ile Trp Ser Trp
            100                 105                 110

Arg Val Leu Thr Pro Gly Ala Trp Val Ser Pro Asp Gln Asp Pro Gly
        115                 120                 125

Gln Leu Phe Pro Met Val Leu Val Phe Leu Leu Leu Gly Gly Ala
    130                 135                 140

Trp Tyr Leu Gln Leu Gln
145                 150

<210> SEQ ID NO 5
<211> LENGTH: 21560
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
tgatcagcat attgtcttgg gattttgcaa agtaaataag tactgtattt gcacccactc      60
tgcccttgaa tcatccagtg tccccaaacg gtccttcttt ctccatcttt tctgctaatg     120
tttactgaac atctcctaca tacctggcac tgtgcctcca gccttaagac ccctctgcaa     180
gcatctcaca tatatcaggt ctttcggacc catgagaccc cgtgtcattg ctttacctcc     240
ctgagtctca atttttcat ctgcaaaatg cattcagagg gaagccccca ttatgaaggg      300
ttccctactc ctgactgtaa ggcactctgt ggctgttagc cacagtcagg gcgagctgct     360
ttgtaggggt tgatgtagtt tggaggccct agaagaaaag actacagggc cgggagtggt     420
ggctcacgcc tgtaatccca gcactttggg agcccgaggc ggtggatca cctggtgtca     480 ggagttcaag accagcctgg ccaatatggc aaaaccccgt ctctactaaa aatacaaaaa     540
ctagccgggc atggtggcac acgcctgtaa tccagctact agggggggctg aggcgggagg     600
```

```
attgcttcaa cctgggagac agacgttgca gtgagccaag attgtgccac tgcactccag    660
cctgggcaac agggctagac tctgtctcaa aaaaacaaaa acaaaaacaa acaaaaaaac    720
cccacaaaag caaagaaggt ccagagcccg gaaggcggga ggggctctga agactttatc    780
acactttacc tcctctgttc ctcccaacag cccagctctt ggtaggtgct gttgtccatt    840
tcacagatga gaacattgaa ggggaagtaa ttaccctaga ggtgggaaga acagagtgag    900
ggtacccaac aggtagcaaa cgacagagct gggggagggg aaccctgtc cctgcccctc      960 ccctaatctc tgaggggatc aagacagaag taaacaagct ttgccgtgcc caggacaatt    1020
gttactttgt tattccagga gcgctctgcc ttctcccacc cccaatatac cccagggctg    1080
gagttaggtc ctacccatcc ccgcgtagca ggctgcccac ccgcccaccc cgcctggaag    1140
ctttctgatt tctctgttcg ccccgccagg cgctgtgggg tccgtctcac caggtctgca    1200
cgtgagcccc ctgcccccaa tcctcccag tccgcccgc ctctcgcgga cccggagccc      1260
cgacgggagg gggaaggcag tgggtgtgtc atgcagctgg aaggctgcgg acgggcggca    1320
gtggaggggc agcccctgg cttcgggtat ggatcactgg atgctgctgc taaccaaatg      1380
tgaacctcgg ttttcatatt tgtgaaatag gcttaaaaac acctaaatcc caaagctgcc    1440
agcctaagga gcacacgtct ttgaacgctg gcttcacgct gtcatttaag tcatttcgtc    1500
ctcttggagc ctcggtttcc acgtgggtaa aatgatcgtg aaaaaaagca ccgaggagta    1560
ctttgagctc gaacggaggc catccgtgta aagggccaga ttctgtcaat ggatcgatcc    1620
ccccgatatt gatggaaacc cctgagtgca cgcccgtgct gggcgcaggg gaaacagcga    1680
cgcacgggac aaaacaagct tgcagaacag caggggcag agaggctgta aacaagccaa      1740
cgggctgcac ttgtagcggt tctgttgcca atgccattca gacccagtc cgggattccg      1800 cgctcggggt gcgagaggcc gctcccgggg aggggcggga cccgggcggg gcgggagggg    1860
cggggcgccc gggcctatta ggtcccgcgc cggcagccgg gccgcagaca cgaagcctcc    1920
cgggtggctt acagacgctg ccagcatcgc cgccgccagg tgagtgcccc cgaccctgct    1980
gccgcccgct gctccgccca gctcgagccc ggcggttagc gcccaggccg cggcccgggt    2040
gccgagcggc tggaagtgtg gggagccgtg cccaggtttt accgctccag caagtcgctg    2100
gcggggcgac gtctcgggac tccggctccg aaacgtaccc tctctgtccg gggctccagg    2160
tccccgacgg gcgatcgtgc caggcgcggc ccctgcgggc ctcagtctcc gcgcctgtgc    2220
aatggggtgg tccctctgcg tctcgccgcg acggctggac gccccatcgc cgccgcacag    2280
tcctccagtg cggcttccgg gcacccggct ccgaactctg gggtcgtgcg gacccggcca    2340
gaccgtagcg cggcaacgcc agcccacggc cgcggccgca cagccccggt gcccttaaaa    2400
gagggaagat ggcgtcgtgc ccggtgccgc cgggaccggc tccggaggc gctgcgcacc      2460 tgaggaaggg ccgaggaaag gcttcgtaac gggacgccca gaaagtccgg aacaggaacg    2520
tgcacacgga gcggcgcgca gccgcccgcc ctcgcttgcc cacgcgccct gcacaggtgc    2580
gccccagact gggcggggac tagagcccgg ctggggcatg cgaccttgtt tggtaaattg    2640
gaggtgcgcc cctgcgggtg acccgcgagg gggccccccg cctgcgggc gcggtcacga      2700 caaggcttgt ggggttcgga gctggtcgtc gtctgggctc tggcctccta aatgcgatcg    2760
ctttcaagcc cttcattgtc aattttgcta gaatgagcca ctcgtggggt aggacgtggt    2820
tgttgatgtt actgttgtag ctcttactat tgtaacattt tgttgctgt tttaacgcag      2880 tgtttactgt ggtctgggag cccgagcttc cagggagca ttggtgtcag cctcatgtcc      2940
ccgcattagg aggagcgcag tctggtgggc actagcgccg ggaagttctt aacatctgtc    3000
```

```
tgcccctggg agcaggaggc ctcatcttcc aggtggagaa acagagattt cagtcccagg    3060
aggcacagaa atgccagggt tgtctagcta gaagccaagg gcccttatg gaacccaagc     3120 caaaacctct ttccactctc cagccctgtg gcctcggaag ggccactcca tctctctgaa    3180
cctcagtttg ttctgttcac tctgcaaaat gtatccctga ggtttctggc caggtgaaag    3240
cccctctcaa gttagtagcc tccctggagt taagactcac cccgatttct acttaatttg    3300
ggcacgcctt tggaataagt tctcaggaat ggcacagttt gggtgttttt tgtttctttt    3360 tgttttttt tgaaacagag cttcgctctt gttgcccagg ctggagtgca atggcgccgt     3420
ctcggctaac tgcaacctcg gcctcctggg ttcaaacggt tctcctgcct cagcctccta    3480
gtagctggga ttacaggcgc ctaccacgag gcccagctaa ttttttgtat ttttagtaga    3540
gatgggtttt caccatgttg gccaagctag tctcgaactc ctgacctcag gcgatccacc    3600
cgcctcagcc tcccaaagtg ctgggattac aggtgtgacc caccccgccc ggcttgagtg    3660
tttaaatact cctgcctcag cctcccaagg tgctgggatt acagacgtga gcccctatgc    3720
ctggcccttt ttttttttt aattgtctta aggatgttaa gactaagatt ctcacacatt     3780
tgactcgtgc ctgtaatcct agcactttgg gaggctgagg caggaggatt gcttgagctc    3840
aggagactag actgggctag accagactgg gtaacatggt aaaaccctgt ctctaccaaa    3900
aatacaaaaa attaaccggg catggtggca tgtgcctctg gtcctagcta cgcaggaggc    3960
tgagttcaga ggcctacctg agcttggagg ggttgaggct gcagtgaacc ctgatcatgc    4020
cactgcactc tagcctggga gacagagtga gaccctgtct caaaaaagg agcattaggc     4080 tgggcatggt ggctcacatt tgtaatccta gcactttggg aggccgaggg agatggatca    4140
cctgaggtca ggagttgtga gacgagcctg gccaacatgg caaaaccagt ctcttttaaa    4200
aatgcaaaaa ttagccggtc gtggtggcgt gtgtctgtaa tcccagctac ttgggaggct    4260
gaggcaggag aactgcttga atctgggagg cagaggttgc actgagcgga gatcacacca    4320
tggcactcca gcctgggcca catagggaga ctctctgtca aagaaaatt taaaaaagca     4380 tcaaatggta gatccccagt gtctgttaca gcttgggtac tctatggctg gatagagagg    4440
ctgcatacat gttagttatt gtaagtttgt ttgtttttt gagacggagt ttcgctcttg     4500
ttgcccaggc tggagtgcaa tggctgggaa tacaggcgtg agccacctca cccggctcaa    4560
gattcttaca catttgactt gcctgtaatc ccagcacttt gggaggctaa ggcgggagaa    4620
ttgcttgaac ccaggaggcg gagattgcag tgagcagaga tggtgccact gcactcagcc    4680
tgggctaacg tgagactcca tctcaaaaaa aaaaaaatta cgtcttgtgt cacagagctg    4740
cagataaacc agagactact cataaccgtg tactttttt ttccccatt tctgatcccg      4800 tctcaacgga aggatgtaat tgaggaaggg cttgattggc cagtgagtct tgaagctgac    4860
accactgctg gtggtatttt cccctctccc tggaaagcat cctgttttta gtgaacctat    4920
taaatgtgta gacaattaat ggcttttgc ttcccctgct gcagacttag cggatcccat     4980
gagattttga ctaccgtctg tgctcagaac agtttgagcc gtatggagga agtctccgca    5040
ccagtcttac tgttggtggt caccaggaag ccagcagtgt gtctgaactg gacacatgtg    5100
gccacttcct agcctccctt tgtcctgcca ctggttggtt gggctgggc cctgggagaa     5160 acatagaatg tgagcaaatc agtccgtggc ccctaagttc cttgttggcc ccgaggcagg    5220
caggagaggg gcgggcacac agggcagctg attttcctag tgtcaatatt aggatgtgac    5280
aatacaaaac accactgggc ctcgccaggc actgcatggt aaacctgttt ttctgggggt    5340
gggacagaac ttggcaccca gttagccaaa ctgaaaagcc atgcagcaaa gagagaaaag    5400
```

```
ctcacttgtt tatttgagtg agggtccctg tcattttgga tatttaagat caagtattct    5460
tgaccgcccc ctccccgaga tggagtcttg ctctgttgcc caggctggag tgcagtggtg    5520
tgatctcagc tcactgcaac ctctgcctcc cgggttcagg tgattctcct gcctcagcct    5580
cccgagtagc tgagattaca ggcgcgtgcc accacaccag gctaatttt gtatttttaa     5640
tagagatggg gtttcaccac gttggccagg ttggtcttga actcctgacc ttgtgatccg    5700
cccgcctcag cctcccaaag tgctgggatt acaggtgcga gccaccgtgc ctggccaaga    5760
gatgacattt attgtgtgtg acagtatctt cgagattaga ggctcccttt catgtgaggg    5820
caaagagagc tacctgattc caggaggagc tgaaattccc tgtgcagaca atggcgcatc    5880
atgaagataa atccgagctc ggaccgtgag gtggtcagca cgggtgtgcg cctcgcagag    5940
caacaggctc acagaatgag agctgcctct tagtgggcac ttactgcata ccatgcatgc    6000
agcatttcac ctccttctca gggctacatc tgcccatggg gctttccctc ctgcccttta    6060
acagaaggtg atactgtcca gtccagggtc tcccagccag gaacagcctg ccatcgtgag    6120
cccagcacca gagtaacccc ttccctcatt ctcaggattt tgcagtgaac tctcaggctg    6180
tctgcatcct ctcaccggct ttcactgggt ccctgctctg ttctggggcc atgcaggttc    6240
ccgactggct ggggcagaca cacaggtaaa catttaacga gaccttgatg gctgagtgc    6300
ccaatccagg tctgtttacc caaggtgctg gacaacaca gatgaggagc atttaattct     6360
gtcctgggga gggtggggag gaagtgactt gtgcctgagc cccaaggaag cagtgagtcc    6420
cccgtgcctg cctgggggat gttggtaaca gaggaggat gtaaaggagg agctggggtg     6480
tgaaagggct gggtgcaagt tcataggga gacccaaaca ctgaagtgga gcccagggc      6540
cgtacctgcc tctcaagcct cagggtcggg gccaggtga gcagtcttca tattcttcag     6600
cctcagcatt tcagaacttg ttttatttt tttttgagat ggagccttac tcctgtcgcg     6660
ggggctggag tgcagtggcg cgatctcggc tcactgcaac ctccacctcc tgggttcaag    6720
tgattctcct tcctcagcct ccctagtagc tgggattaca ggcgtgcgcc accacgcctg    6780
gctagttttt gtattttag tagagatgag gtttcgccat gttggccagg atggttgtga     6840
actcctgacc tcagttgatc cacctgcctc aacctcccaa agtgctagga ttataggtgt    6900
gagccaccgc gtctggccta tttttatt ttgattgagt cttgctctgt tgcccaggtt      6960
agagtgcggt ggcacgatct tggctcactg caacctctgc ctctcaggtt taagtgattc    7020
tcctgcctta gtctcccgag tagcttggac tacaggtgcc cgccaccacg cccggctaac    7080
tttggtattt ttagtagaga cactgtttca ccatgttgac cggggggtct tgaactcctg    7140
accttagttg atccatctgc cttgacctcc caaagtgctg ggattacagg agggagccac    7200
cgcgccccgg cccagaactt gttttaaata tgaacttttg aaacttaaca actgtaggcc    7260
caggtggtgg cttggcattc tctgcttcct tcatggtgat aaaaaggcac aggcttcccc    7320
tttttgggt catttcaaaa tcagtcaaga gaattattag tctgttagac ttcctctacg     7380
gttaggatta ttttatagg tgttcgaaca ggaaaggaca tagaataaaa tctcctcccc     7440
taacttattg atacagggtc tcactctgtc gcccaggctg gagtgcagtg gcgcagtcac    7500
agctcactgc agcctcaacc tcctgggctc aagtgatcct ttcgccttgt gctcttaaag    7560
tgctgggagc ctccaaaagg ctaagctgtg acgttgggta ggttacatgt attaaatgca    7620
tttttttttt tttgagacag ttttgttctt gtcacccagg ctggagtgta atggcataat    7680
ctcggctcac tacaacctct gcctcccagg ttcaagtgat tctcctgcct cagcctcccg    7740
agtagctggg attacaggcg cccaccccca cgcccggcta attttgtat tttagtaga      7800
```

```
gacagagttt caccgtgtta gccagaatgg tttcgatctc ctgacctcgt gatccgcccg   7860
cctcggcctc ccaaagtgct gggattacag gcgtaagcca ccgtgcccgg cctggtgaaa   7920
ccccgtcttt actaaaaata caaaattagc caggtgtggt ggcgtgcacc tgtagtccca   7980
ggtacttggg aagttgaggt ggaaagatca cctgagccca gggaggtgga gactacagtg   8040
agccatgttc atgccactgc actccagcct gggtgacaga gagaccctgt ctcaaaatag   8100
taatactcca tattgggcct ctcacagggg aatcttgggg ggagctgcag ctcagggtga   8160
ctcccatctt gtcactagcc aggtgacccc ttcattctgg agccttagct ctgaaagccg   8220
caggtggggg tgccgtttca gatgcccctt ttccatttca aaggctctga ttctagatct   8280
tgaagccgga tgcggcactg gcacttggct tcagtttcca ctgtgacgga cggaggtctc   8340
ccaggcccag cccaggcagc caagcccatc ctggaatcag aacacgctga gcacattttg   8400
tagggtggca ccttttttatc caagttacta gctacacatc agtgtttaaa gagaaaaaag   8460
tgagctgtct tttttttttc ttgaaacttg aggaaacaag gtacatacta cggattttt    8520
tttttctttt tcttttttt  ttttgagaca gtctcactct gtcgcccaga ccggagtgtg   8580
gtggcatgat ctcggcttac tgaaagctct gcctccaggg ttcaagccat tctcctgcct   8640
cagcctcccg agtagctggg actacaggcg cccgccacca cgcccagcta atttttttg    8700
tattttagt  agagacaggg tttcactgtg ttagccagga tgctctccat ctcctgacct   8760
tgtgatctgc acgcctcaac ctcccaaagt gctgggatta caggcgtgag ccaccgcgcc   8820
cggcccatat ttttttttt  tgagatgagt ttttcgctc  ttgtcgccca ggttggagtg   8880
taatggtgtg atctcggctc actgcaaact cctcctccca ggttcaagcg attctcctgc   8940
ctcagccacc cgagtagctg gattacaggc gcgcaccacc acacctggct aatttttttt   9000
gaaacggggt agagacggag ttttattacc atgttagtca ggctggtctt gaactcctga   9060
cctcatgatc tgcccacctt ggcctcccaa agtgctggga ttacaggtgt aagccaccgc   9120
ggctggccca tttcatatat ttttaaaatt ttttattgtt aatttatttt tagagagggg   9180
gtctcgttgt attgcccagg ctggtcttga actgggctcg tgcgacgtgc ccgcctcggc   9240
ctcccgaagg gctgtgatga cagcacagcg gtgcctgtga tctatggctt caattttca   9300
aggctgccag gtccatgcag gggtgtgtgt gggatgcatc cctagaaatc aaaggtcatg   9360
tgcgtgtgtg actggtggat gctgatggtc acactaccct ccagaaaggc agcaacatgt   9420
tcagtccacc gtggcgtcct gagctgtgag tggcctctgg tctcctctct tctaaggctg   9480
ttgattgtgt taaccagctt ttatggagcc cctgctaggt ggtggaaaat gggcagtagt   9540
gtatgtttc  atcctctcag cagccctgga ggcccggctg tttctgcaag gctcagaggt   9600
gagctggttg ttctgcctca cacagcaggg gccgagcagg gggtggaact gaggtccagc   9660
ctggctgcag gctcagggcg tttcctgctg ggttacactg gagttgtgtg cgctccaagg   9720
gctttgtgcc accccaccct catggtccag gccaggctg  tgactgggag ggtggcacgt   9780
ggaagactgg accagggttt tctagctggg cccactcagc tggccctccc tgtgacccca   9840
gcgtggcccc tgaccctctc ggtttgcctg cctgtgaaac aggaagtgtc agatcccgcc   9900
tgcttggctt tgacaggact gggcgaggtc atgagagtct gagggtccct accaggagtt   9960
cgacctcatc ctcaggtcca gccccatcca cctctgcccc caacccgct  ctgacactcc  10020
tgcagcctcg gccctcgaac acctgctgag ggctgagcag aacacatctc tacttgcttg  10080
tgcttctggg caacctggga ggggcttggg aggtagatgg cgtttcccca tcttccagat  10140
gagccatagg cgagctgtcg agtgcagagc tgttcaccaa atgtaggctg ctctgtccag  10200
```

```
aacctgccct ccctcccact cggagccctg caggtgccct caaggccgtg ggtgtggtac   10260
tcttttctgc acatactaga tttgcatcct aacctcttag ggtaaaatag ggcttctgac   10320
tggcgcctgg tgtttccact ggtgagtgtg taggaggcta agtgcgggct gtagcctggg   10380
tggggacaca tggctaggtg tgtcttcctt caccaaagaa gggtttcaac tactcatttg   10440
caagtttgct ggaaaaaaaa agataataaa aaccagtcca gtttcctgta tctgcagctg   10500
cagtgacctc acagtgggtc ctctgggaat aggttgcctt catgtcttca gtcaacaaac   10560
atatgtctgc tctatgccag gccttgggct gacaaccaga aactgataag agcagcagcc   10620
cctctcttag cggtttactc tgtgccggat catttcatcc ccacaacagt cctgtgcaat   10680
aggtgttact agtatctcca ttctaatttt tttttttct gatatggagt cttgccctgt   10740
agcccagcct ggagtgcagt ggtcagctgg agccagaggg gagcagagac aggggctgca   10800 ggaccccag gaggccccca agcagactct gagggtccaa gaaggtgatg cccgaatagg   10860
ccagcctcat acccatcctc tcagtacttt gggaggccca ggcggagtt gaagccagga   10920 gttccgagac aagcctgggc aacaaagcaa gaccctatct ctacagcaat tctataaaaa   10980
tgagccaagt gcagtggtac atacctgtcg agttaccctg gaggctgagg tgggatgatt   11040
acctgagccc aggagtttga ggctgtagtg agcatgatca ggccactgca ctccagcctg   11100
ggcaaacggg tgagaccctg tctgtgaaaa aaataataat aaaatttaat ttttaaaaaa   11160
ggaccaatag gcgtaggcat gggccggtct gaggttggct ggtgagctct gcacatttga   11220
agactttgga ggcatggcag gaccaggcac catccatgga aagcatactt gagtgtggtt   11280
agcgcgggaa ccaagattgg ggtggcaggg ccacaggggg agggcctgtt agtggatgtg   11340
gcacaacccc ccacttgttt ttgagacaag tcttgctctg tcacccaggt tggagtgcaa   11400
tggcgcggtc tcggctcact gcatattctg cctcctggat tcaagtgatt ctcctgcctc   11460
agcctcccaa gtagctggga ttataggcga gcgccaccac acctggttaa tttttgtatt   11520
tttagtggag atggcgtttc accatgttag ccaggctagt ctcaaactcc taagctcagg   11580
tgatccacct gcctccacct ctcaaagtgc tgggattaca ggcgtgagcc gcactgcacc   11640
aggccaggtc tagggagccg aacagagcag tgacagggtc agggttgagg ctgctacctt   11700
gagattaggt tggagagagc tccactgaag gctggagacc agtaaggcat tcagagctgg   11760
tgccaggtag gagctgacag gactgggcct cccttgggct ggtggggtgg ccaggagaga   11820
ccagagcagg aggtcgctgc tgcaaggacc ctcctgggca ggctccccac cttccgctcc   11880
ctggctccac acttttccca tgcagatctg ggccctaagg ccagcctagg cccagttggt   11940
gatgggatct ttgccattca tatcaagtca atctgagggc ctgggcccag aggccagatg   12000
gttaaaggtt cagattaggt cccttctttg tggtagaggg taatgggtat ttaataaatt   12060
aatccaaagt gctgtaatcc cagtactttg ggaggctgag gcgggtggat cacttgagat   12120
caggagttga gaccagcctg gccaacatgg taaaaccccg actctactaa aaatacaaaa   12180
attagccggg tgtggtggca tgtgcctgta atcccagcta cctggagtc tgaggcagga   12240 gaatcacttg aacctgggag gcggaggttg cacctgagct gagatcacac cactgcactc   12300
cagcctgggc aatagagtga gactgtctca aaacaaaca aacaaacaaa caaaaaaca   12360 ctaccaccaa caaaaacaca atagatgggg aaactgaggc tggtgcagga agggttgggc   12420
tagggtatca acctaaggtg agatgtggtc ctgggtctac tcagatgggg aggttggcag   12480
ggtggggagc ttgaaagggt cttgcaggca gagcgtgggt gactgactcc tcaggtaggc   12540
ctgacctgca ctctgctgca gaccctcggc agcgcagccc actctggtgg ctggggcctt   12600
```

```
cttcctatct ggcgcctaag gattctcgga atgcctgctg ggtaaggggg ctgtgggcac   12660
agtgggtcaa ggcgaggctc ggtgcagctc acagctcagc tcacagtgag gtgaggttcc   12720
actgttgctc tggctttgcg gggcgtggag gtactgggt  ctccaggagc acaaagcagg   12780
agactgcctt ttcgagggga agggaaaggg gggaaaagca acaagggct  ggagctgctt   12840 tcctagggaa atgccatttg catagacacc caaggcagct ggaagttctg gacacagttc   12900
ttctaatgcc agcttaacac gcacactgct ggccgtctat acaatgtaaa acatctcatc   12960
tgtgaaacct tattttttct ttttgagtca gaatctagct ctgcctccca ggttcaagct   13020
gggattacag gcgtatgtca ccacgcctgg ctaattttgt attttattta gaggcggggt   13080
tttaccatgt tggccaggct ggtctcaaac tcctgacctc aggtgatccg cctgtctcag   13140
cctcccaaag tgctgggatt acaggcgtga gccaccgcac ccggcccatc catctcc ttt   13200 gaatgctgaa agcaagtcgt gagcacacac ttgtgcctag gcctgtggga gggcggccct   13260
gtgggtcctg cctgccgtca gttttctctc tcctgggggt cagggagact ggagctctg   13320 tcccttcttg gcttagtcat gaacctctct aagcctcagt gtcctgtgtg aacaaacagc   13380
tcagtgagat ggtgggaggg cggagtgtcc tgtcagcagg catggggaat taaaaattaa   13440
gaacacccag ggcattatgg taagaaaata atgagttgaa gcataaaggt aatggttagt   13500
gccaacttcc tcccagcgtg ccaggccctg ttcaaagtac atgaaggagt tccttatttc   13560
gtcttcccaa tagcccaggg cggggctctc agaccatgaa acccatttca cagatgaaga   13620
aattgacaca ctgctgctaa ctgccagagc cgggctttga actaggccat tagatttccg   13680
tgccacagtc atcgtcatta tcgtcatcta catctaaggc tgtttggtac cctgtagggt   13740
aaatgtgggg tacatgatgg tgaatcaggt cgcagaaccc ttctctgcca tcatgatgaa   13800
acatgtactg gcatgggatt cgcaatgatc atagttagga aggcctttgg tggcaaagaa   13860
gaggaaactc agtgaatggt gatgaggaca catttgggtt cattttcctt acacacagtt   13920
ggaggagaca gctcagtgac accctcaggc ctggccgctc tctgcctccc cgctctgctc   13980
ttcttggtca gccactgcag ctccatcttt gaaggagctg ccctggctgt gtctactccc   14040
tggcatccaa cccctgcctc cagcctctga gccctcattg accagaactg ggttacatgg   14100
ttgtcaccag ctgcaaggga tgctgggaag ctgagggaga ggagggccat ggttggctta   14160
gatgaatgag gatgcagggc caccccgaag aaaattgggg ttctatcagc aaggagccag   14220
gtggaatgga tatcggagag gtaaatagca tctgccagta aagaaggctg taagacactg   14280
tatggggtga tcccatttgt gaagaaggat gtgtgatgcg cacaagtgtt taggaaaaac   14340
actagaagaa ttagcgatgg tctctctggg aatggggatt gtgatacgtt tttctcatgc   14400
tgcctctctg cctttcttct caagagaaac agcagacacc aaagaacagg tgtagccttc   14460
tgttaagtgg tacagaggaa tcgccctgca gcctggcctc tgtcccctgt gctgacagca   14520
ggtgcctggg ttttctgctt tgacaggttc ttgagggctg gtgtccgagg agaacttcta   14580
atatttattt atactctgat tttgtttcac aaagaagaaa aaggctgggc gtggtggctc   14640
atgtctgtcg tcccagcact ttgggaggcc gaggtggggt ggatcacttt gaggtcagga   14700
gttcaagacc agcctggcca acatgatgaa acccccgtct ttactaaaaa tacaaaataa   14760
ttagccaggc atagctcatg cctgtagtcc cagctactcg ggaggctgag gcaggagaat   14820
tgcttgaacc caggaggcag aggttgcagt gagccaagat tgtgccactg ccctccagcc   14880
tccagcaaga ctcagtatcc aaaaacaaag aaagaaagaa agggccctta tgaatcatct   14940
tcaagttcct cccttccaag aacagagatg ctaggcgact tgcccagagg cacacagcca   15000
```

```
gcatgtagca ggattcatgc ctgtgggagc tggggttggg ggatattgac ggctttagcg   15060
gatcaaaaga gctggtgagt agggctatac aatctggggg tcatcctgtg agagagcccc   15120
cagactgctc agttcttagg ggtccagtca tatgctgtct ttttgcccca gaggagaaat   15180
gtctgaagta agacccctct ccagagacat cttgatggag accctcctgt atgagcagct   15240
cctggaaccc ccgaccatgg aggttcttgg catgactgac tctgaagagg acctggaccc   15300
tatggaggac ttcgattctt tggaatgcat ggagggcagg taggtcccca tggcctgccc   15360
taccccctgc ctgatagtga cttcagggggg ggctggatg agcagacctt ctgtgagcgg   15420
gggagcgcct gcagatgcct cccaggcagg gcctccgaga ggaagatttc cggatgtgg   15480 gcatggaggc ttctgccctg ggagcggctt cactttgctg ccccaccctc ccctgatacc   15540
agctcacaga cccctggaca gccagcatgt tcacagtctc aagatggacc tggggcccct   15600
ggctgtcaaa atggcacagt gtttgggcct cagggagcta gacaggccct tagcgacctg   15660
ctgaggacat cagggcctct tgaaggaggt gactctgttg ccagaaaggg gacccgatcc   15720
agatcccaag agagggttct tagatctcaa gcaagaaaga atttgggcca cacgcagtgg   15780
ctcgcgcctg taatcccagc acttaggag gctgaggcag gcggatcact tgaggtcagg   15840
agctcgagac cagcctggcc aacatggcaa aaccctgtct ctactaaaaa tacaaaaagt   15900
agctgggcct ggtggcacat gtctgtagtc ccagctagtc gggaggctga ggcaaggaga   15960
atctcttgaa cccaggaggc agaggttgca gtgacccaag gttgcaaaaa tgcactccag   16020
cctgggcaac agagcgagac tccatctcaa aaaaagaaaa cctactctat aggcagagca   16080
gcggcatggg ctgctcaact gaatatactt atagttattt cctgattaca tgctaaacaa   16140
ggggtggatt attcatgagt ttccgggtaa ggggtgggca gttcccggaa ccgagaattc   16200
ctcctccttt tagacaatat agggcaactt cctgacgttg ccgtggcatt tgtaaactgt   16260
cgtggcactg gtgagtgact ccaacatgct aatatagttg gtgcacaatg aatagtgagg   16320
atgactggag gtcacttttg tgcccatctt ggctttggtg ggctttggct ggcgtctttg   16380
ccgaatcctt ttttatcagc agggtctttg taacctgtat cttatgctga tgtcctatct   16440
catcctgtga cttagaattc ctagcctcct gggaatgcaa cccagtaggt ctcagccttt   16500
tgttacccag cccctaatca agatggagtc gctctggttc aactgcctct gacggctctc   16560
attttagaaa accagaaccg ggccgggcgc cgtggctcat gcctgtaatc ccagcacttt   16620
gggaggctga ggtgggcgga tcacctgagg ttgggagttc gagactagcc tggccaacat   16680
ggtgaaaccc aacctctact aaaaatacaa atgttaccca ggtatgggc cggggtggg   16740 gggatgggcg ctggtagtcc cagctactca ggaggctgag gcaggaaaat cacttgaacc   16800
cgggacgtgg aggttgcagt gagccctgag attgcaccac tgcactccag cctgggtaac   16860
agagtaagac tccgttttcac aaaaaaagag aaagagaaaa gaaagaaaga aaaagaaag   16920 aaaaccagaa cctatggaag agcctgagga ggccatgcag ttcctggtcc cggcttcaaa   16980
gaatcactga ggcatgaaga agggatcttc cttggactga caaggaccct ggaggcagca   17040
ggatttgcct ggggtttcag gggccaaggt ccagtaggac ctgacccttg cactctgcca   17100
actgctccca gctatgtcca gcacacggca gcatacccag atgtccaggc acacccggcc   17160
atcccagcgg caggaaggac ctgcactttt ttttttttttt tttgagacag agtctctgtc   17220
acccaggctg gagtgcagtg gcatgatctt ggctcactgc aacctccacc tcccgggttc   17280
aagtgatttt cctgcctcag cctcctgagt agctgggagt gcaggcgtgc accagcatgc   17340
ccggcttttt ttttttttttt gagacggagt ctcgctgtgt cgcccaggct ggagtacagt   17400
```

```
ggcatgatct ctgctcacca caagctccac ctccctggtt tacgccattc tcctgcctca   17460
gcctcctgag tagctgggac tacaggcgcc tgccaccaca cctggctaat ttttttgtatt  17520 ttcagtagag acagggtttc atcatgttag ccaggatggt ctcgatctcc tgacctcgtg   17580
atctgcctgc ctcggcctcc caaaaagtgc tgggattaca ggcgtgagcc accacacccg   17640
gccaggactg gcactttcat tcttcccctg gtacagatga ggaacgtgaa ggcccaggag   17700
cagctgacct cagtagtttc taccctgagc ctggaagaga atggtcaggc ctgacctggg   17760
ctgttgcttt ctgctgggga atcctgtctc tgatgtggca cctcccacag gccagggacc   17820
agctccatgt tccacaggat tcttttctgc tcaggatttt ttttttcagc ctcaggattt   17880
ttagtcatta aggattttag aactggaggc acctgtccat taatgacaa  ggttggagga   17940 catgaagcct ggggcagtat tttcctgagg tttcccaggg taacagaagg taggaccaca   18000
gcccccaacc ctgattgcca gcccacacct gtaccctcc  cacccgcatc ccctccaagt   18060
agggagtgta ggcccagggc attggcaggt caggtgggtg gggccagggc ccagggccgg   18120
cctcagctca gggcccctag gagtcccact tccctgggag ttcccccggt gtagtcactg   18180
ggatggaatg cacacaggtc cctggtagag gcccagacca gcaagctggg agggtgggga   18240
gtgtcttagt ctttgtgtgg gagtgaatgc gggtggggtg taggatcaag gatgtggttt   18300 agtgggggc  ctactagggg cttcttagtc ccccattcg  gagagggtg  gtgccagcag   18360 ggctggtttc aggattggga ccaggacaca ggtcttagag ccccctcacc tcccacaaag   18420
gaaggtaagc tgcaacccct gtgggaaggg ggctcaaggg ggctcagcca tccggggac   18480 tcagcaccac cagacctgtc cattcccctt ggtcagcctc agccatccgg gggctcagca   18540
cccccagacc tgcctgttcc ccttgtccac catttccacc aaagcccaca ggtgggcctg   18600
ccccaggatt cttttgaaa  tagcttgcac ctctggggcc acccacggat gggacctcat   18660
gggtatctct gaatccaagt gggagccgga ggagggatac agggaggccc actcactgcc   18720
tgccccaaat ctgacaccat ctcttatcct ctgggccact cccagctgca cacaatccgt   18780
tggctgggtg ggtccaggtg catgtggcct ccacggcaca gccacacccg actcctgtgt   18840
gtgctccctg cagtgacgca ttggccctgc ggctggcctg catcggggac gagatggacg   18900
tgagcctcag ggccccgcgc ctggcccagc tctccgaggt ggccatgcac aggtagccgg   18960
cctatgccct atgcctctac acctggggag gggccctggg cggtgggtgg aggccctgaa   19020
cacagcacag ggctgggccc tgaggaagct ctgtggggga tgtgccttga cactctgggg   19080
ctatactgaa acccttggct gcttcccgca cctctcctgg gagcccccag ctcctggcac   19140 tcgcccctg  ccacctgtcc ctggcattcc tgggcaacaa agcagagccc agggcccttt   19200
tctctctcgc cgtcctcatt gagcccagat ggtacatttc caccgtggtc ttaagagggg   19260
gtgctacgtg agctcggatc ctagatcctg ggggctgggc ctctcagcga gtctccggtg   19320
ggggaataga gtgggcagtg gcttgtgagg gccctgtaga atgggggttt attttccacg   19380
tggccagctc tggaagacag ggccaaacac ccggtgggct ggcgggcggc tggctggcgg   19440
aggaagcagg aagttggaat gaatttgacc acaaacagtc cataccacgc ggcccctgca   19500
ggtggaggcg cccacggaaa gggccccggg tggctgtggg gtgggagggc acaggcccct   19560
gctccccaca gctgtgatgg tgtcatctaa gtacaggctg cccctacctg ctcctgcagt   19620
aatggctttg tccccccatc ctctttgtct atagcctggg tctggctttc atctacgacc   19680
agactgagga catcagggat gttcttagaa gtttcatgaa cggtttcacc acacttaagg   19740
agaacataat gaggttctgg agatccccga accccgggtc ctgggtaaga gccttgagat   19800
```

```
ccctgaccct gacttgcgct gcggccagtg ggggctgtca gagccgctcc ttggggcgcc    19860
acagtcccca ccactccgta tcatcatctg tgtcacctgt gtccacatct gcctgatccc    19920
atgggctttt gggtttgaga tgcctggttc tgagtgcaca aaccagtgca tggtcctggg    19980
tctccctctg gtccgagagc cttcacctgg caggcaggac tcccgtctcc tggccagggc    20040
aggggcctcc ctgagcagcc ttcctggtag cctggtccca tggtgtccac tcggcaccgc    20100
ccaccacaag ggcagctgac tgccctcacc tgtgcccacc gggtgtcttt gcctgtgtcc    20160
cgcagactgg caggcccagg ccacgctggc ctctctggcc acgtcctcag ggccactttc    20220 ccctctcct gaactccttc cttctctggt ccctcgagc tccttcccag tccccaccct     20280
cctgggcttc cccttggcac tccgctgtca cccgtctggc cccattgctg gggcctgccc    20340
cgagcctgac tcctctgctt tgctcccaca ggtgtcctgc gaacaggtgc tgctggcgct    20400
gctgctgctg ctggcgctgc tgctgccgct gctcagcggg ggcctgcacc tgctgctcaa    20460
gtgaggcccc ggcggctcag ggcggggctg gccccacccc catgaccact gccctggagg    20520
tggcggcctg ctgctgttat cttttaact gttttctcat gatgcctttt tatatttaaa     20580
ccccgagata gtgctggaac actgctgagg ttttatactc aggtttttg ttttttttt      20640 attccagttt tcgttttttc taaaagatga attcctatgg ctctgcaatt gtcaccggtt    20700
aactgtggcc tgtgcccagg aagagccatt cactcctgcc cctgcccaca cggcaggtag    20760 caggggagt gctggtcaca cccctgtgtg atatgtgatg ccctcggcaa agaatctact     20820
ggaatagatt ccgaggagca ggagtgctca ataaaatgtt ggtttccagc agtctctggt    20880
cctctctggg gggttggcag caccagcacg ggcttcctct cgcccaggg aggcacactg     20940 tgttggtggg gagggcaggg cctgtgtgct cctaatcaga tccttccctg caaaagggga    21000
ccgcaaatgc tgccttggtt tggcccgacg gtttgccttc tcccttgtcc cggtctgtgg    21060
cctaaaatcc actgttgggg gttatttcct ttgggctttc agttcctctt taggggatgc    21120
ctgcctctcc ctgcacagac tcctcaccac agggatgcag ccgtggctcc gctcacaggg    21180
agaggtgtgg tggggattgg ggagcaggac aaggggcacc aggggcagga gggcaggac    21240 cctgctttgt acctttgtag gcttggtacc tgccctgggc cttggcctcg tgccatttgt    21300 agacccacc aggcctccct cccaggacat cggctctgtg tctgccctcc accccaaatg     21360
tcaaagctgg gctgggccgg ccaccattct ccagccccca accccctca tccccagagc     21420 tgggagatgc agctgttcat acctcccagg ctggctgggc agaccctgca tcctgctcac    21480
tcctccctcc atcctggcct ccaaaccaaa ggggacctcc aataggcttt cctgcctcct    21540
tatgtcttct ctccggtctg                                                21560
```

<210> SEQ ID NO 6
<211> LENGTH: 963
<212> TYPE: DNA
<213> ORGANISM: Artificial Sequence
<220> FEATURE:
<223> OTHER INFORMATION: Description of Artificial Sequence: Synthetic Primer

<400> SEQUENCE: 6

```
gacacgaagc ctcccgggtg gcttacagac gctgccagca tcgccgccgc cagaggagaa      60
atgtctgaag taagacccct ctccagagac atcttgatgg agaccctcct gtatgagcag     120
ctcctggaac cccgaccat ggaggttctt ggcatgactg actctgaaga ggacctggac      180
cctatggagg acttcgattc tttggaatgc atggagggca gtgacgcatt ggccctgcgg     240
```

```
ctggcctgca tcggggacga gatggacgtg agcctcaggg ccccgcgcct ggcccagctc    300
tccgaggtgg ccatgcacag cctgggtctg gctttcatct acgaccagac tgaggacatc    360
agggatgttc ttagaagttt catggacggt tcaccacac ttaaggagaa cataatgagg     420
ttctggagat ccccgaaccc cgggtcctgg gtgtcctgcg aacaggtgct gctggcgctg    480
ctgctgctgc tggcgctgct gctgccgctg ctcagcgggg gcctgcacct gctgctcaag    540
tgaggccccg gcggctcagg gcggggctgg ccccacccc atgaccactg ccctggaggt     600
ggcggcctgc tgctgttatc ttttttaactg ttttctcatg atgcctttt atatttaaac    660 cccgagatag tgctggaaca ctgctgaggt tttatactca ggttttttgt ttttttttta    720
ttccagtttt cgttttttct aaaagatgaa ttcctatggc tctgcaattg tcaccggtta    780
actgtggcct gtgcccagga agagccattc actcctgccc ctgcccacac ggcaggtagc    840 aggggagtg ctggtcacac ccctgtgtga tatgtgatgc cctcggcaaa gaatctactg     900
gaatagattc cgaggagcag gagtgctcaa taaaatgttg gtttccagca aaaaaaaaa    960 aaa                                                                 963
```

<210> SEQ ID NO 7
<211> LENGTH: 160
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Met Ser Glu Val Arg Pro Leu Ser Arg Asp Ile Leu Met Glu Thr Leu
1               5                   10                  15

Leu Tyr Glu Gln Leu Leu Glu Pro Pro Thr Met Glu Val Leu Gly Met
                20                  25                  30

Asp Asp Ser Glu Glu Asp Leu Asp Pro Met Glu Asp Phe Asp Ser Leu
            35                  40                  45

Glu Cys Met Glu Gly Ser Asp Ala Leu Ala Leu Arg Leu Ala Cys Ile
        50                  55                  60

Gly Asp Glu Met Asp Val Ser Leu Arg Ala Pro Arg Leu Ala Gln Leu
65                  70                  75                  80

Ser Glu Val Ala Met His Ser Leu Gly Leu Ala Phe Ile Tyr Asp Gln
                85                  90                  95

Thr Glu Asp Ile Arg Asp Val Leu Arg Ser Phe Met Asp Gly Phe Thr
            100                 105                 110

Thr Leu Lys Glu Asn Ile Met Arg Phe Trp Arg Ser Pro Asn Pro Gly
        115                 120                 125

Ser Trp Val Ser Cys Glu Gln Val Leu Leu Ala Leu Leu Leu Leu Leu
    130                 135                 140

Ala Leu Leu Pro Leu Leu Ser Gly Gly Leu His Leu Leu Leu Lys
145                 150                 155                 160

<210> SEQ ID NO 8
<211> LENGTH: 160
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Met Ser Glu Val Arg Pro Leu Ser Arg Asp Ile Leu Met Glu Thr Leu
1               5                   10                  15

```
Leu Tyr Glu Gln Leu Leu Glu Pro Pro Thr Met Glu Val Leu Gly Met
            20                  25                  30

Thr Asp Asp Glu Glu Asp Leu Asp Pro Met Glu Asp Phe Asp Ser Leu
            35                  40                  45

Glu Cys Met Glu Gly Ser Asp Ala Leu Ala Leu Arg Leu Ala Cys Ile
            50                  55                  60

Gly Asp Glu Met Asp Val Ser Leu Arg Ala Pro Arg Leu Ala Gln Leu
65                  70                  75                  80

Ser Glu Val Ala Met His Ser Leu Gly Leu Ala Phe Ile Tyr Asp Gln
            85                  90                  95

Thr Glu Asp Ile Arg Asp Val Leu Arg Ser Phe Met Asp Gly Phe Thr
            100                 105                 110

Thr Leu Lys Glu Asn Ile Met Arg Phe Trp Arg Ser Pro Asn Pro Gly
            115                 120                 125

Ser Trp Val Ser Cys Glu Gln Val Leu Leu Ala Leu Leu Leu Leu Leu
            130                 135                 140

Ala Leu Leu Leu Pro Leu Leu Ser Gly Gly Leu His Leu Leu Leu Lys
145                 150                 155                 160

<210> SEQ ID NO 9
<211> LENGTH: 160
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 9

Met Ser Glu Val Arg Pro Leu Ser Arg Asp Ile Leu Met Glu Thr Leu
1               5                   10                  15

Leu Tyr Glu Gln Leu Leu Glu Pro Pro Thr Met Glu Val Leu Gly Met
            20                  25                  30

Asp Asp Asp Glu Glu Asp Leu Asp Pro Met Glu Asp Phe Asp Ser Leu
            35                  40                  45

Glu Cys Met Glu Gly Ser Asp Ala Leu Ala Leu Arg Leu Ala Cys Ile
            50                  55                  60

Gly Asp Glu Met Asp Val Ser Leu Arg Ala Pro Arg Leu Ala Gln Leu
65                  70                  75                  80

Ser Glu Val Ala Met His Ser Leu Gly Leu Ala Phe Ile Tyr Asp Gln
            85                  90                  95

Thr Glu Asp Ile Arg Asp Val Leu Arg Ser Phe Met Asp Gly Phe Thr
            100                 105                 110

Thr Leu Lys Glu Asn Ile Met Arg Phe Trp Arg Ser Pro Asn Pro Gly
            115                 120                 125

Ser Trp Val Ser Cys Glu Gln Val Leu Leu Ala Leu Leu Leu Leu Leu
            130                 135                 140

Ala Leu Leu Leu Pro Leu Leu Ser Gly Gly Leu His Leu Leu Leu Lys
145                 150                 155                 160

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 10
```

```
Ala Leu Arg Leu Ala Cys Ile Gly Asp Glu Met Asp
  1               5                  10
```

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      Primer

<400> SEQUENCE: 11

```
Leu Arg Leu Ala Cys Ile Gly Asp Glu Met Asp Val
  1               5                  10
```

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

```
Ala Leu Ala Leu Arg Leu Ala Cys Ile Gly Asp Glu Met Asp Val Ser
  1               5                  10                  15
Leu Arg
```

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

```
Leu Ala Leu Arg Leu Ala Cys Ile Gly Asp Glu Met Asp Val Ser Leu
  1               5                  10                  15
Arg Ala
```

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic
      Primer

<400> SEQUENCE: 14

```
Glu Gln Val Leu Leu Ala Leu Leu Leu Leu Ala Leu Leu Leu Pro
  1               5                  10                  15
Leu Leu Ser Gly Gly Leu His Leu Leu Leu Lys
                 20                  25
```

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15

```
aggacccagg tacctatgtt caaaagtgcc tc                               32
```

```
<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
ccttgcctgc tgctttccac caagtgct                                              28

<210> SEQ ID NO 17
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
caggttggga aaatggtcag ccctcctgaa a                                          31

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
cgttctgagg cgggcaatca aatgacctat                                            30

<210> SEQ ID NO 19
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
cccgctagcc taattttatt ttatttttaa ttc                                        33

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
cccctcgagg tattttggaa aaatgtcctt atctag                                     36

<210> SEQ ID NO 21
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
cgcacgcgta ggcatcagct ctctacaatt c                                          31

<210> SEQ ID NO 22
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
agcctcgagc aggatctgag ataagaacca cg                                   32

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
acggcgctcg agtccatcag ttctcatc                                        28

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
ttacttaagc ttgtgtagga cgcctgtc                                        28

<210> SEQ ID NO 25
<211> LENGTH: 452
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
tacgggccag atatacgcgt tgacattgat tattgactag ttattaatag taatcaatta     60
cggggtcatt agttcatagc ccatatatgg agttccgcgt tacataactt acggtaaatg    120
gcccgcctgg ctgaccgccc aacgacccccc gcccattgac gtcaataatg acgtatgttc    180
ccatagtaac gccaataggg actttccatt gacgtcaatg ggtggagtat ttacggtaaa    240
ctgcccactt ggcagtacat caagtgtatc atatgccaag tacgccccct attgacgtca    300
atgacggtaa atggcccgcc tggcattatg cccagtacat gaccttatgg actttcccta    360
cttggcagta catctacgta ttagtcatcg ctattaccat ggtgatgcgg ttttggcagt    420
acatcaatgg gcgtggatag cggtttgact ca                                  452

<210> SEQ ID NO 26
<211> LENGTH: 180
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
agacggtgag agcgagtcag ggattggctg gtctgcttcg ggcgggctaa aggaaggttc     60
aagtggagct ctcctaaccg acgcgcgtct gtggagaagc ggcttggtcg ggggtggtct    120
cgtggggtcc tgcctgttta gtcgctttca gggttcttga gccccttcac gaccgtcacc    180
```

<210> SEQ ID NO 27
<211> LENGTH: 231
<212> TYPE: DNA
<213> ORGANISM: Artificial Sequence
<220> FEATURE:
<223> OTHER INFORMATION: Description of Artificial Sequence: Synthetic Primer

<400> SEQUENCE: 27

| | | | | | |
|---|---|---|---|---|---|
| cggccgccag | tgtgatggat | atctgcagaa | ttcgcccttg | cgatctgtca | gagcacctcg | 60 |
| cgagcgtacg | tgcctcagga | agtgacgcac | agcccccctg | ggggccgggg | gcggggccag | 120 |
| gctataaacc | gccggttagg | ggccgccatc | ccctcagagc | gtcgggatat | cgggtgaagg | 180 |
| gcgaattcca | gcacactggc | ggccgttact | agtggatccg | agctcggtac | c | 231 |

<210> SEQ ID NO 28
<211> LENGTH: 1757
<212> TYPE: DNA
<213> ORGANISM: Artificial Sequence
<220> FEATURE:
<223> OTHER INFORMATION: Description of Artificial Sequence: Synthetic Primer

<400> SEQUENCE: 28

| | | | | | |
|---|---|---|---|---|---|
| ccttgcctgc | tgctttccac | caagtgctgg | agagctggtg | aattgctcac | tcccggctca | 60 |
| ttcctctaat | gaccgaagcg | tctcgcagat | gcaacctgcc | gtggaggagc | agggagggag | 120 |
| tgatttccag | gtgtgggctt | tttcagccat | tcctaaaggc | gacttgagtt | cacctcactc | 180 |
| actccagcat | ttgtactcct | gttgtggaaa | aggcagtgag | cacaagccaa | gcccgctcca | 240 |
| ccttcacccc | gccccacctc | ccccggccct | ttcctgggcc | agtcttaggg | ccctgagtac | 300 |
| agacagcctg | gctacccgtt | aaccattctc | agcgtgtggc | tgcttttac | acacatgtgt | 360 |
| acatatgcac | ggacacacac | acacacacag | aggcttcccc | agtactcctc | tatataggaa | 420 |
| cccgtcacca | tcccagacat | atgcagaaga | aagcccaaac | cggctgtgtg | agacaggaac | 480 |
| aattaacacg | gtaacagatc | cgataatgca | gaccatcagg | cctaaagaac | acggagggac | 540 |
| tgtgttctac | ctccttatag | aaaagcaatt | agtgcctttt | tagctttgga | accatgcccg | 600 |
| gtggtgtgtg | tgtggacaga | actgctggct | ggttgttaag | ttgctactaa | acacagtgtt | 660 |
| gtttctcgtg | gtctctgccc | ttgttaacta | ggattgaggc | acttttgaac | ataggtacct | 720 |
| gggtcctaag | ggcgaattcc | agcacactgg | cggccgttac | tagtggatcc | gagctcggta | 780 |
| ccaagctcca | gctgggaata | gagataggag | gggacccagc | tggatgcagt | gggcagtggg | 840 |
| ggtcatagag | tcaagagggt | acagaataca | atggggtcct | agtatcatgg | tggaggtcag | 900 |
| aaagagccct | aaaagagagg | gtcaaggtag | gaggttagtg | aaggtccacc | tccaccctct | 960 |
| ccaggacagg | gacatcaggc | cacaattaat | ttctctgcag | ttggtgagtg | gtcatggtct | 1020 |
| ctggagtccc | cagcatccag | agtgtccctg | gtcagtggt | cccccctttc | tgagccacag | 1080 |
| ccactttctc | catcaaatga | ggccagtaat | acccatccca | tagtgatgct | gtgaggatga | 1140 |
| gatgagcatc | tgtaagtgct | gaagataatc | cctgacacat | cccaagcatt | cagcagtgca | 1200 |
| agcatacact | tacacggcac | tccccagagc | caggcatgtg | ctggtgcctc | atacacgtga | 1260 |
| ccacatttga | tcgtcacaat | gacccctgtga | gggagactgt | gcaacagagg | actgaccttg | 1320 |
| ctcaaagacc | tcaggcgttt | cccctcagag | cctgagaggt | catctctttt | tttttttttt | 1380 |
| ttcctttct | ttcttttct | tttccatttc | ttttctttg | caagaggtca | tctctaatgc | 1440 |
| tttggaatat | cctgccagat | tagagtccct | ttgttcacct | gaaggtttgg | gccacaccag | 1500 |

| | |
|---|---|
| atagtctaac ggtgtgattt gtgctgaagg ttttgagcca cactatatca gctagatttc | 1560 |
| tagagcggcc ggccgcaata aaatatcttt attttcatta catctgtgtg ttggtttttt | 1620 |
| gtgtgaatcg atagtactaa catacgctct ccatcaaaac aaaacgaaac aaaacaaact | 1680 |
| agcaaaatag gctgtcccca gtgcaagtgc aggtgccaga acatttctct atcgataggt | 1740 |
| accgagctca tttaggt | 1757 |

<210> SEQ ID NO 29
<211> LENGTH: 646
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 29

| | |
|---|---|
| aatcaacctc tggattacaa aatttgtgaa agattgactg gtattcttaa ctatgttgct | 60 |
| cctttacgc tatgtggata cgctgcttta atgcctttgt atcatgctat tgcttcccgt | 120 |
| atggctttca ttttctcctc cttgtataaa tcctggttgc tgtctcttta tgaggagttg | 180 |
| tggcccgttg tcaggcaacg tggcgtggtg tgcactgtgt ttgctgacgc aaccccccact | 240 |
| ggttggggca ttgccaccac ctgtcagctc ctttccggga cttttcgcttt cccctccct | 300 |
| attgccacgg cggaactcat cgccgcctgc cttgcccgct gctggacagg ggctcggctg | 360 |
| ttgggcactg acaattccgt ggtgttgtcg gggaagctga cgtcctttcc atggctgctc | 420 |
| gcctgtgttg ccacctggat tctgcgcggg acgtccttct gctacgtccc ttcggccctc | 480 |
| aatccagcgg accttccttc ccgcggcctg ctgccggctc tgcggcctct tccgcgtctt | 540 |
| cgccttcgcc ctcagacgag tcggatctcc ctttgggccg cctccccgcc tggaattcga | 600 |
| gctcggtacg ggctcgacta gagtcggggc ggccggccgc ttcgag | 646 |

<210> SEQ ID NO 30
<211> LENGTH: 819
<212> TYPE: DNA
<213> ORGANISM: Artificial Sequence
<220> FEATURE:
<223> OTHER INFORMATION: Description of Artificial Sequence: Synthetic
Primer

<400> SEQUENCE: 30

| | |
|---|---|
| ttatgtcaca ccacagaagt aaggttcctt cacaaagatc ccaagctgtc gatcgacatt | 60 |
| tctagaggat ctcggacccg gggaatcccc gtccccaac atgtccagat cgaaatcgtc | 120 |
| tagcgcgtcg gcatgcgcca tcgccacgtc ctcgccgtct aagtggagct cgtcccccag | 180 |
| gctgacatcg gtcggggggg cggatctcgg acccggggaa tccccgtccc caacatgtc | 240 |
| cagatcgaaa tcgtctagcg cgtcggcatg cgccatcgcc acgtcctcgc cgtctaagtg | 300 |
| gagctcgtcc cccaggctga catcggtcgg ggggcggat ccccgggct gcaggaattc | 360 |
| cggcgataca gtcaactgtc tttgaccttt gttactactc tcttccgatg atgatgtcgc | 420 |
| acttattcta tgctgtctca atgttagagg catatcagtc tccactgaag ccaatctatc | 480 |
| tgtgacggca tctttattca cattatcttg tacaaataat cctgttaaca atgctttttat | 540 |
| atcctgtaaa gaatccattt tcaaaatcat gtcaaggtct tctcgaggaa aaatcagtag | 600 |
| aaatagctgt tccagtcttt ctagccttga ttccacttct gtcagatgtg ccctagtcag | 660 |
| cggagacctt ttggttttgg gagagtagcg acactcccag ttgttcttca gacacttggc | 720 |
| gcacttcggt tttctttgg agcacttgag cttttttaagt cggcaaatat cgcatgcttg | 780 |

```
ttcgatagaa gacagtagct tcatctttca ggaggctag                    819
```

<210> SEQ ID NO 31
<211> LENGTH: 1352
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 31

```
acagacattg acattgtgtc atctagtata caaataggtt cttggagtac tttactaggc    60
atggacaatg cccaatgcct gtcccattct tcaggcatat ttttatttgt gggctttatg   120
tccctattaa gaaaaagact aagaacaaga tgctatcata ttttcttaac tggaatggta   180
gatgtttaaa catgatgact accaagcttg gctagaacat tgtgtcatct agtatacaaa   240
taggttcttg gagtacttta ctaggcatgg acaatgccca atgcctgtcc cattcttcag   300
gcatattttt atttgtgggc tttatgtccc tattaagaaa aagactaaga acaagatgct   360
atcataagct ccaagcttat cgccagctgg gaatagagat aggagggac ccagctggat    420
gcagtgggca gtgggggtca tagagtcaag agggtacaga atacaatggg gtcctagtat   480
catggtggag gtcagaaaga gccctaaaag agagggtcaa ggtaggaggt tagtgaaggt   540
ccacctccac cctctccagg acagggacat caggccacaa ttaatttctc tgcagttggt   600
gagtggtcat ggtctctgga gtccccagca tccagagtgt ccctggtcta gtggtccccc   660
ctttctgagc cacagccact ttctccatca aatgaggcca gtaatacccca tcccatagtg   720
atgctgtgag gatgagatga gcatctgtaa gtgctgaaga taatccctga cacatcccaa   780
gcattcagca gtgcaagcat acacttacac ggcactcccc agagccaggc atgtgctggt   840
gcctcataca cgtgaccaca tttgatcgtc acaatgaccc tgtgagggag actgtgcaac   900
agaggactga ccttgctcaa agacctcagg cgtttcccct cagagcctga gaggtcatct   960
ctttttttt tttttttcc tttctttctt tttcttttcc atttcttttt ctttgcaaga    1020
ggtcatctct aatgctttgg aatatcctgc cagattagag tcccttttgtt cacctgaagg   1080
tttgggccac accagatagt ctaacggtgt gatttgtgct gaaggttttg agccacacta   1140
tatcagctag atttctagag cggccggccg caataaaata tctttatttt cattacatct   1200
gtgtgttggt ttttgtgtg aatcgatagt actaacatac gctctccatc aaaacaaaac    1260
gaaacaaaac aaactagcaa aataggctgt ccccagtgca agtgcaggtg ccagaacatt   1320
tctctatcga taggtaccga gctcatttag gt                                1352
```

<210> SEQ ID NO 32
<211> LENGTH: 496
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 32

```
ggccgcccca cgtgcgcagc aggacgcagc gctgcctgaa actcgcgccg cgaggagagg    60
gcggggccgc ggaaaggaaa gggggggggct gggaggcccg gaggggggctg ggccggggac   120
ccgggagggg tcgggacggg gcgggggtccg cgcggaggag gcggagctgg aaggtgaagg   180
ggcaggacgg gtgcccgggt ccccagtccc tccgccacgt ggggagcgcg gtcctgggcg   240
tctgtgcccg cgaatccact gggagcccgg cctggccccg acagcgcagc tgctccgggc   300
```

```
ggacccgggg gtctgggccg cgcttccccg cccgcgcgcc gctcgcgctc ccagggtgca    360
gggacgccag cgagggcccc agcggagaga ggtcgaatcg gcctaggctg tggggtaacc    420
cgagggaggg gcctctagat ataagggcga attccagcac actggcggcc gttactagtg    480
gatccgagct cggtac                                                    496
```

<210> SEQ ID NO 33
<211> LENGTH: 857
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33

```
ttatgtcaca ccacagaagt aaggttcctt cacaaagatc ccaagctgtc gatcgacatt     60
tctagaggat ctcggacccg ggaatcccc gtcccccaac atgtccagat cgaaatcgtc    120
tagcgcgtcg gcatgcgcca tcgccacgtc ctcgccgtct aagtggagct cgtccccag    180 gctgacatcg gtcgggggg cggatctcgg acccgggaa tccccgtccc caacatgtc     240 cagatcgaaa tcgtctagcg cgtcggcatg cgccatcgcc acgtcctcgc cgtctaagtg    300
gagctcgtcc cccaggctga catcggtcgg ggggcggat ccccgggct gcaggaattc     360 cggcgataca gtcaactgtc tttgaccttt gttactactc tcttccgatg atgatgtcgc    420
acttattcta tgctgtctca atgttagagg catatcagtc tccactgaag ccaatctatc    480
tgtgacggca tctttattca cattatcttg tacaaataat cctgttaaca atgcttttat    540
atcctgtaaa gaatccattt tcaaaatcat gtcaaggtct tctcgaggaa aaatcagtag    600
aaatagctgt tccagtcttt ctagccttga ttccacttct gtcagatgtg ccctagtcag    660
cggagacctt ttggttttgg gagagtagcg acactcccag ttgttcttca gacacttggc    720
gcacttcggt ttttctttgg agcacttgag ctttttaagt cggcaaatat cgcatgcttg    780
ttcgatagaa gacagtagct tcatctttca ggaggctagg gccgccagtg tgatggatat    840
ctgcagaatt cgcccctt                                                  857
```

<210> SEQ ID NO 34
<211> LENGTH: 8512
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34

```
ggtacgggag gtacttggag cggccgcgat ccagacatga taagatacat tgatgagttt     60
ggacaaacca caactagaat gcagtgaaaa aaatgcttta tttgtgaaat tgtgatgct     120 attgctttat ttgtaaccat tataagctgc aataaacaag ttaacaacaa caattgcatt    180 catttatgt ttcaggttca gggggaggtg tgggaggttt tttaaagcaa gtaaaacctc     240
tacaaatgtg gtatggctga ttatgatcat gaacagactg tgaggactga ggggcctgaa    300
atgagccttg ggactgtgaa tttaaaatac acaaacaatt agaatcagta gtttaacaca    360
ttatacactt aaaattttta tatttacctt agagctttaa atctctgtag gtagtttgtc    420
caattatgtc acaccacaga agtaaggttc cttcacaaag atcccaagct gtcgatcgac    480
atttctagag gatctcggac ccggggaatc ccgtcccc aacatgtcca gatcgaaatc     540
gtctagcgcg tcggcatgcg ccatcgccac gtcctcgccc tctaagtgga gctcgtcccc    600
```

```
caggctgaca tcggtcgggg gggcggatct cggacccggg gaatcccgt ccccaacat      660
gtccagatcg aaatcgtcta gcgcgtcggc atgcgccatc gccacgtcct cgccgtctaa    720
gtggagctcg tcccccaggc tgacatcggt cggggggcg gatccccgg gctgcaggaa     780
ttccggcgat acagtcaact gtctttgacc tttgttacta ctctcttccg atgatgatgt    840
cgcacttatt ctatgctgtc tcaatgttag aggcatatca gtctccactg aagccaatct   900
atctgtgacg gcatctttat tcacattatc ttgtacaaat aatcctgtta caatgctttt   960
tatatcctgt aaagaatcca ttttcaaaat catgtcaagg tcttctcgag gaaaaatcag  1020
tagaaatagc tgttccagtc tttctagcct tgattccact tctgtcagat gtgccctagt   1080
cagcggagac cttttggttt tgggagagta gcgacactcc cagttgttct tcagacactt   1140
ggcgcacttc ggttttctt tggagcactt gagcttttta agtcggcaaa tatcgcatgc   1200
ttgttcgata aagacagta gcttcatctt tcaggaggct agggccgcca gtgtgatgga   1260
tatctgcaga attcgccctt ccttgcctgc tgctttccac caagtgctgg agagctggtg  1320
aattgctcac tcccggctca ttcctctaat gaccgaagcg tctcgcagat gcaacctgcc  1380
gtggaggagc agggagggag tgatttccag gtgtgggctt tttcagccat tcctaaaggc  1440
gacttgagtt caccctcactc actccagcat ttgtactcct gttgtggaaa aggcagtgag 1500
cacaagccaa gcccgctcca ccttcacccc gccccacctc ccccggccct ttcctgggcc  1560
agtcttaggg ccctgagtac agacagcctg gctacccgtt aaccattctc agcgtgtggc  1620
tgcttttac acacatgtgt acatatgcac ggacacacac acacacacag aggcttcccc   1680
agtactcctc tatataggaa cccgtcacca tcccagacat atgcagaaga aagcccaaac  1740
cggctgtgtg agacaggaac aattaacacg gtaacagatc cgataatgca gaccatcagg  1800
cctaaagaac acggagggac tgtgttctac ctccttatag aaaagcaatt agtgcctttt  1860
tagctttgga accatgcccg gtggtgtgtg tgtggacaga actgctggct ggttgttaag  1920
ttgctactaa acacagtgtt gtttctcgtg gtctctgccc ttgttaacta ggattgaggc  1980
acttttgaac ataggtacct gggtcctaag ggcgaattcc agcacactgg cggccgttac  2040
tagtggatcc gagctcggta ccaagctcca gctgggaata gagataggag gggacccagc  2100
tggatgcagt gggcagtggg ggtcatagag tcaagagggt acagaataca atggggtcct  2160
agtatcatgg tggaggtcag aaagagccct aaaagagagg gtcaaggtag gaggttagtg  2220
aaggtccacc tccaccctct ccaggacagg gacatcaggc cacaattaat ttctctgcag  2280
ttggtgagtg gtcatggtct ctggagtccc cagcatccag agtgtccctg gtctagtggt  2340
cccccctttc tgagccacag ccactttctc catcaaatga ggccagtaat acccatccca  2400
tagtgatgct gtgaggatga gatgagcatc tgtaagtgct gaagataatc cctgacacat  2460
cccaagcatt cagcagtgca agcatacact tacacggcac tccccagagc caggcatgtg  2520
ctggtgcctc atacacgtga ccacatttga tcgtcacaat gaccctgtga gggagactgt  2580
gcaacagagg actgaccttg ctcaaagacc tcaggcgttt cccctcagag cctgagaggt   2640
catctctttt tttttttttt ttcctttct ttcttttct tttccattc ttttctttg      2700
caagaggtca tctctaatgc tttggaatat cctgccagat tagagtccct tgttcacct    2760
gaaggtttgg gccacaccag atagtctaac ggtgtgattt tgctgaagg tttttgagcca   2820
cactatatca gctagatttc tagagcggcc ggccgcaata aaatatcttt attttcatta  2880
catctgtgtg ttggtttttt gtgtgaatcg atagtactaa catacgctct ccatcaaaac  2940
aaaacgaaac aaaacaaact agcaaaatag gctgtcccca gtgcaagtgc aggtgccaga  3000
```

```
acatttctct atcgataggt accgagctca tttaggtgac actatagaat acaagcttgc    3060
atgcctgcag gtccggagga cagtactccg ctcggaggac agtactccgc tcggaggaca    3120
gtactccgct cggaggacag tactccgctc ggaggacagt actccgactc tagaggatcc    3180
ccagtcctat atatactcgc tctgcacttg gcccttttt  acactgtgac tgattgagct    3240
ggtgccgtgt cgagtggtgt ctcgagatct gcgatctaag taagcttggc attccggtac    3300
tgttggtaaa gccaccatgg aagacgccaa aaacataaag aaaggcccgg cgccattcta    3360
tccgctggaa gatggaaccg ctggagagca actgcataag gctatgaaga gatacgccct    3420
ggttcctgga acaattgctt ttacagatgc acatatcgag gtggacatca cttacgctga    3480
gtacttcgaa atgtccgttc ggttggcaga agctatgaaa cgatatgggc tgaatacaaa    3540
tcacagaatc gtcgtatgca gtgaaaactc tcttcaattc tttatgccgg tgttgggcgc    3600
gttatttatc ggagttgcag ttgcgcccgc gaacgacatt tataatgaac gtgaattgct    3660
caacagtatg ggcatttcgc agcctaccgt ggtgttcgtt tccaaaaagg ggttgcaaaa    3720
aattttgaac gtgcaaaaaa agctcccaat catccaaaaa attattatca tggattctaa    3780
aacggattac cagggatttc agtcgatgta cacgttcgtc acatctcatc tacctcccgg    3840
ttttaatgaa tacgattttg tgccagagtc cttcgatagg gacaagacaa ttgcactgat    3900
catgaactcc tctggatcta ctggtctgcc taaaggtgtc gctctgcctc atagaactgc    3960
ctgcgtgaga ttctcgcatg ccagagatcc tatttttggc aatcaaatca ttccggatac    4020
tgcgatttta agtgttgttc cattccatca cggttttgga atgtttacta cactcggata    4080
tttgatatgt ggatttcgag tcgtcttaat gtatagattt gaagaagagc tgtttctgag    4140
gagccttcag gattacaaga ttcaaagtgc gctgctggtg ccaaccctat tctccttctt    4200
cgccaaaagc actctgattg acaaatacga tttatctaat ttacacgaaa ttgcttctgg    4260
tggcgctccc ctctctaagg aagtcgggga agcggttgcc aagaggttcc atctgccagg    4320
tatcaggcaa ggatatgggc tcactgagac tacatcagct attctgatta cacccgaggg    4380
ggatgataaa ccgggcgcgg tcggtaaagt tgttccattt tttgaagcga aggttgtgga    4440
tctggatacc gggaaaacgc tgggcgttaa tcaaagaggc gaactgtgtg tgagaggtcc    4500
tatgattatg tccggttatg taaacaatcc ggaagcgacc aacgccttga ttgacaagga    4560
tggatggcta cattctggag acatagctta ctgggacgaa gacgaacact tcttcatcgt    4620
tgaccgcctg aagtctctga ttaagtacaa aggctatcag gtggctcccg ctgaattgga    4680
atccatcttg ctccaacacc ccaacatctt cgacgcaggt gtcgcaggtc ttcccgacga    4740
tgacgccggt gaacttcccg ccgccgttgt tgttttggag cacggaaaga cgatgacgga    4800
aaaagagatc gtggattacg tcgccagtca agtaacaacc gcgaaaaagt tgcgcggagg    4860
agttgtgttt gtggacgaag taccgaaagg tcttaccgga aaactcgacg caagaaaaat    4920
cagagagatc ctcataaagg ccaagaaggg cggaaagatc gccgtgtaat ctaggtacc    4980
gagctcttac gcgtgctagc cctcgacaat caacctctgg attacaaaat ttgtgaaaga    5040
ttgactggta ttcttaacta tgttgctcct tttacgctat gtggatacgc tgctttaatg    5100
cctttgtatc atgctattgc ttcccgtatg gctttcattt tctcctcctt gtataaatcc    5160
tggttgctgt ctctttatga ggagttgtgg cccgttgtca gcaacgtgg  cgtggtgtgc    5220
actgtgtttg ctgacgcaac ccccactggt tggggcattg ccaccacctg tcagctcctt    5280
tccgggactt tcgctttccc cctccctatt gccacggcgg aactcatcgc cgcctgcctt    5340
gcccgctgct ggacaggggc tcggctgttg ggcactgaca attccgtggt gttgtcgggg    5400
```

```
aagctgacgt cctttccatg gctgctcgcc tgtgttgcca cctggattct gcgcgggacg    5460
tccttctgct acgtcccttc ggccctcaat ccagcggacc ttccttcccg cggcctgctg    5520
ccggctctgc ggcctcttcc gcgtcttcgc cttcgccctc agacgagtcg gatctccctt    5580
tgggccgcct ccccgcctgg aattcgagct cggtacgggc tcgactagag tcgggcggc     5640
cggccgcttc gagcagacat gataagatac attgatgagt ttggacaaac cacaactaga    5700
atgcagtgaa aaaatgctt tatttgtgaa atttgtgatg ctattgcttt atttgtaacc     5760
attataagct gcaataaaca agttaacaac aacaattgca ttcattttat gtttcaggtt    5820
caggggagg tgtgggaggt ttttaaagc aagtaaaacc tctacaaatg tggtaaaatc      5880
gataaggatc cgtcgaccga tgcccttgag agccttcaac ccagtcagct ccttccggtg    5940
ggcgcgggc atgactatcg tcgccgcact tatgactgtc ttctttatca tgcaactcgt     6000
aggacaggtg ccggcagcgc tcttccgctt cctcgctcac tgactcgctg cgctcggtcg    6060
ttcggctgcg gcgagcggta tcagctcact caaaggcggt aatacggtta ccacagaat    6120
caggggataa cgcaggaaag aacatgtgag caaaaggcca gcaaaggcc aggaaccgta    6180
aaaaggccgc gttgctggcg ttttttccata ggctccgccc ccctgacgag catcacaaaa   6240
atcgacgctc aagtcagagg tggcgaaacc cgacaggact ataaagatac caggcgtttc   6300
cccctggaag ctccctcgtg cgctctcctg ttccgaccct gccgcttacc ggatacctgt    6360
ccgcctttct cccttcggga agcgtggcgc tttctcaatg ctcacgctgt aggtatctca    6420
gttcggtgta ggtcgttcgc tccaagctgg gctgtgtgca cgaaccccc gttcagcccg     6480
accgctgcgc cttatccggt aactatcgtc ttgagtccaa cccggtaaga cacgacttat    6540
cgccactggc agcagccact ggtaacagga ttagcagagc gaggtatgta ggcggtgcta    6600
cagagttctt gaagtggtgg cctaactacg gctacactag aaggacagta tttggtatct    6660
gcgctctgct gaagccagtt accttcggaa aaagagttgg tagctcttga tccggcaaac    6720
aaaccaccgc tggtagcggt ggtttttttg tttgcaagca gcagattacg cgcagaaaaa   6780
aaggatctca agaagatcct ttgatctttt ctacggggtc tgacgctcag tggaacgaaa    6840
actcacgtta agggattttg gtcatgagat tatcaaaaag gatcttcacc tagatccttt    6900
taaattaaaa atgaagtttt aaatcaatct aaagtatata tgagtaaact tggtctgaca    6960
gttaccaatg cttaatcagt gaggcaccta tctcagcgat ctgtctattt cgttcatcca    7020
tagttgcctg actccccgtc gtgtagataa ctacgatacg ggagggctta ccatctggcc    7080
ccagtgctgc aatgataccg cgagacccac gctcaccggc tccagattta tcagcaataa    7140
accagccagc cggaagggcc gagcgcagaa gtggtcctgc aactttatcc gcctccatcc    7200
agtctattaa ttgttgccgg gaagctagag taagtagttc gccagttaat agtttgcgca    7260
acgttgttgc cattgctaca ggcatcgtgg tgtcacgctc gtcgtttggt atggcttcat    7320
tcagctccgg ttcccaacga tcaaggcgag ttacatgatc cccatgttg tgcaaaaaag    7380
cggttagctc cttcggtcct ccgatcgttg tcagaagtaa gttggccgca gtgttatcac    7440
tcatggttat ggcagcactg cataattctc ttactgtcat gccatccgta agatgctttt    7500
ctgtgactgg tgagtactca accaagtcat tctgagaata gtgtatgcgg cgaccgagtt    7560
gctcttgccc ggcgtcaata cgggataata ccgcgccaca tagcagaact ttaaaagtgc    7620
tcatcattgg aaaacgttct cggggcgaa aactctcaag gatcttaccg ctgttgagat    7680
ccagttcgat gtaaccccact cgtgcaccca actgatcttc agcatctttt actttcacca    7740
gcgtttctgg gtgagcaaaa acaggaaggc aaaatgccgc aaaaaaggga ataagggcga    7800
```

-continued

| | |
|---|---|
| cacggaaatg ttgaatactc atactcttcc tttttcaata ttattgaagc atttatcagg | 7860 |
| gttattgtct catgagcgga tacatatttg aatgtattta gaaaaataaa caaatagggg | 7920 |
| ttccgcgcac atttccccga aaagtgccac ctgacgcgcc ctgtagcggc gcattaagcg | 7980 |
| cggcgggtgt ggtggttacg cgcagcgtga ccgctacact tgccagcgcc ctagcgcccg | 8040 |
| ctcctttcgc tttcttccct tcctttctcg ccacgttcgc cggctttccc cgtcaagctc | 8100 |
| taaatcgggg ctcccttta gggttccgat ttagtgcttt acggcacctc gaccccaaaa | 8160 |
| aacttgatta gggtgatggt tcacgtagtg gccatcgcc ctgatagacg gttttcgcc | 8220 |
| ctttgacgtt ggagtccacg ttctttaata gtggactctt gttccaaact ggaacaacac | 8280 |
| tcaaccctat ctcggtctat tcttttgatt tataagggat tttgccgatt tcggcctatt | 8340 |
| ggttaaaaaa tgagctgatt taacaaaaat ttaacgcgaa ttttaacaaa atattaacgt | 8400 |
| ttacaatttc ccattcgcca ttcaggctgc gcaactgttg ggaagggcga tcggtgcggg | 8460 |
| cctcttcgct attacgccag cccaagctac catgataagt aagtaatatt aa | 8512 |

<210> SEQ ID NO 35
<211> LENGTH: 8565
<212> TYPE: DNA
<213> ORGANISM: Artificial Sequence
<220> FEATURE:
<223> OTHER INFORMATION: Description of Artificial Sequence: Synthetic Primer

<400> SEQUENCE: 35

| | |
|---|---|
| cgccattcag gctgcgcaac tgttgggaag ggcgatcggt gcgggcctct tcgctattac | 60 |
| gccagcccaa gctaccatga taagtaagta atattaaggt acgggaggta cttggagcgg | 120 |
| ccgcgatcca gacatgataa gatacattga tgagtttgga caaccacaa ctagaatgca | 180 |
| gtgaaaaaaa tgctttattt gtgaaatttg tgatgctatt gctttatttg taaccattat | 240 |
| aagctgcaat aaacaagtta acaacaacaa ttgcattcat tttatgtttc aggttcaggg | 300 |
| ggaggtgtgg gaggtttttt aaagcaagta aaacctctac aaatgtggta tggctgatta | 360 |
| tgatcatgaa cagactgtga ggactgaggg gcctgaaatg agccttggga ctgtgaattt | 420 |
| aaaatacaca aacaattaga atcagtagtt taacacatta tacacttaaa aattttatat | 480 |
| ttaccttaga gctttaaatc tctgtaggta gtttgtccaa ttatgtcaca ccacagaagt | 540 |
| aaggttcctt cacaaagatc ccaagctgtc gatcgacatt tctagaggat ctcggacccg | 600 |
| gggaatcccc gtccccaac atgtccagat cgaaatcgtc tagcgcgtcg gcatgcgcca | 660 |
| tcgccacgtc ctcgccgtct aagtggagct cgtccccag gctgacatcg gtcgggggg | 720 |
| cggatctcgg acccgggaa tccccgtccc ccaacatgtc cagatcgaaa tcgtctagcg | 780 |
| cgtcggcatg cgccatcgcc acgtcctcgc cgtctaagtg gagctcgtcc cccaggctga | 840 |
| catcggtcgg ggggcggat ccccggggct gcaggaattc cggcgataca gtcaactgtc | 900 |
| tttgaccttt gttactactc tcttccgatg atgatgtcgc acttattcta tgctgtctca | 960 |
| atgttagagg catatcagtc tccactgaag ccaatctatc tgtgacggca tctttattca | 1020 |
| cattatcttg tacaaataat cctgttaaca atgcttttat atcctgtaaa gaatccattt | 1080 |
| tcaaaatcat gtcaaggtct ctcgaggaa aaatcagtag aaatagctgt tccagtcttt | 1140 |
| ctagccttga ttccacttct gtcagatgtg ccctagtcag cggagacctt ttggttttgg | 1200 |
| gagagtagcg acactcccag ttgttcttca gacacttggc gcacttcggt ttttctttgg | 1260 |
| agcacttgag cttttaagt cggcaaatat cgcatgcttg ttcgtagaa gacagtagct | 1320 |
| tcatcttca ggaggctagg gccgccccac gtgcgcagca ggacgcagcg ctgcctgaaa | 1380 |

```
ctcgcgccgc gaggagaggg cggggccgcg gaaaggaaag ggggggggctg ggaggcccgg    1440 aggggggctgg gccgggggacc cgggaggggt cgggacgggg cggggtccgc gcggaggagg   1500
cggagctgga aggtgaaggg gcaggacggg tgcccgggtc cccagtccct ccgccacgtg    1560
gggagcgcgg tcctgggcgt ctgtgcccgc gaatccactg ggagcccggc ctggccccga    1620
cagcgcagct gctccgggcg gacccggggg tctgggccgc gcttccccgc ccgcgcgccg    1680
ctcgcgctcc cagggtgcag ggacgccagc gagggcccca gcggagagag gtcgaatcgg    1740
cctaggctgt ggggtaaccc gagggagggg cctctagata taagggcgaa ttccagcaca    1800
ctggcggccg ttactagtgg atccgagctc ggtacacaga cattgacatt gtgtcatcta    1860
gtatacaaat aggttcttgg agtactttac taggcatgga caatgcccaa tgcctgtccc    1920
attcttcagg catatttta tttgtgggct ttatgtccct attaagaaaa agactaagaa     1980
caagatgcta tcatattttc ttaactggaa tggtagatgt ttaaacatga tgactaccaa    2040
gcttggctag aacattgtgt catctagtat acaaataggt tcttggagta ctttactagg    2100
catggacaat gcccaatgcc tgtcccattc ttcaggcata tttttatttg tgggctttat    2160
gtccctatta agaaaagac taagaacaag atgctatcat aagctccaag cttatcgcca    2220
gctgggaata gagataggag gggacccagc tggatgcagt gggcagtggg ggtcatagag    2280
tcaagagggt acagaataca atgggtcct agtatcatgg tggaggtcag aaagagccct    2340
aaaagagagg gtcaaggtag gaggttagtg aaggtccacc tccaccctct ccaggacagg    2400
gacatcaggc cacaattaat ttctctgcag ttggtgagtg gtcatggtct ctggagtccc    2460
cagcatccag agtgtccctg gtctagtggt ccccccttc tgagccacag ccactttctc     2520
catcaaatga ggccagtaat acccatccca tagtgatgct gtgaggatga atgagcatc    2580 tgtaagtgct gaagataatc cctgacacat cccaagcatt cagcagtgca agcatacact    2640
tacacggcac tccccagagc caggcatgtg ctggtgcctc atacacgtga ccacatttga    2700
tcgtcacaat gaccctgtga gggagactgt gcaacagagg actgaccttg ctcaaagacc    2760
tcaggcgttt cccctcagag cctgagaggt catctctttt tttttttttt tttcctttct    2820 ttcttttct tttccatttc ttttcttg caagaggtca tctctaatgc tttggaatat      2880
cctgccagat tagagtccct tgttcacct gaaggtttgg gccacaccag atagtctaac    2940
ggtgtgattt gtgctgaagg ttttgagcca cactatatca gctagatttc tagagcggcc    3000
ggccgcaata aaatatcttt attttcatta catctgtgtg ttggtttttt gtgtgaatcg    3060
atagtactaa catacgctct ccatcaaaac aaaacgaaac aaaacaaact agcaaaatag    3120
gctgtcccca gtgcaagtgc aggtgccaga acatttctct atcgataggt accgagctca    3180
tttaggtgac actatagaat acaagcttgc atgcctgcag gtccggagga cagtactccg    3240
ctcggaggac agtactccgc tcggaggaca gtactccgct cggaggacag tactccgctc    3300
ggaggacagt actccgactc tagaggatcc ccagtcctat atatactcgc tctgcacttg    3360 gcccttttt acactgtgac tgattgagct ggtgccgtgt cgagtggtgt ctcgagatct    3420
gcgatctaag taagcttggc attccggtac tgttggtaaa gccaccatgg aagacgccaa    3480
aaacataaag aaaggcccgg cgccattcta tccgctggaa gatggaaccg ctggagagca    3540
actgcataag gctatgaaga gatacgccct ggttcctgga caattgcttt tacagatgc    3600 acatatcgag gtggacatca cttacgctga gtacttcgaa atgtccgttc ggttggcaga    3660
agctatgaaa cgatatgggc tgaatacaaa tcacagaatc gtcgtatgca gtgaaaactc    3720
tcttcaattc tttatgccgg tgttgggcgc gttatttatc ggagttgcag ttgcgcccgc    3780
```

```
gaacgacatt tataatgaac gtgaattgct caacagtatg ggcatttcgc agcctaccgt    3840
ggtgttcgtt tccaaaaagg ggttgcaaaa aattttgaac gtgcaaaaaa agctcccaat    3900
catccaaaaa attattatca tggattctaa aacggattac cagggatttc agtcgatgta    3960
cacgttcgtc acatctcatc tacctcccgg ttttaatgaa tacgattttg tgccagagtc    4020
cttcgatagg gacaagacaa ttgcactgat catgaactcc tctggatcta ctggtctgcc    4080
taaaggtgtc gctctgcctc atagaactgc ctgcgtgaga ttctcgcatg ccagagatcc    4140 tattttttggc aatcaaatca ttccggatac tgcgatttta agtgttgttc cattccatca    4200
cggttttgga atgtttacta cactcggata tttgatatgt ggatttcgag tcgtcttaat    4260
gtatagattt gaagaagagc tgtttctgag gagccttcag gattacaaga ttcaaagtgc    4320
gctgctggtg ccaaccctat tctccttctt cgccaaaagc actctgattg acaaatacga    4380
tttatctaat ttacacgaaa ttgcttctgg tggcgctccc ctctctaagg aagtcgggga    4440
agcggttgcc aagaggttcc atctgccagg tatcaggcaa ggatatgggc tcactgagac    4500
tacatcagct attctgatta cacccgaggg ggatgataaa ccgggcgcgg tcggtaaagt    4560
tgttccattt tttgaagcga aggttgtgga tctggatacc gggaaaacgc tgggcgttaa    4620
tcaaagaggc gaactgtgtg tgagaggtcc tatgattatg tccggttatg taaacaatcc    4680
ggaagcgacc aacgccttga ttgacaagga tggatggcta cattctggag acatagctta    4740
ctgggacgaa gacgaacact tcttcatcgt tgaccgcctg aagtctctga ttaagtacaa    4800
aggctatcag gtggctcccg ctgaattgga atccatcttg ctccaacacc ccaacatctt    4860
cgacgcaggt gtcgcaggtc ttcccgacga tgacgccggt gaacttcccg ccgccgttgt    4920
tgttttggag cacggaaaga cgatgacgga aaaagagatc gtggattacg tcgccagtca    4980
agtaacaacc gcgaaaaagt tgcgcggagg agttgtgttt gtggacgaag taccgaaagg    5040
tcttaccgga aaactcgacg caagaaaaat cagagagatc ctcataaagg ccaagaaggg    5100
cggaaagatc gccgtgtaat tctaggtacc gagctcttac gcgtgctagc cctcgacaat    5160
caacctctgg attacaaaat ttgtgaaaga ttgactggta ttcttaacta tgttgctcct    5220
tttacgctat gtggatacgc tgctttaatg cctttgtatc atgctattgc ttcccgtatg    5280
gctttcattt tctcctcctt gtataaatcc tggttgctgt ctctttatga ggagttgtgg    5340
cccgttgtca ggcaacgtgg cgtggtgtgc actgtgtttg ctgacgcaac ccccactggt    5400
tggggcattg ccaccacctg tcagctcctt tccgggactt tcgctttccc cctccctatt    5460
gccacggcgg aactcatcgc cgcctgcctt gcccgctgct ggacagggc tcggctgttg    5520 ggcactgaca attccgtggt gttgtcgggg aagctgacgt cctttccatg gctgctcgcc    5580
tgtgttgcca cctggattct gcgcgggacg tccttctgct acgtcccttc ggccctcaat    5640
ccagcggacc ttccttcccg cggcctgctg ccggctctgc ggcctcttcc gcgtcttcgc    5700
cttcgccctc agacgagtcg gatctccctt ggggccgcct ccccgcctgg aattcgagct    5760
cggtacgggc tcgactagag tcggggcggc cggccgcttc gagcagacat gataagatac    5820
attgatgagt ttggacaaac cacaactaga atgcagtgaa aaaaatgctt tatttgtgaa    5880
atttgtgatg ctattgcttt atttgtaacc attataagct gcaataaaca agttaacaac    5940
aacaattgca ttcattttat gtttcaggtt cagggggagg tgtgggaggt tttttaaagc    6000
aagtaaaacc tctacaaatg tggtaaaatc gataaggatc cgtcgaccga tgcccttgag    6060
agccttcaac ccagtcagct ccttccggtg ggcgcgggga tgactatcg tcgccgcact    6120 tatgactgtc ttctttatca tgcaactcgt aggacaggtg ccggcagcgc tcttccgctt    6180
```

```
cctcgctcac tgactcgctg cgctcggtcg ttcggctgcg gcgagcgta tcagctcact    6240 caaaggcggt aatacggtta tccacagaat caggggataa cgcaggaaag aacatgtgag    6300
caaaaggcca gcaaaaggcc aggaaccgta aaaaggccgc gttgctggcg ttttttccata   6360 ggctccgccc ccctgacgag catcacaaaa atcgacgctc aagtcagagg tggcgaaacc    6420
cgacaggact ataaagatac caggcgtttc ccctggaag ctcccttgtg cgctctcctg    6480
ttccgaccct gccgcttacc ggatacctgt ccgcctttct cccttcggga agcgtggcgc    6540
tttctcaatg ctcacgctgt aggtatctca gttcggtgta ggtcgttcgc tccaagctgg    6600
gctgtgtgca cgaaccccc gttcagcccg accgctgcgc cttatccggt aactatcgtc    6660
ttgagtccaa cccggtaaga cacgacttat cgccactggc agcagccact ggtaacagga    6720
ttagcagagc gaggtatgta ggcggtgcta cagagttctt gaagtggtgg cctaactacg    6780
gctacactag aaggacagta tttggtatct gcgctctgct gaagccagtt accttcggaa    6840
aaagagttgg tagctcttga tccggcaaac aaaccaccgc tggtagcggt ggtttttttg    6900
tttgcaagca gcagattacg cgcagaaaaa aaggatctca agaagatcct ttgatctttt    6960
ctacggggtc tgacgctcag tggaacgaaa actcacgtta agggattttg gtcatgagat    7020
tatcaaaaag gatcttcacc tagatccttt taaattaaaa atgaagtttt aaatcaatct    7080
aaagtatata tgagtaaact tggtctgaca gttaccaatg cttaatcagt gaggcaccta    7140
tctcagcgat ctgtctattt cgttcatcca tagttgcctg actccccgtc gtgtagataa    7200
ctacgatacg ggagggctta ccatctggcc ccagtgctgc aatgataccg cgagacccac    7260
gctcaccggc tccagattta tcagcaataa accagccagc cggaagggcc gagcgcagaa    7320
gtggtcctgc aactttatcc gcctccatcc agtctattaa ttgttgccgg gaagctagag    7380
taagtagttc gccagttaat agtttgcgca acgttgttgc cattgctaca ggcatcgtgg    7440
tgtcacgctc gtcgtttggt atggcttcat tcagctccgg ttcccaacga tcaaggcgag    7500
ttacatgatc ccccatgttg tgcaaaaaag cggttagctc cttcggtcct ccgatcgttg    7560
tcagaagtaa gttggccgca gtgttatcac tcatggttat ggcagcactg cataattctc    7620
ttactgtcat gccatccgta agatgctttt ctgtgactgg tgagtactca accaagtcat    7680
tctgagaata gtgtatgcgg cgaccgagtt gctcttgccc ggcgtcaata cgggataata    7740
ccgcgccaca tagcagaact ttaaaagtgc tcatcattgg aaaacgttct cggggcgaa    7800 aactctcaag gatcttaccg ctgttgagat ccagttcgat gtaacccact cgtgcaccca    7860
actgatcttc agcatctttt actttcacca gcgtttctgg gtgagcaaaa acaggaaggc    7920
aaaatgccgc aaaaaaggga ataagggcga cacggaaatg ttgaatactc atactcttcc    7980
tttttcaata ttattgaagc atttatcagg gttattgtct catgagcgga tacatatttg    8040
aatgtattta gaaaaataaa caaataggg ttccgcgcac atttccccga aaagtgccac    8100
ctgacgcgcc ctgtagcggc gcattaagcg cggcgggtgt ggtggttacg cgcagcgtga    8160
ccgctacact tgccagcgcc ctagcgcccg ctcctttcgc tttcttccct tcctttctcg    8220
ccacgttcgc cggctttccc cgtcaagctc taaatcgggg gctcccttta gggttccgat    8280
ttagtgcttt acggcacctc gaccccaaaa aacttgatta gggtgatggt tcacgtagtg    8340
ggccatcgcc ctgatagacg ttttttcgcc ctttgacgtt ggagtccacg ttctttaata    8400
gtggactctt gttccaaact ggaacaacac tcaaccctat ctcggtctat tcttttgatt    8460
tataagggat tttgccgatt tcggcctatt ggttaaaaaa tgagctgatt taacaaaaat    8520
ttaacgcgaa ttttaacaaa atattaacgt ttacaatttc ccatt                   8565
```

<210> SEQ ID NO 36
<211> LENGTH: 279
<212> TYPE: DNA
<213> ORGANISM: Artificial Sequence
<220> FEATURE:
<223> OTHER INFORMATION: Description of Artificial Sequence: Synthetic
       Primer

<400> SEQUENCE: 36
gacactatag aatacaagct tgcatgcctg caggtccgga ggacagtact ccgctcggag    60
gacagtactc cgctcggagg acagtactcc gctcggagga cagtactccg ctcggaggac   120
agtactccga ctctagagga tccccagtcc tatatatact cgctctgcac ttggcccttt   180
tttacactgt gactgattga gctggtgccg tgtcgagtgg tgtctcgaga tctgcgatct   240
aagtaagctt ggcattccgg tactgttggt aaagccacc                          279

<210> SEQ ID NO 37
<211> LENGTH: 650
<212> TYPE: DNA
<213> ORGANISM: Artificial Sequence
<220> FEATURE:
<223> OTHER INFORMATION: Description of Artificial Sequence: Synthetic
       Primer

<400> SEQUENCE: 37
gctagctacg ggccagatat acgcgttgac attgattatt gactagttat taatagtaat    60
caattacggg gtcattagtt catagcccat atatggagtt ccgcgttaca taacttacgg   120
taaatggccc gcctggctga ccgcccaacg accccgccc attgacgtca ataatgacgt    180
atgttcccat agtaacgcca atagggactt tccattgacg tcaatgggtg gagtatttac   240
ggtaaactgc ccacttggca gtacatcaag tgtatcatat gccaagtacg cccctattg    300 acgtcaatga cggtaaatgg cccgcctggc attatgccca gtacatgacc ttatgggact   360
ttcctacttg gcagtacatc tacgtattag tcatcgctat taccatggtg atgcggtttt   420
ggcagtacat caatgggcgt ggatagcggt ttgactcact cgagagacgg tgagagcgag   480
tcagggattg gctggtctgc ttcgggcggg ctaaaggaag gttcaagtgg agctctccta   540
accgacgcgc gtctgtggag aagcggcttg gtcggggtg gtctcgtggg gtcctgcctg   600
tttagtcgct ttcagggttc ttgagcccct tcacgaccgt caccaagctt              650

<210> SEQ ID NO 38
<211> LENGTH: 701
<212> TYPE: DNA
<213> ORGANISM: Artificial Sequence
<220> FEATURE:
<223> OTHER INFORMATION: Description of Artificial Sequence: Synthetic
       Primer

<400> SEQUENCE: 38
gctagctacg ggccagatat acgcgttgac attgattatt gactagttat taatagtaat    60
caattacggg gtcattagtt catagcccat atatggagtt ccgcgttaca taacttacgg   120
taaatggccc gcctggctga ccgcccaacg accccgccc attgacgtca ataatgacgt    180
atgttcccat agtaacgcca atagggactt tccattgacg tcaatgggtg gagtatttac   240
ggtaaactgc ccacttggca gtacatcaag tgtatcatat gccaagtacg cccctattg    300 acgtcaatga cggtaaatgg cccgcctggc attatgccca gtacatgacc ttatgggact   360
ttcctacttg gcagtacatc tacgtattag tcatcgctat taccatggtg atgcggtttt   420

```
ggcagtacat caatgggcgt ggatagcggt ttgactcact cgagcggccg ccagtgtgat    480
ggatatctgc agaattcgcc cttgcgatct gtcagagcac ctcgcgagcg tacgtgcctc    540
aggaagtgac gcacagcccc cctgggggcc gggggcgggg ccaggctata aaccgccggt    600
taggggccgc catcccctca gagcgtcggg atatcgggtg aagggcgaat tccagcacac    660
tggcggccgt tactagtgga tccgagctcg gtaccaagct t                       701
```

ANTITUMOR EFFECT OF MUTANT BIK

This application is a divisional application of U.S. patent application Ser. No. 12/180,730, filed Jul. 28, 2008, now abandoned, which is a continuation of U.S. patent application Ser. No. 10/816,698, filed Apr. 2, 2004, now abandoned, which claims priority to U.S. Provisional Patent Application No. 60/459,901, filed Apr. 2, 2003, all of which are incorporated by reference herein in their entirety.

FIELD OF THE INVENTION

The present invention is directed to the fields of cell biology, molecular biology, cancer biology, and medicine. More particularly, the present invention regards variant forms of Bik comprising anti-cell proliferative and/or pro-apoptotic activities that are useful for cancer therapy.

BACKGROUND OF THE INVENTION

Bik, also known as nbk, is one of the pro-apoptotic BH3-only proteins, which have only one of the Bcl-2 homology regions, BH3 domains, and have recently been recognized as essential initiators of apoptosis (Han et al., 1996; Boyd et al., 1995). Loss of informative alleles on chromosome 22q where the Bik gene is located may be related to the development of human breast and colorectal cancers (Daniel et al., 1999). The 18-kDa Bik protein interacts with E1B 19K and forms heterodimers with various anti-apoptotic proteins, e.g. Bcl-2 and Bcl-XL, the association of which hinders the function of the anti-apoptotic protein (Han et al., 1996). Bik-mediated apoptosis requires BAX (Theodorakis et al., 2002) and is independent of p53 (Han et al., 1996). Bik is also a downstream apoptotic effector of p53 (Bartke et al., 2001) in response to a physiological p53-mediated death stimulus provided by E1A. Elevated Bcl-2 functioned downstream of p53 and Bik induction to inhibit the E1A death pathway, with the ratio of anti-apoptotic Bcl-2 and pro-apoptotic Bik determining cell death or survival in E1A-expressing cells (Mathai et al., 2002). Moreover, Bik can sensitize tumor cells to certain chemotherapeutic agents (Daniel et al., 1999) and one of the chemotherapy drugs, doxorubicin, that induces apoptosis is mediated by Bik gene (Panaretakis et al., 2002). All of these suggest that Bik is a useful therapeutic gene to target human cancer.

BH3-only proteins differ in their expression pattern and mode of activation, and many BH3-only proteins activation needs posttranslational modification (Puthalakath and Strasser, 2002). Bik is one of the BH3-only proteins whose activity can be regulated by phosphorylation (Verma et al., 2000). Verma et al. demonstrated that Bik exists as a phosphoprotein and is phosphorylated at residues threonine 33 and serine 35, which they determined is required for the full apoptotic activity of Bik, possibly by a casein kinase II-related enzyme. That is, Verma et al. mutated the phosphorylation sites at the threonine and serine residues to alanine residues, which reduced the apoptotic activity of Bik. They concluded phosphorylation is required for the pro-apoptotic potency of Bik by a presently unknown mechanism without significantly affecting its affinity for Bcl-2.

BRIEF SUMMARY OF THE INVENTION

The present invention provides novel therapeutic Bik mutant compositions and methods, particularly for cancer, and a skilled artisan recognizes that any additional means in an arsenal to fight cancer is beneficial to public health.

The present invention is directed to a system and method related to mutants of Bik, and particularly to their anti-tumor effects. Bik is a proapoptotic member of the Bcl-2 family of proteins. In the present invention, the inventors demonstrate the novel finding that non-wildtype forms of Bik, such as mutant forms, exerted strong antitumor activity in both in vivo and in vitro systems. In contrast to the teachings of Verma et al. (2000), the exemplary mutant Bik polypeptides described herein similarly abolish phosphorylation sites in Bik yet still comprise potent anti-tumor, anti-cell proliferation, and/or pro-apoptotic activity and, in some embodiments, are more potent than wild-type Bik. That is, the Examples presented herein indicate that the transfection with a polynucleotide encoding a mutant bik polypeptide induces apoptosis in various human cancers. This provides compositions, such as therapeutics, and methods of using same for the present invention, such as the mutant bik polynucleotide in gene therapy for cancer, such as ovarian, breast, pancreatic, and prostate cancer.

Thus, the present invention generally relates to methods for inhibiting proliferation in a cancer cell and/or tumor cell, the method comprising contacting the cell with a mutant Bik polypeptide in an amount effective to inhibit proliferation. The mutant Bik polypeptide referred to herein is a mutant form having anti-cell proliferative, pro-apoptotic, and/or anti-tumor activity. Inhibition of proliferation may be indicated by, for example, an induction of apoptosis of a cell, such as, for example, in cell culture, inhibition of growth of a cancer cell line, reduction in size of a tumor, and/or an increase in survivability, in exemplary embodiments. More preferably, in some embodiments the cell in which proliferation is to be inhibited is a cell in a living organism, for example a human. The inhibition of such transformation has great utility in the prevention and/or treatment of such transformation-driven events as cancer, tumorigenesis, and/or metastasis.

A mutant Bik polypeptide may be contacted with or introduced to a cell through any of a variety of manners known to those of skill. The mutant Bik polypeptide may be introduced through direct introduction of a mutant Bik polypeptide to a cell. In this case, the mutant Bik polypeptide may be obtained through any method known in the art, although it is expected that in vitro production of the mutant Bik polypeptide in a cell, for example in a cell culture system, may be a preferred manner of obtaining mutant Bik.

Mutant Bik may also be introduced to a cell via the introduction of a polynucleotide that encodes the mutant Bik polypeptide to the cell. For example, RNA or DNA encoding Bik may be introduced to the cell by any manner known in the art. In certain preferred embodiments, the mutant Bik is introduced into the cell through the introduction of a DNA segment that encodes mutant Bik. In some such embodiments, it is envisioned that the DNA segment further comprises the mutant Bik gene (or mutant Bik polynucleotide) operatively linked to its associated control sequences. For example, the bik gene may be operatively linked to a suitable promoter and a suitable terminator sequence. The construction of such gene/control sequence DNA constructs is well-known within the art. In particular embodiments, the promoter is selected from the group comprising of CMV, telomerase, TCF-4, or VEGF. However, in particular embodiments, the constructs comprise promoters that are tissue-specific, such as, for example, tissue-specific for cancers including the exemplary breast, prostate, or pancreatic cancers.

In certain embodiments for introduction, the DNA segment may be located on a vector, for example, a plasmid vector or a viral vector. The virus vector may be, for example, selected from the group comprising retrovirus, adenovirus, herpesvirus, vaccina virus, and adeno-associated virus. Such a DNA segment may be used in a variety of methods related to the invention. The vector may be used to deliver a mutant bik gene to a cell in one of the gene-therapy embodiments of the invention. Also, such vectors can be used to transform cultured cells, and such cultured cells could be used, inter alia, for the expression of mutant Bik in vitro.

The present invention is useful for all types of cancer, since mutant Bik, as shown herein in exemplary embodiments, kills cancer cells regardless of their survival tactics adopted by many cancer cells, such as growth factor receptor and AKT pathways. In a particular embodiment, mutant Bik is effective on solid tumors, such as, for example, sarcoma, lung, brain, prostate, breast, ovarian, pancreatic, liver, bladder, gastrointestinal cancers, and hematologic malignancies, such as leukemia, lymphoma, and myeloma. In exemplary embodiments, the present invention is useful for cancers that are estrogen receptor positive, EGF receptor overexpressing, Her2/neu-overexpressing, Her-2/neu-nonoverexpressing, Akt overexpressing, androgen dependent, or angrogen independent. That is, mutant Bik is effective on cancer cells regardless of their status of oncogene overexpression, such as Her-2/neu, EGFR, AKT, or whether their growth is hormone dependent (such as, for example, MCF-7) or not (such as, for example, PC3).

For example, contained herein are specific data showing effectiveness of mutant Bik against cell lines tested from at least six exemplary types of cancers or angiogenic cells, including: 1) breast cancer, such as with MCF-7 (estrogen receptor positive), MDA-MB-468 (EGF receptor overexpressing), and MDA-MB-231; 2) endothelial cell, such as with Human Umbilical Vascular Endothelial Cells (HUVEC) (which shows the anti-angiogenesis effect of mutant Bik; 3) Head and Neck Cancer, such as with TU138 and TU167; 4) Melanoma, such as with B16F10; 5) Ovarian cancer, such as with SKOV-ip1 (Her-2/neu overexpression), SKOV (no Her-2/neu overexpression), and 2774 (Akt overexpression); and 6) Prostate Cancer, such as with PC3 (androgen independent growth).

In particular embodiments, mutant Bik is introduced into a cell that is a human cell. In many embodiments the cell is a tumor cell. In some presently preferred embodiments the tumor cell is a breast tumor cell, a prostrate tumor cell, an ovarian tumor cell, or a pancreatic tumor cell. However, mutant Bik may be introduced into other cells including, but not limited to, a bladder cancer cell, a testicular cancer cell, a colon cancer cell, a skin cancer cell, a lung cancer cell, a stomach cancer cell, an esophageal cancer cell, a brain cancer cell, a leukemia cancer cell, a liver cancer cell, an endometrial cancer cell, or a head and neck cancer cell. In some embodiments, the mutant Bik composition is introduced by injection. In particular embodiments, the mutant Bik composition is comprised in a liposome.

In some embodiments of the present invention, the inventors' discovery that Bik mutants are able to inhibit proliferation will be used in combination with other anti-transformation/anti-cancer therapies. These other therapies may be known at the time of this application, or may become apparent after the date of this application. Bik mutants may be used in combination with other therapeutic polypeptides, polynucleotides encoding other therapeutic polypeptides, chemotherapeutic agents, surgical methods, or radiation, for example. For example, mutant Bik may be used in conjunction with other known polypeptides, such as TNFα or p53. Other polypeptide inducers of apoptosis that may be used in combination with Bik include, but are not limited to, p53, Bax, Bak, Bcl-x, Bad, Bim, Bok, Bid, Harakiri, Ad E1B, Bad and ICE-CED3 proteases.

Mutant Bik may be used in conjunction with any suitable chemotherapeutic agent. In one representative embodiment, the chemotherapeutic agent is taxol. Mutant Bik also may be used in conjunction with radiotherapy. The type of ionizing radiation constituting the radiotherapy may be selected from the group comprising x-rays, γ-rays, and microwaves. In certain embodiments, the ionizing radiation may be delivered by external beam irradiation or by administration of a radionuclide. Mutant Bik also may be used with other gene-therapy regimes. In particular embodiments the mutant Bik is introduced into a tumor. The tumor may be in an animal, in particular, a human.

The Bik mutant gene products and polynucleotides of the present invention may also be introduced using any suitable method. A "suitable method" of introduction is one that places a mutant bik gene product in a position to reduce the proliferation of a tumor cell. For example, injection, oral, and inhalation methods may be employed, with the skilled artisan being able to determine an appropriate method of introduction for a given circumstance. In the embodiments where injection will be used, this injection may be intravenous, intraperitoneal, intramuscular, subcutaneous, intratumoral, intrapleural, or of any other appropriate form.

In certain other aspects of the present invention there are provided therapeutic kits comprising in a suitable container a pharmaceutical formulation of a mutant Bik gene product or a polynucleotide encoding a mutant Bik gene product. Such a kit may further comprise a pharmaceutical formulation of a therapeutic polypeptide, polynucleotide encoding a therapeutic polypeptide, and/or chemotherapeutic agent.

The term "mutant Bik" as used herein refers to a Bik polynucleotide or polypeptide from any organism that comprises such, so long as the mutant Bik comprises anti-tumor activity, anti-cell proliferation activity, and/or pro-apoptotic activity, wherein the mutant Bik comprises at least one altered amino acid compared to native Bik, or the corresponding polynucleotide encoding same. The alteration may comprise a modified amino acid, such as one comprising an additional acetyl group, for example, or the alteration may comprise at least one substituted amino acid on at least one particular amino acid position. In particular embodiments, the mutant Bik will comprise at least one alteration for at least one amino acid, yet retain anti-cell proliferation activity, anti-tumor activity, pro-apoptotic activity, and/or a combination thereof that is useful for the purposes described herein. In some cases, the mutant Bik will exhibit better anti-cell proliferation activity, anti-tumor activity, pro-apoptotic activity, and/or a combination thereof than native Bik. In other circumstances, the mutant Bik may have similar anti-cell proliferation activity, anti-tumor activity, pro-apoptotic activity, and/or a combination thereof to native Bik. In other cases, the mutant Bik may have reduced anti-cell proliferation activity, anti-tumor activity, pro-apoptotic activity, and/or a combination thereof relative to native Bik. Of course, most mutants that comprise one or more relevant activities that are substantially less than the same one or more relevant activities in native Bik or other mutant Biks will likely not be useful in all embodiments of the invention. However, those of skill in the art will, in view of the teachings of the specification and the knowledge of skill in the art, be able to select such mutants that will have utility in certain specific embodiments of the invention.

The anti-tumor activity, anti-cell proliferation activity, and/or pro-apoptotic activity may be useful for an organism other than the one from which the mutant Bik is derived. For example, the human Bik is utilized herein in exemplary embodiments, although a murine Bik may be used alternatively or in addition for human treatment. The mutant Bik from any organism may be altered at any amino acid. Furthermore, the human Bik may be mutated at a particular residue(s) and found useful for therapy, and the mutant murine Bik with its analogous residue(s) substitution may also be effective. In a particular embodiment, the murine Bik polypeptide comprises at least one altered phosphorylation site, and based on the teachings provided herein related to human Bik, one of skill would know how to generate analogous changes in murine Bik. In a further particular embodiment, serine 27, threonine 29, serine 31, and/or a combination thereof are substituted in mutant murine Bik.

Of course, Bik may be mutated for any number of reasons, and one of skill in the art is aware that there may be desirable mutations generated in the Bik polypeptide or a nucleic acid encoding same that are for purposes other than removing phosphorylation sites and/or for effecting or retaining anti-tumor activity, anti-cell proliferation activity, and/or pro-apoptotic activity. For example, mutations may be made to render the Bik polynucleotide and/or polypeptide more amenable for a therapeutic purpose. For example, modifications may be made that reduce antigenicity of the polypeptide, that remove regions of the polypeptide, that enhance nuclear localization of the polypeptide, that increase the half-life of the polypeptide, and so forth.

At least one assay for determining effectiveness of a particular mutant in comparison to wild type is described herein at least in the Examples, and others in the art may be utilized. In particular embodiments, mutants that comprise at least one activity that is substantially less than native Bik are not desirable and are not in the scope of the present invention.

Specifically, the present invention is directed to methods and compositions regarding particular mutant forms of Bik that are associated with control of cell growth, survival or proliferation. In specific embodiments, the control of cell growth is useful in the treatment of cancer or restenosis. Specifically, the present invention teaches a skilled artisan that mutant Bik polypeptides that have one or more amino acid substitutions that result in the polypeptide either not being phosphorylated or being phosphorylated at a lower level are useful for anti-tumor applications. In specific embodiments, the inventors have shown that mutant Bik can reduce or abolish phosphorylation and lead to suppression of growth of transformed cells treated with such mutant Bik. In particular embodiments, substitution with Asp or Glu, for example, results in failure of the polypeptide to be phosphorylated at those sites and leads to suppression of growth of transformed cells upon treatment with such Bik mutants. Of course, the invention is not limited to embodiments in which the amino acid substitution is either Asp or Glu. Rather, any amino acid substitution that prevents phosphorylation of Bik by any amino acid is contemplated within the scope of the invention. In a specific embodiment, the amino acid for substitution at Thr33 and/or Ser35 is not alanine. In another specific embodiment, the at least one amino acid substitution has at least one acidic property, such as, for example, the amino acids aspartate or glutamate. Therefore, an object of the present invention is directed to at least one modification in Bik polypeptide that results in failure of the polypeptide to be phosphorylated, and preferably for that resultant Bik mutant to comprise anti-cell proliferation capability, anti-tumor capability, pro-apoptotic capability, or a combination thereof.

One of skill in the art recognizes that mutations, either to similar amino acids or not, may be made elsewhere in Bik, and that some of these mutants will have the same activities as the exemplary embodiments provided herein. For example, threonine, serine, or other appropriate amino acids anywhere within Bik can be substituted, such as with the exemplary aspartate or glutamate. A skilled artisan is aware of publicly available databases that provide Bik sequences for making alterations different from native Bik, such as the National Center for Biotechnology Information's GenBank database or commercially available databases such as from Celera Genomics, Inc. (Rockville, Md.). Exemplary polypeptide Bik sequences include (as identified by their GenBank Accession numbers): SEQ ID NO:3 (AAC50413; NP_001188; AAF01156; AAC79124; CAA62013; and S58214); and SEQ ID NO:4 (AAC40079 and NP_031572). Exemplary polynucleotide Bik sequences include (as identified by their GenBank Accession numbers): SEQ ID NO:5 (AY245248) and SEQ ID NO:6 (NM_001197).

Thus, the present invention provides guidance regarding different mutations in Bik, and, therefore, the present invention is directed to a novel improvement to the overall arts of cell growth control, including inhibition of cell proliferation and/or facilitation of cell death. In a specific embodiment, the inhibition of a cell proliferation comprises a delay in its rate of proliferation, a delay in its total cell numbers of proliferation, or both.

A skilled artisan recognizes that any site in the Bik polypeptide may be modified to generate such compositions as described, and furthermore that multiple sites may be modified. A skilled artisan is cognizant that a limited number of sites for modification exist in the approximately 160 amino acid Bik polypeptide (depending on the organism). In addition, a skilled artisan recognizes that there are only twenty standard amino acids from which to modify to, and guidance is provided herein directed to methods to generate those modifications. Furthermore, a skilled artisan in the teachings of the present invention knows how to test for anti-tumor, anti-cell growth, and/or pro apoptotic effects, based on the teachings provided herein and other methods in the art, and therefore assaying a particular modification would not subject one skilled in the art to undue experimentation.

Thus, based on the guidance provided herein, the present invention is directed to mutant polypeptides of Bik that result in inhibition of proliferation of a cell or enhancement of cell survival. In specific embodiments, the present invention is directed to mutants including, for example, Bik T33D, S35D, and double mutant T33DS35D.

In accordance with the objects of the present invention, there is as a composition of matter a mutant Bik polypeptide. For example, the composition comprises an amino acid substitution. In a specific embodiment, the substitution prevents phosphorylation of the Bik polypeptide under conditions that would result in phosphorylation of an unsubstituted Bik polypeptide. In other specific embodiments, the substitution is a Thr33 to Asp33 substitution or a Ser35 to Asp35 substitution, or both. In other specific embodiments, the compositions are further defined as compositions in a pharmacologically acceptable excipient in which the Bik polypeptide is dispersed. In additional specific embodiments, the compositions are confined in a suitable container in a kit.

In an additional object of the present invention, there is a method of preventing growth of a cell in an individual comprising the step of administering to the individual a mutant Bik polypeptide. In another specific embodiment, the administration of the polypeptide is by a liposome. In an additional specific embodiment, the polypeptide further comprises a protein transduction domain, such as HIV Tat or penetratin, for example.

In another object of the present invention, there is a method of preventing growth of a cell in an individual comprising the step of administering to the individual a nucleic acid encoding a mutant Bik polypeptide. In another specific embodiment, the administration of the nucleic acid is by a vector selected from the group consisting of a plasmid, a retroviral vector, an adenoviral vector, an adeno-associated viral vector, a liposome, and a combination thereof.

In an additional object of the present invention, there is a method of using a mutant Bik polypeptide composition wherein the Bik polypeptide composition is dispersed in a pharmacologically acceptable excipient, and wherein the composition is administered to an animal having a proliferative cell disorder.

In another object of the present invention, there is a method of treating a proliferative cell disorder in an individual comprising the step of administering to the individual a mutant Bik polypeptide. In another specific embodiment, the proliferative cell disorder is cancer. In a further specific embodiment, the proliferative cell disorder is restenosis. In a further specific embodiment, the cancer is breast cancer, prostate cancer, ovarian cancer, or pancreatic cancer.

In an additional object of the present invention, there is a method of treating a cell comprising contacting the cell with a mutant Bik polypeptide. In a specific embodiment, the cell is a human cell. In another specific embodiment, the cell is comprised in an animal. In a further specific embodiment, the animal is a human. In a further specific embodiment, the human has a proliferative cell disorder. In an additional specific embodiment, the proliferative cell disorder is cancer. In a further specific embodiment, the cancer is breast cancer, ovarian cancer, or prostate cancer. In another specific embodiment, the proliferative cell disorder is restenosis.

In a further object of the invention, a polynucleotide encoding a mutant Bik polypeptide is regulated by a tissue-specific promoter, such as one that targets cancerous tissue. Although any promoter that targets cancerous tissue preferentially over non-cancerous tissue, in a specific embodiment the cancer-specific promoter is a breast cancer specific promoter, a prostate cancer-specific promoter, a or pancreatic-specific promoter, for example.

In a particular embodiment, a breast cancer-specific promoter comprises a breast cancer-specific sequence and, in further embodiments, an enhancer sequence that augments expression, such as the expression level, of the tissue-specific sequence. In a particular embodiment, a CMV promoter enhancer sequence is linked with a breast cancer-specific segment from the exemplary topoisomerase IIα (topII□) promoter or the exemplary transferrin receptor promoter. They are useful for gene targeting to target and treat primary and metastatic breast cancers with less toxicity to normal tissues.

In another embodiment, the expression of a polynucleotide encoding a mutant Bik polypeptide is regulated by a pancreatic-cancer specific promoter. In a particular embodiment, a novel pancreatic cancer specific promoter is utilized, such as one referred to herein as CTP, which is comprised of at least the minimal Cholecystokinin A receptor (CCKAR, −726 to +1 nucleotides), a two-step transcriptional system sequence and the post translational regulatory element of the woodchuck hepatitis virus (WPRE). This engineered construct has a strong promoter activity and demonstrates specificity to pancreatic cancer cells in vitro and in vivo for the expression of mutant Bik.

In another specific embodiment of the present invention, a prostate cancer-specific promoter regulates expression of a polynucleotide that encodes a mutant Bik polypeptide. In a particular embodiment, the invention utilizes a novel prostate cancer specific promoter, such as one referred to herein as ATTP, comprised of at least the minimal human telomerase reverse transcriptase promoter (hTert), the post translational regulatory element of the woodchuck hepatitis virus (WPRE), and an ARR2 control sequence, which is responsive to androgen stimulation. This engineered construct has a strong promoter activity and demonstrates specificity to both androgen-dependent and androgen-independent prostate cancer cells in vitro. This promoter can be used to specifically drive gene expression of mutant Bik in prostate cancer in vivo.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings.

In FIG. 6A, tumor volume was measured and recorded weekly. FIG. 6B shows that BikDD increased the survival rate of mice bearing MDA-MB-231 orthotopic tumors.

FIG. 7A shows tumor volume that was measured and recorded weekly. FIG. 2B shows that BikDD increased the survival rate of mice bearing MDA-MB-231 orthotopic tumors.

FIG. 12A demonstrates that liposome-complexed CT90-BikDD targets breast cancer cells in orthotopic mouse model. In FIGS. 12B and 12D, tumor size record during gene therapy treatment is demonstrated wherein the mice were treated once a week (QW, FIG. 12B) or twice a week (BIW, FIG. 12D).

DETAILED DESCRIPTION OF THE INVENTION

Figure 1:
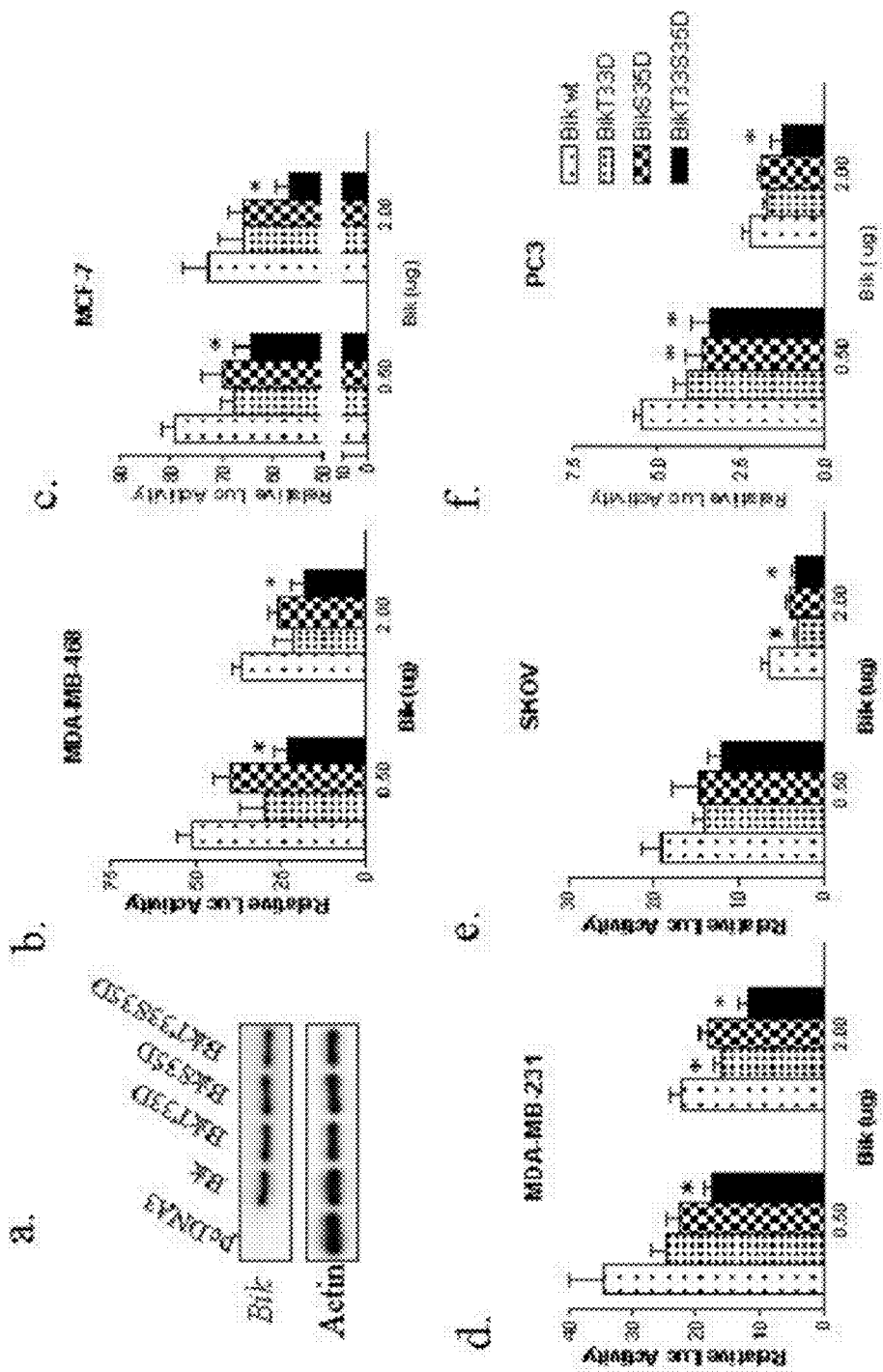
FIGS. 1A through 1F illustrate that the expression of Bik mutants exhibited stronger growth inhibitory effect in different human cancer cell lines.

As used herein the specification, "a" or "an" may mean one or more. As used herein in the claim(s), when used in conjunction with the word "comprising", the words "a" or "an" may mean one or more than one. As used herein "another" may mean at least a second or more.

The present invention regards mutant Bik polypeptides and the nucleic acids that encode them, as well as methods regarding the use of mutant Bik. Thus, in exemplary embodiments, the present inventors changed the residues threonine 33 and serine 35 to aspartate amino acids as potentially constitutive active forms, and these Bik mutants were demonstrated as therapeutic agents in cancer gene therapy. Although the inventors previously demonstrated that systemically administrated nonviral gene delivery system (SN)-bik significantly inhibited the growth and metastasis of human breast cancer cells implanted in nude mice and prolonged the life span of the treated animals (Zou et al., 2002), as described herein Bik mutants could also enhance anti-tumor function of Bik gene product in in vitro and in vivo models, compared to wild type Bik.

The present invention regards variant forms of the pro-apoptotic bik polynucleotide as a tumor suppressor gene to treat human ovarian cancer, pancreatic cancer, breast cancer, prostate cancer, and other cancers. In some embodiments it is delivered by, for example, either a viral or non-viral delivery system into an appropriate recipient animal to suppress tumor growth and development. In one exemplary embodiment of the present invention, the delivered Bik mutants act through an apoptosis mechanism to suppress tumor growth and development. Thus, herein the inventors demonstrate that the bik variants exerted strong anti-tumor activity and behaved like a classic tumor suppressor.

Bik was initially identified as a BH3-domain-only protein that interacts with E1B 19K and Bcl-2. Systemically administrated Bik significantly inhibited the tumor growth and metastasis in human breast cancer nude mice model. Recently, it has been reported that post-translational phosphorylation can regulate the pro-apoptotic potency of Bik. Here, the present inventors demonstrated that Bik mutants were more potent than wild type (wt) Bik to inhibit cell proliferation and enhance apoptosis induction in various human cancer cells. They also demonstrated that the Bik mutants suppressed the tumorigenicity and tumor taking rate in mice ex vivo model. Finally, the inventors demonstrated the Bik mutant-SN liposome inhibited the tumor growth and prolonged the life span in mice in vivo model. Thus, the present invention provides mutant Bik gene product, and polynucleotides that encode same, are more potent than wt Bik to induce cell death.

Exemplary mutants of Bik, Bik-T33D (threonine 33 to aspartate), Bik-S35D (serine 35 to aspartate) and Bik-T33DS35D (threonine 33 and serine 35 to aspartate), were generated. These mutants, in preferred embodiments of the present invention, selectively inhibit cancer cell growth and also preferably are more potent anti-cancer agents than the wild-type Bik. In other embodiments the mutant Biks inhibit other cell proliferation and is useful for the treatment of restenosis or to inhibit angiogenesis. One skilled in the art following the teachings of this specification can generate other exemplary mutants of Bik polypeptide.

A skilled artisan recognizes that a multitude of Bik nucleic acid and polypeptide sequences may be used in the present invention. A skilled artisan is aware of publicly available databases that provide these sequences, such as the National Center for Biotechnology Information's GenBank database or commercially available databases such as from Celera Genomics, Inc. (Rockville, Md.). Exemplary polypeptide sequences include (as identified by their GenBank Accession numbers): SEQ ID NO:3 (AAC50413; NP_001188; AAF01156; AAC79124; CAA62013; and 558214) and SEQ ID NO:4 (AAC40079). Exemplary polynucleotide sequences include (as identified by their GenBank Accession numbers): SEQ ID NO:5 (AY245248) and SEQ ID NO:6 (NM_001197).

In specific embodiments, the Bik polypeptide comprises at least one of the following domains: BH3 domain (for example, ALRLACIGDEMD; SEQ ID NO:10); at least one E1B 19K-interacting domain (for example, LRLACIG-DEMDV; SEQ ID NO:11); at least one Bcl-2-interacting domain (for example, ALALRLACIGDEMDVSLR; SEQ ID NO:12); and/or at least one heterodimerization domain (for example, LALRLACIGDEMDVSLRA; SEQ ID NO:13), such as with various anti-apoptotic proteins, e.g. Bcl-2 and Bcl-XL; and/or a transmembrane domain (for example, EQV-LLALLLLLALLLPLLSGGLHLLLK; SEQ ID NO:14), and at least some of the domains may overlap. In particular embodiments, the Bik polypeptide comprises no substantially functional phosphorylation sites at particular amino acids, although in alternative embodiments the Bik may comprise one or more functional phosphorylation sites. As used herein the term "no substantially functional phosphorylation sites" refers to the majority of Bik molecules lacking phosphorylation ability at one or more particular amino acids capable of being phosphorylated. In specific embodiments, the phosphorylation sites in question include Thr33 and Ser35. A skilled artisan recognizes how to assay for phosphorylation capability, such as providing antibodies specific for the phosphorylated species or for the non-phosphorylated species to the Bik form in question. A skilled artisan may also use two-dimensional gel electrophoresis or mass spectrum, for example, to identify the phosphorylation of these residues, in some embodiments.

A skilled artisan recognizes that the mutants of Bik, such as the exemplary BikT33D (threonine 33 to aspartate) (SEQ ID NO:7); BikS35D (serine 35 to aspartate) (SEQ ID NO:8); and Bik T33DS35D (both threonine 33 and serine 35 to aspartate) (SEQ ID NO:9), may be generated by a variety of means. In a specific embodiment, a nucleic acid sequence as set forth in, for example, SEQ ID NO:5 or SEQ ID NO:6, is mutated at least at the codon that encodes a particular amino acid desired to be altered, such as the threonine at residue 33 to encode an aspartic acid, and so forth. Table 1 presents codons for all standard amino acids, and a skilled artisan would be well aware how to manipulate a starting nucleic acid to generate a desired mutation using standard site-directed mutagenesis techniques, for example.

In an embodiment of the present invention, the Bik wild type gene product is phosphorylated under native conditions. In particular, the inventors have shown herein that mutant Bik, such as one or more comprising a mutation that encodes the T33 residue and/or the S35 residue, in spite of an inability to be phosphorylated, renders the mutant Bik gene product also useful for inhibition of cell growth and/or useful for pro-apoptotic activity. A skilled artisan recognizes that the T33 and/or S35 residues may be altered to prohibit phosphorylation. For example, the T33 amino acid residue may be changed by altering the nucleic acid codon that encodes it, such as by site-directed mutagenesis. Alternatively, the T33 and/or S35 amino acid(s) may be blocked with at least one compound that prevents phosphorylation, for example with blocking agents such as carbodiamide and/or by acetylation of the residue with acetylchloride in trifluoroacetic acid.

A skilled artisan recognizes that the substitution at Thr33 and/or Ser35 may prevent phosphorylation of the Bik polypeptide under conditions that would result in phosphorylation of an unsubstituted Bik polypeptide, and furthermore would know methods standard in the art to determine these conditions.

In one aspect of the invention, mutant Bik polypeptide having at least one defective phosphorylation site is administered as a polynucleotide that is regulated in a tissue-specific manner. In particular, mutant Bik may be targeted for expression in breast cancer, pancreatic cancer, or prostate cancer, for example. In certain aspects of the invention, a breast cancer-specific promoter controls expression of mutant Bik. Although any breast cancer-specific control sequence is contemplated by the present inventors, in a particular embodiment mutant Bik expression is controlled by a composite (chimeric) promoter. For example, breast cancer specific promoters comprised of a CMV promoter enhancer sequence linked with breast cancer specific segments in either topoisomerase IIα promoter (named as CT90) or transferring receptor promoter (named as CTR116) may be utilized. Both of these chimeric promoters drive gene expression selectively in breast cancer cells and possess activity levels comparable to the CMV promoter. The mutant Bik constructs employing the CT90 or CTR116 chimeric promoters are used in gene transfer to target and treat primary and metastatic breast cancers with less toxicity to normal tissues, preferably by selectively killing breast cancer cells and/or significantly reducing breast tumor growth and/or growth rate.

In other aspects of the invention, a prostate cancer-specific or pancreatic cancer-specific promoter controls expression of mutant Bik. Although any respective prostate cancer-specific or pancreatic cancer-specific promoter is contemplated by the present inventors, in a particular embodiment a composite prostate cancer-specific or pancreatic cancer-specific promoter, respectively, is utilized. For example, the prostate cancer-specific promoter may comprise an ARR2 control sequence, whereas the pancreatic cancer-specific promoter may comprise a CCKAR control sequence.

Any promoter or control sequence utilized to regulate expression of a polynucleotide encoding a mutant Bik polypeptide may utilize specific regulatory sequences that enhance expression and/or post-transcriptional processes, for example. Particular but exemplary sequences include enhancers, two-step transcriptional amplification system, elements that regulate RNA polyadenylation, half-life, and so forth, such as the WPRE, and others in the art.

In other embodiments of the present invention, there are methods of preventing growth of a cell in an individual comprising administering to the individual a mutant Bik polypeptide. In specific embodiments, the polypeptide is administered in a liposome and/or the polypeptide further comprises a protein transduction domain (Schwarze et al., 1999), such as HIV Tat or penetratin. In alternative embodiments, mutant Bik is administered as a polynucleotide, wherein the polynucleotide comprises the alteration that effects modification at the amino acid level, such as is generated by site-directed mutagenesis, for example. The modified Bik polynucleotide is administered in a vector such as a plasmid, retroviral vector, adenoviral vector, adeno-associated viral vector, liposome, or a combination thereof.

There are also embodiments of the present invention wherein there are methods of treating a cell comprising contacting the cell with a mutant Bik polypeptide. In specific embodiments, the cell is a human cell, the cell is comprised in an animal, and/or the animal is human.

It is contemplated herein that the compositions of the present invention preferably have an activity similar from a native Bik polypeptide in the cell, and which may be approximately the same or more potent against a cancer cell than native Bik. That is, the scope of the present invention, in some embodiments, is directed to a change in the native Bik polypeptide for use in a manner similar to the wildtype Bik polypeptide. In an alternative embodiment, the mutant Bik forms (e.g. different from the wild type sequence) comprise an activity different from the native Bik polypeptide.

I. Definitions and Techniques Affecting Bik Gene Products and Genes

A. Bik Gene Products and Genes

As used herein, the terms "mutant Bik gene product" and "mutant Bik" refer to proteins having amino acid sequences that are not identical to the native Bik but that are biologically active in that they are capable of performing similar activities to native Bik. For example, they are preferably capable of pro-apoptotic activity, anti-cell proliferative activity, anti-tumor activity and/or cross-reactive antibody activity with anti-Bik antibody raised against Bik. The term "Bik gene product" includes analogs of Bik molecules that exhibit at least some biological activity in common with native Bik. Furthermore, those skilled in the art of mutagenesis will appreciate that other analogs, as yet undisclosed or undiscovered, may be used to construct Bik analogs.

The term "mutant form of Bik" refers to any DNA sequence that is substantially identical to a DNA sequence encoding a Bik gene product as defined above. The term also refers to RNA or antisense sequences compatible with such DNA sequences. A "Bik gene" may also comprise any combination of associated control sequences.

The term "substantially identical", when used to define either a Bik amino acid sequence or Bik nucleic acid sequence, means that a particular subject sequence, for example, a mutant sequence, varies from the sequence of natural Bik by, for example, one or more substitutions, deletions, additions, or a combination thereof, the net effect of which is to retain at least some biological activity of the Bik protein. Alternatively, DNA analog sequences are "substantially identical" to specific DNA sequences disclosed herein if: (a) the DNA analog sequence is derived from coding regions of the natural Bik gene; or (b) the DNA analog sequence is capable of hybridization of DNA sequences of (a) under moderately stringent conditions and which encode biologically active Bik; or (c) DNA sequences that are degenerative as a result of the genetic code to the DNA analog sequences defined in (a) or (b). Substantially identical analog proteins will be greater than about 80% similar to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequence.

B. Percent Similarity

Percent similarity may be determined, for example, by comparing sequence information using the GAP computer program, available from the University of Wisconsin Geneticist Computer Group. The GAP program utilizes the alignment method of Needleman et al., 1970, as revised by Smith et al., 1981. Briefly, the GAP program defines similarity as the number of aligned symbols (i.e. nucleotides or amino acids) which are similar, divided by the total number of symbols in the shorter of the two sequences. The preferred default parameters for the GAP program include (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps.

II. Nucleic Acid Sequences

In certain embodiments, the invention concerns the use of mutant Bik nucleic acids, genes and gene products, such as the mutant Bik that includes a sequence that is different from that of the known Bik gene, or the corresponding protein. The term "a sequence essentially as Bik" means that the sequence substantially corresponds to a portion of the Bik gene and has relatively few bases or amino acids (whether DNA or protein) that are not identical to those of Bik (or a biologically functional equivalent thereof, when referring to proteins). The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of Bik will be sequences that are "essentially the same".

Mutant bik nucleic acids that have functionally equivalent codons are covered by the invention. The term "functionally equivalent codon" is used herein to refer to codons that encode the same amino acid, such as the six codons for arginine or serine, and also refers to codons that encode biologically equivalent amino acids (Table 1).

TABLE 1

FUNCTIONALLY EQUIVALENT CODONS

| Amino Acids | | | Codons |
|---|---|---|---|
| Alanine | Ala | A | GCA GCC GCG GCU |
| Cysteine | Cys | C | UGC UGU |

TABLE 1-continued

FUNCTIONALLY EQUIVALENT CODONS

| Amino Acids | | | Codons |
|---|---|---|---|
| Aspartic Acid | Asp | D | GAC GAU |
| Glutamic Acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments that are complementary, or essentially complementary, to the sequences set forth in the specification. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segment in question under relatively stringent conditions such as those described herein.

C. Biologically Functional Equivalents

As mentioned above, modification and changes may be made in the structure of Bik and still obtain a molecule having like or otherwise desirable characteristics. For example, certain amino acids may be substituted for other amino acids in a protein structure without appreciable loss of interactive binding capacity with structures such as, for example, E1B 19K or Bcl-2. Since, in many embodiments, it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic vs. agonistic). It is thus contemplated by the inventors that various changes may be made in the sequence of the mutant Bik proteins or peptides (or underlying DNA) without appreciable loss of their desired biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged.

Amino acid substitutions, such as those that might be employed in modifying Bik, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0.+−0.1); glutamate (+3.0.+−0.1); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those that are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

III. Nucleic Acid-Based Expression Systems

The present invention utilizes, in some embodiments, systems for expressing mutant Bik-comprising polynucleotides. Particular exemplary aspects for these polynucleotides are described herein.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. In a specific embodiment, a control sequence, such as a promoter, regulates the tissue specificity within which the nucleic acid sequence is expressed. A promoter, or control sequence, may comprise genetic elements at which regulatory proteins and molecules may bind, such as RNA polymerase and other transcription factors. The phrases "operatively positioned," "operatively linked," "under control," and "under transcriptional control" mean that a promoter or other control sequence is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202; U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Table 2 lists several elements/promoters that may be employed, in the context of the present invention, to regulate the expression of a gene. This list is not intended to be exhaustive of all the possible elements involved in the promotion of expression but, merely, to be exemplary thereof. Table 3 provides examples of inducible elements, which are regions of a nucleic acid sequence that can be activated in response to a specific stimulus.

TABLE 2

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al.; 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| t-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| α1-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |

TABLE 2-continued

Promoter and/or Enhancer

| Promoter/Enhancer | References |
|---|---|
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |
| Papilloma Virus | Campo et al., 1983; Lusky et al., 1983; Spandidos and Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 3

Inducible Elements

| Element | Inducer | References |
|---|---|---|
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI) x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), or human platelet endothelial cell adhesion molecule-1 (Almendro et al., 1996), for example.

Tissue-specific promoters utilized to control expression targeting and/or levels of mutant Bik may be endogenous wild-type promoters, mutant promoters, or synthetic promoters, so long as the expression of mutant Bik is preferentially retained in one or more tissues of interest compared to tissues that are not the desired target. Synthetic promoters may be further defined as composite promoters, referred to herein as a promoter comprising at least two separate regions originating from different endogenous and/or synthetic promoters yet operably linked to control expression of a mutant Bik. In a particular embodiment, the tissue specificity refers to specificity for cancerous tissue, as opposed to non-cancerous tissue. The term "cancerous tissue" as used herein refers to a tissue comprising at least one cancer cell.

a. Breast Cancer Tissue-Specific Promoters

Most of the promoters currently used in cancer gene therapy possess strong but unselective activity (e.g. CMV and β-actin promoters) in both normal and tumor cells. Thus, in some aspects of the present invention, a breast tissue-specific promoter is utilized in the invention, such as to control expression of a mutant form of Bik, including the exemplary BikT33D, BikS35D, and Bik T33DS35D mutants. In a particular aspect, the breast tissue-specific promoter is a breast cancer tissue-specific promoter. As such, the desired promoter for this embodiment targets expression specifically to breast cancer tissue.

Any breast cancer tissue-specific promoter may be employed in the invention so long as it preferentially directs expression of mutant Bik in breast cancer tissue. Examples of breast cancer tissue-specific promoters that may direct expression of mutant Bik in breast cancer tissue include at least hALA, GLG, HK-II, and HER2 promoters (Anderson et al., 2000; Katabi et al., 1999; Lu et al., 2002; Maeda et al., 2001).

In one particular embodiment of the present invention, composite promoters utilizing either topoisomerase IIα (topoIIα) and transferrin receptor (TfR) breast cancer-specific control sequences are employed. The topoisomerase IIα (topoIIα) and transferrin receptor (TfR) levels are elevated in breast cancer, as determined using SAGE analysis and cDNA microarray, for example. The present inventors identified a 90 base pair segment (SEQ ID NO:26) and a 116 base pair segment (SEQ ID NO:27) in the 5'-end of topoIIα and TfR promoter, respectively, as a minimally required breast-cancer specific control sequence. In particular embodiments, the promoter activity is enhanced by operatively linking these two short promoters with an enhancer sequence, such as the cytomegalovirus (CMV) promoter enhancer sequence (SEQ ID NO:25); these chimeric promoters are referred to herein as CT90 and CTR116, respectively. The full CT90 promoter is comprised in SEQ ID NO:37, and the full CTR116 promoter is comprised in SEQ ID NO:38. These promoters are described herein but are further characterized in detail in U.S. Provisional Patent Application No. 60/559,111, entitled "Cancer-Specific Promoters" by Mien-Chie Hung, Yan Li, Yong Wen, Chi-Ping Day, Kun-Ming Rau, Xiaoming Xie, Zheng Li, filed simultaneously herewith and incorporated by reference herein in its entirety. To demonstrate its use in cancer gene therapy, the present inventors generated a DNA construct using CT90 to drive mutant Bik expression. When transfected into cell lines, this construct selectively killed breast cancer cells. Moreover, the present inventors demonstrated that this construct had an anti-tumor effect on breast tumor xenograft in mouse by intravenous injection with an exemplary non-viral delivery system. This indicates that CT90 and CTR116 can drive the expression of a therapeutic gene such as mutant Bik selectively in breast cancer cells.

Thus, the current invention encompasses breast cancer-specific promoters for control of expression of mutant Bik to target breast cancer cells for treatment that is less toxic or non-toxic to normal tissues.

b. Pancreatic Cancer Tissue-Specific Promoters

Pancreatic-specific promoters can be used for targeted expression of mutant Bik, including the exemplary BikT33D, BikS35D, and Bik T33DS35D mutants. Any pancreatic cancer tissue-specific promoter may be employed in the invention so long as it preferentially directs expression of mutant Bik in pancreatic cancer tissue. Examples of pancreatic cancer tissue-specific promoters that may direct expression of mutant Bik in pancreatic cancer tissue include the insulin promoter, such as the rat insulin promoter (Wang et al., 2004); midkine and cyclooxygenase-2 promoters (Wesseling et al., 2001); and carcinoembryonic antigen (CEA) promoter (Takeuchi et al., 2000), for example.

The present inventors developed a pancreatic cancer-specific promoter that is described herein but provided in further detail in U.S. Provisional Patent Application 60/559,111, entitled "Cancer-Specific Promoters" by Mien-Chie Hung, Yan Li, Yong Wen, Chi-Ping Day, Kun-Ming Rau, Xiaoming Xie, Zheng Li, filed simultaneously herewith, which is incorporated by reference herein in its entirety. The promoter comprises Cholecystoskinin A receptor (CCKAR) promoter sequence, particularly CCKAR promoter ranging from nt −726 to +1 (SEQ ID NO:28) operatively linked to an enhancer, such as CMV enhancer. The CCKAR-CMV composite is then engineered with a particular two-step transcriptional amplification (TSTA) system (Iyer et al., 2001; Zhang et al., 2002; Sato et al., 2003; and references cited therein), such as the exemplary GAL4-VP16 or GAL4-VP2 fusion protein, to augment the transcriptional activity and, it is also operatively linked to the post-transcriptional regulatory element of the woodchuck hepatitis virus (WPRE) (SEQ ID NO:29) to modify RNA polyadenylation signal, RNA export, and/or RNA translation. A skilled artisan recognizes that the term "two-step transcriptional amplification (TSTA) system" may also be referred to as "two-step transcriptional activation (TSTA) system" or "recombinant transcriptional activation approach" (Nettelbeck et al., 2000). In a particular aspect, the CCAKAR-TSTA-WPRE (CTP) promoter is utilized, and an example of such a composite promoter is comprised in SEQ ID NO:34. Thus, the molecularly engineered CTP promoter is employed for effective treatment modalities for pancreatic cancer gene therapy with mutant Bik.

c. Prostate Cancer Tissue-Specific Promoters

Prostate cancer tissue-specific promoters can be used to control expression of polynucleotides that encode mutant Bik. Prostate-specific promoters, like PSA, probasin and hK2, for example, have been recently developed. The activities of these promoters are androgen-dependent. For numerous disease stages, patients are androgen-dependent (ADPC), allowing the use of androgen-responsive vectors to direct expression of therapeutic genes to prostatic tissue. Although robust prostate-specific promoters responsive to androgen receptor have been developed by the present inventors (Xie et al., Cancer Res 2001) and other groups (Zhang et al., Mol Endocrinol 2000), these androgen-dependent promoters may be less active after castration or androgen ablation therapy, which are the main modalities for progressive prostate cancer treatment. These patients treated with compositions comprising these promoters may fail this kind of therapy and die of recurrent androgen-independent prostate cancer (AIPC).

The inventors have developed prostate cancer-specific promoters that may be expected to have benefit for both ADPC and androgen-independent prostate cancer (AIPC) to treat metastatic and recurrent hormonal refractory prostate cancer, particularly to regulate expression of mutant Bik. This promoter is described herein and characterized in further detail in U.S. Provisional Patent Application No. 60/559,111, entitled "Cancer-Specific Promoters" by Mien-Chie Hung, Yan Li, Yong Wen, Chi-Ping Day, Kun-Ming Rau, Xiaoming Xie, Zheng Li, filed simultaneously herewith and incorporated by reference herein in its entirety. The promoter, referred to herein as ATTP, comprises at least the minimal promoter fragment (hTERTp) of the human telomerase reverse transcriptase (hTERT) (SEQ ID NO:32) operably linked to a two-step transcriptional amplification (TSTA) system, such as the exemplary GAL4-VP16 or GAL4-VP2 (two examples of GAL4-VP2 are SEQ ID NO:30 or SEQ ID NO:33) fusion protein-encoding sequences, and it is also operatively linked to the post-transcriptional regulatory element of the woodchuck hepatitis virus (WPRE) to modify RNA polyadenylation signal, RNA export, and/or RNA translation. These regulatory sequences are effective in both ADPC and AIPC cell lines. Given that in most cases of recurrent prostate cancers the AR gene is amplified and/or AR is overexpressed, this particular promoter greatly improves the effective index for the embodiment wherein the activity of this system is stimulated by androgen. In preferred embodiments the tissue-specificity region comprises at least, and for example, the ARR2 regulatory element (SEQ ID NO:31) from ARR2 gene. In a particular aspect of the invention, the TSTA-hTERT-ARR2 and WPRE elements are utilized as the prostate cancer-specific regulatory elements, which in specific embodiments are comprised in SEQ ID NO:35. Thus, the present inventors have developed a novel prostate cancer-specific regulatory system that will target mutant Bik to not only ADPC but also AIPC.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

5. Polyadenylation Signals

In expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Also contemplated as an element of the expression cassette is a transcriptional termination site. These elements can serve to enhance message levels and/or to minimize read through from the cassette into other sequences.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, the cells contain nucleic acid construct of the present invention, a cell may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and Solopack™ Gold Cells (Stratagene®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

C. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MaxBac® 2.0 from Invitrogen® and BacPack™ Baculovirus Expression System From Clontech®.

Other examples of expression systems include Stratagene®'s Complete Control™ Inducible Mammalian Expression System, which involves a synthetic ecdysone-inducible receptor, or its pET Expression System, an *E. coli* expression system. Another example of an inducible expression system is available from Invitrogen®, which carries the T-Rex™ (tetracycline-regulated expression) System, an inducible mammalian expression system that uses the full-length CMV promoter. Invitrogen® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

IV. Nucleic Acid Delivery

The general approach to the aspects of the present invention concerning compositions and/or therapeutics is to provide a cell with a gene construct encoding a specific and/or desired mutant Bik protein, polypeptide, or peptide, thereby permitting the desired activity of the protein, polypeptide, or peptide to take effect. While it is conceivable that the gene construct and/or protein may be delivered directly, a preferred embodiment involves providing a nucleic acid encoding a specific and desired protein, polypeptide, or peptide to the cell. Following this provision, the proteinaceous composition is synthesized by the transcriptional and translational machinery of the cell, as well as any that may be provided by the expression construct. In providing antisense, ribozymes and other inhibitors, the preferred mode is also to provide a nucleic acid encoding the construct to the cell.

In certain embodiments of the invention, the nucleic acid encoding the gene may be stably integrated into the genome of the cell. In yet further embodiments, the nucleic acid may be stably maintained in the cell as a separate, episomal segment of DNA. Such nucleic acid segments and "episomes" encode sequences sufficient to permit maintenance and replication independent of and in synchronization with the host cell cycle. How the expression construct is delivered to a cell and/or where in the cell the nucleic acid remains is dependent on the type of expression construct employed.

A. DNA Delivery Using Viral Vectors

The ability of certain viruses to infect cells and enter cells via receptor-mediated endocytosis, and to integrate into host cell genome and/or express viral genes stably and/or efficiently have made them attractive candidates for the transfer of foreign genes into mammalian cells. Preferred gene therapy vectors of the present invention will generally be viral vectors.

Although some viruses that can accept foreign genetic material are limited in the number of nucleotides they can accommodate and/or in the range of cells they infect, these viruses have been demonstrated to successfully effect gene expression. However, adenoviruses do not integrate their genetic material into the host genome and/or therefore do not require host replication for gene expression, making them ideally suited for rapid, efficient, heterologous gene expression. Techniques for preparing replication-defective infective viruses are well known in the art.

Of course, in using viral delivery systems, one will desire to purify the virion sufficiently to render it essentially free of undesirable contaminants, such as defective interfering viral particles and endotoxins and other pyrogens such that it will not cause any untoward reactions in the cell, animal and/or individual receiving the vector construct. A preferred means of purifying the vector involves the use of buoyant density gradients, such as cesium chloride gradient centrifugation.

1. Adenoviral Vectors

A particular method for delivery of the expression constructs involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and/or (b) to ultimately express a tissue and/or cell-specific construct that has been cloned therein.

The expression vector comprises a genetically engineered form of adenovirus. Knowledge of the genetic organization and adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and/or no genome rearrangement has been detected after extensive amplification.

Adenovirus is particularly suitable for use as a gene transfer vector because of its mid-sized genome, ease of manipulation, high titer, wide target-cell range and/or high infectivity. Both ends of the viral genome contain 100-200 base pair inverted repeats (ITRs), which are cis elements necessary for viral DNA replication and/or packaging. The early (E) and/or late (L) regions of the genome contain different transcription units that are divided by the onset of viral DNA replication. The E1 region (E1A and/or E1B) encodes proteins responsible for the regulation of transcription of the viral genome and/or a few cellular genes. The expression of the E2 region (E2A and/or E2B) results in the synthesis of the proteins for viral DNA replication. These proteins are involved in DNA replication, late gene expression and/or host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and/or all the mRNA's issued from this promoter possess a 5'-tripartite leader (TPL) sequence which makes them preferred mRNA's for translation.

In a current system, recombinant adenovirus is generated from homologous recombination between shuttle vector and provirus vector. Due to the possible recombination between two proviral vectors, wild-type adenovirus may be generated from this process. Therefore, it is critical to isolate a single clone of virus from an individual plaque and/or examine its genomic structure.

Generation and/or propagation of the current adenovirus vectors, which are replication deficient, depend on a unique helper cell line, designated 293, which was transformed from human embryonic kidney cells by Ad5 DNA fragments and constitutively expresses E1 proteins (E1A and/or E1B; Graham et al., 1977). Since the E3 region is dispensable from the adenovirus genome (Jones and Shenk, 1978), the current adenovirus vectors, with the help of 293 cells, carry foreign DNA in either the E1, the D3 and both regions (Graham and Prevec, 1991). Recently, adenoviral vectors comprising deletions in the E4 region have been described (U.S. Pat. No. 5,670,488, incorporated herein by reference).

In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and/or E3 regions, the maximum capacity of the current adenovirus vector is under 7.5 kb, and/or about 15% of the total length of the vector. More than 80% of the adenovirus viral genome remains in the vector backbone.

Helper cell lines may be derived from human cells such as human embryonic kidney cells, muscle cells, hematopoietic cells and other human embryonic mesenchymal and epithelial cells. Alternatively, the helper cells may be derived from the cells of other mammalian species that are permissive for human adenovirus. Such cells include, e.g., Vero cells and other monkey embryonic mesenchymal and/or epithelial cells. As stated above, the preferred helper cell line is 293.

Recently, Racher et al. (1995) disclosed improved methods for culturing 293 cells and/or propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and/or left stationary, with occasional agitation, for 1 to 4 h. The medium is then replaced with 50 ml of fresh medium and/or shaking initiated. For virus production, cells are allowed to grow to about 80% confluence, after which time the medium is replaced (to 25% of the final volume) and/or adenovirus added at an MOI of 0.05. Cultures are left stationary overnight, following which the volume is increased to 100% and/or shaking commenced for another 72 h.

Other than the requirement that the adenovirus vector be replication defective, and at least conditionally defective, the nature of the adenovirus vector is not believed to be crucial to the successful practice of the invention. The adenovirus may be of any of the 42 different known serotypes and subgroups A-F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the transforming construct at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al. (1986) and in the E4 region where a helper cell line and helper virus complements the E4 defect.

Adenovirus growth and/or manipulation is known to those of skill in the art, and/or exhibits broad host range in vitro and in vivo. This group of viruses can be obtained in high titers, e.g., 109 to 1011 plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and/or therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991a; Stratford-Perricaudet et al., 1991b; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and/or stereotactic inoculation into the brain (Le Gal La Salle et al., 1993). Recombinant adenovirus and adeno-associated virus (see below) can both infect and transduce non-dividing human primary cells.

2. AAV Vectors

Adeno-associated virus (AAV) is an attractive vector system for use in the cell transduction of the present invention as it has a high frequency of integration and it can infect nondividing cells, thus making it useful for delivery of genes into mammalian cells, for example, in tissue culture (Muzyczka, 1992) and in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. No. 5,139,941 and/or U.S. Pat. No. 4,797,368, each incorporated herein by reference.

Studies demonstrating the use of AAV in gene delivery include LaFace et al. (1988); Zhou et al. (1993); Flotte et al. (1993); and Walsh et al. (1994). Recombinant AAV vectors have been used successfully for in vitro and/or in vivo transduction of marker genes (Kaplitt et al., 1994; Lebkowski et al., 1988; Samulski et al., 1989; Yoder et al., 1994; Zhou et al., 1994; Hermonat and Muzyczka, 1984; Tratschin et al., 1985; McLaughlin et al., 1988) and genes involved in human diseases (Flotte et al., 1992; Luo et al., 1994; Ohi et al., 1990; Walsh et al., 1994; Wei et al., 1994). Recently, an AAV vector has been approved for phase I human trials for the treatment of cystic fibrosis.

AAV is a dependent parvovirus in that it requires coinfection with another virus (either adenovirus and a member of the herpes virus family) to undergo a productive infection in cultured cells (Muzyczka, 1992). In the absence of coinfection with helper virus, the wild type AAV genome integrates through its ends into human chromosome 19 where it resides in a latent state as a provirus (Kotin et al., 1990; Samulski et al., 1991). rAAV, however, is not restricted to chromosome 19 for integration unless the AAV Rep protein is also expressed (Shelling and Smith, 1994). When a cell carrying an AAV provirus is superinfected with a helper virus, the AAV genome is "rescued" from the chromosome and from a recombinant plasmid, and/or a normal productive infection is established (Samulski et al., 1989; McLaughlin et al., 1988; Kotin et al., 1990; Muzyczka, 1992).

Typically, recombinant AAV (rAAV) virus is made by cotransfecting a plasmid containing the gene of interest flanked by the two AAV terminal repeats (McLaughlin et al., 1988; Samulski et al., 1989; each incorporated herein by reference) and/or an expression plasmid containing the wild type AAV coding sequences without the terminal repeats, for example pIM45 (McCarty et al., 1991; incorporated herein by reference). The cells are also infected and transfected with adenovirus and plasmids carrying the adenovirus genes required for AAV helper function. rAAV virus stocks made in such fashion are contaminated with adenovirus which must be physically separated from the rAAV particles (for example, by cesium chloride density centrifugation). Alternatively, adenovirus vectors containing the AAV coding regions and cell lines containing the AAV coding regions and some and all of the adenovirus helper genes could be used (Yang et al., 1994; Clark et al., 1995). Cell lines carrying the rAAV DNA as an integrated provirus can also be used (Flotte et al., 1995).

3. Retroviral Vectors

Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and/or directs synthesis of viral proteins. The integration results in the retention of the viral gene sequences in the recipient cell and/or its descendants. The retroviral genome contains three genes, gag, pol, and/or env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and/or stable expression require the division of host cells (Paskind et al., 1975).

Concern with the use of defective retrovirus vectors is the potential appearance of wild-type replication-competent virus in the packaging cells. This can result from recombination events in which the intact sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity.

4. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988), sindbis virus, cytomegalovirus and/or herpes simplex virus may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. Chang et al. recently introduced the chloramphenicol acetyltransferase (CAT) gene into duck hepatitis B virus genome in the place of the polymerase, surface, and/or pre-surface coding sequences. It was cotransfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In certain further embodiments, the gene therapy vector will be HSV. A factor that makes HSV an attractive vector is the size and organization of the genome. Because HSV is large, incorporation of multiple genes and expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and/or can be grown to high titers. Thus, delivery is less of a problem, both in terms of volumes needed to attain sufficient MOI and in a lessened need for repeat dosings.

5. Modified Viruses

In still further embodiments of the present invention, the nucleic acids to be delivered are housed within an infective virus that has been engineered to express a specific binding ligand. The virus particle will thus bind specifically to the cognate receptors of the target cell and deliver the contents to the cell. A novel approach designed to allow specific targeting of retrovirus vectors was recently developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and/or against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

B. Other Methods of DNA Delivery

In various embodiments of the invention, DNA is delivered to a cell as an expression construct. In order to effect expression of a gene construct, the expression construct must be delivered into a cell. As described herein, the preferred mechanism for delivery is via viral infection, where the expression construct is encapsidated in an infectious viral particle. However, several non-viral methods for the transfer of expression constructs into cells also are contemplated by the present invention. In one embodiment of the present invention, the expression construct may consist only of naked recombinant DNA and/or plasmids. Transfer of the construct may be performed by any of the methods mentioned which physically and/or chemically permeabilize the cell membrane. Some of these techniques may be successfully adapted for in vivo and/or ex vivo use, as discussed below.

C. Liposome-Mediated Transfection

In a further embodiment of the invention, the expression construct may be entrapped in a liposome. Liposomes are vesicular structures characterized by a phospholipid bilayer membrane and/or an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and/or entrap water and/or dissolved solutes between the lipid bilayers (Ghosh and Bachhawat, 1991). Also contemplated is an expression construct complexed with Lipofectamine (Gibco BRL).

Liposome-mediated nucleic acid delivery and expression of foreign DNA in vitro has been very successful (Nicolau and Sene, 1982; Fraley et al., 1979; Nicolau et al., 1987). Wong et al. (1980) demonstrated the feasibility of liposome-mediated delivery and/or expression of foreign DNA in cultured chick embryo, HeLa and hepatoma cells.

In certain embodiments of the invention, the liposome may be complexed with a hemagglutinating virus (HVJ). This has been shown to facilitate fusion with the cell membrane and/or promote cell entry of liposome-encapsulated DNA (Kaneda et al., 1989). In other embodiments, the liposome may be complexed and/or employed in conjunction with nuclear non-histone chromosomal proteins (HMG-1) (Kato et al., 1991). In yet further embodiments, the liposome may be complexed and/or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

The inventors contemplate that neu-suppressing gene products can be introduced into cells using liposome-mediated gene transfer. It is proposed that such constructs can be coupled with liposomes and directly introduced via a catheter, as described by Nabel et al. (1990). By employing these methods, the neu-suppressing gene products can be expressed efficiently at a specific site in vivo, not just the liver and spleen cells which are accessible via intravenous injection. Therefore, this invention also encompasses compositions of DNA constructs encoding a neu-suppressing gene product formulated as a DNA/liposome complex and methods of using such constructs.

As described in U.S. Pat. No. 5,641,484, liposomes are particularly well suited for the treatment of HER2/neu-mediated cancer a. Preparation of Liposomes Catatonic liposomes that are efficient transfection reagents for Bik for animal cells can be prepared using the method of Gao et al. (1991). Gao et al. describes a novel catatonic cholesterol derivative that can be synthesized in a single step. Liposomes made of this lipid are reportedly more efficient in transfection and less toxic to treated cells than those made with the reagent Lipofectin. These lipids are a mixture of DC-Chol ("3□(N—(N'N'-dimethylaminoethane)-carbamoyl cholesterol") and DOPE ("dioleoylphosphatidylethanolamine"). The steps in producing these liposomes are as follows.

DC-Chol is synthesized by a simple reaction from cholesteryl chloroformate and N,N-Dimethylethylenediamine. A solution of cholesteryl chloroformate (2.25 g, 5 mmol in 5 ml dry chloroform) is added dropwise to a solution of excess N,N-Dimethylethylenediamine (2 ml, 18.2 mmol in 3 ml dry chloroform) at 0° C. Following removal of the solvent by evaporation, the residue is purified by recrystallization in absolute ethanol at 4° C. and dried in vacuo. The yield is a white powder of DC-Chol.

Cationic liposomes are prepared by mixing 1.2 □mol of DC-Chol and 8.0 □mol of DOPE in chloroform. This mixture is then dried, vacuum desiccated, and resuspended in 1 ml sterol 20 mM Hepes buffer (pH 7.8) in a tube. After 24 hours of hydration at 4° C., the dispersion is sonicated for 5-10 minutes in a sonicator form liposomes with an average diameter of 150-200 nm.

To prepare a liposome/DNA complex, the inventors use the following steps. The DNA to be transfected is placed in DMEM/F12 medium in a ratio of 15 μg DNA to 50 μl DMEM/F12. DMEM/F12 is then used to dilute the DC-Chol/DOPE liposome mixture to a ratio of 50 DMEZM/F12 to 100 μl liposome. The DNA dilution and the liposome dilution are then gently mixed, and incubated at 37° C. for 10 minutes. Following incubation, the DNA/liposome complex is ready for injection.

Liposomal transfection can be via liposomes composed of, for example, phosphatidylcholine (PC), phosphatidylserine (PS), cholesterol (Chol), N-[1-(2,3-dioleyloxy)propyl]-N,N-trimethylammonium chloride (DOTMA), dioleoylphosphatidylethanolamine (DOPE), and/or 3.beta.[N—(N'N'-dimethylaminoethane)-carbarmoyl cholesterol (DC-Chol), as well as other lipids known to those of skill in the art. Those of skill in the art will recognize that there are a variety of liposomal transfection techniques that will be useful in the present invention. Among these techniques are those described in Nicolau et al., 1987, Nabel et al., 1990, and Gao et al., 1991. In a specific embodiment, the liposomes comprise DC-Chol. More particularly, the inventors the liposomes comprise DC-Chol and DOPE that have been prepared following the teaching of Gao et al. (1991) in the manner described in the Preferred Embodiments Section. The inventors also anticipate utility for liposomes comprised of DOTMA, such as those that are available commercially under the trademark Lipofectin™, from Vical, Inc., in San Diego, Calif.

Liposomes may be introduced into contact with cells to be transfected by a variety of methods. In cell culture, the liposome-DNA complex can simply be dispersed in the cell culture solution. For application in vivo, liposome-DNA complex are typically injected. Intravenous injection allow liposome-mediated transfer of DNA complex, for example, the liver and the spleen. In order to allow transfection of DNA into cells that are not accessible through intravenous injection, it is possible to directly inject the liposome-DNA complexes into a specific location in an animal's body. For example, Nabel et al. teach injection via a catheter into the arterial wall. In another example, the inventors have used intraperitoneal injection to allow for gene transfer into mice.

The present invention also contemplates compositions comprising a liposomal complex. This liposomal complex will comprise a lipid component and a DNA segment encoding a nucleic acid encoding a mutant form of Bik. The nucleic acid encoding the mutant form of Bik employed in the liposomal complex can be, for example, one that encodes Bik-T145A or Bik-T145D.

The lipid employed to make the liposomal complex can be any of the above-discussed lipids. In particular, DOTMA, DOPE, and/or DC-Chol may form all or part of the liposomal complex. The inventors have had particular success with complexes comprising DC-Chol. In a preferred embodiment, the lipid will comprise DC-Chol and DOPE. While any ratio of DC-Chol to DOPE is anticipated to have utility, it is anticipated that those comprising a ratio of DC-Chol:DOPE between 1:20 and 20:1 will be particularly advantageous. The inventors have found that liposomes prepared from a ratio of DC-Chol:DOPE of about 1:10 to about 1:5 have been useful.

In a specific embodiment, one employs the smallest region needed to enhance retention of Bik in the nucleus of a cell so that one is not introducing unnecessary DNA into cells which receive a Bik gene construct. Techniques well known to those of skill in the art, such as the use of restriction enzymes, will allow for the generation of small regions of Bik. The ability of these regions to inhibit neu can easily be determined by the assays reported in the Examples.

In certain embodiments of the invention, the liposome may be complexed with a hemagglutinatin virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

b. In Vivo Treatment of Cancer Via Liposomes with Bik Mutants

Based on the teachings provided herein, a skilled artisan recognizes that any cell may be treated with at least one Bik mutant, and in particular embodiments, any cancer cell may be treated with such. For example, in some embodiments the nature of the treated cell is irrespective of being HER2/neu-positive or HER2/neu-negative. However, in one specific embodiment it is HER2/neu-positive.

U.S. Pat. No. 5,641,484, incorporated in its entirety by reference herein, teaches that liposome-mediated direct gene transfer techniques can be employed to obtain suppression of HER2/neu-overexpressing human cancer cells in living host. The protocol for described therein was as follows. Female nude mice (5-6 weeks old) were given intraperitoneal injections of SK-OV-3 cells ($2\times10^6$/100 μl). SK-OV-3 cells are human ovarian cancer cells that have been shown to grow within the peritoneal cavity of nude mice. After five days, the mice were given intraperitoneal injections of various compounds. Some mice were injected with the therapeutic DNA alone, some were injected with liposome/therapeutic DNA complex prepared in the manner described above, and some were injected with liposome/mutant therapeutic DNA complex. 200 μl of a given compound was injected into a given mouse. After the initial injections, injections were repeated every seven days throughout the life of the mouse.

The results described therein indicate that liposome-mediated gene transfer can inhibit HER2/neu-overexpressing human ovarian cancer cell growth. Therefore, it is predictable that liposome-mediated mutant Bik gene therapy may serve as a powerful therapeutic agent for HER-2 neu-overexpressing human ovarian cancers by direct targeting of mutant Bik at the HER-2 neu-oncogene.

c. Liposomal Transfection with Mutant Bik to Treat Humans

Based on the results of the in vivo animal studies described in U.S. Pat. No. 5,641,484, those of skill in the art will understand and predict the enormous potential for human treatment of HER2/neu-mediated cancers with Bik T33D, S35D, and/or T33DS35D DNA complexed to liposomes. Clinical studies to demonstrate these affects are contemplated. Those of skill in the art will recognize that the best treatment regimens for using Bik T33D, S35D, and/or T33DS35D to suppress HER2/neu-mediated cancers can be straightforwardly determined. This is not a question of experimentation, but rather one of optimization, which is routinely conducted in the medical arts. In vivo studies in nude mice provide a starting point from which to begin to optimize the dosage and delivery regimes. The frequency of injection is initially once a week, as was done in the mice studies described in U.S. Pat. No. 5,641,484. However, this frequency might be optimally adjusted from one day to every two weeks to monthly, depending upon the results obtained from the initial clinical trials and the needs of a particular patient. Human dosage amounts can initially be determined by extrapolating from the amount of Bik T33D, S35D, and/or T33DS35D used in mice, approximately 15 μg of plasmid DNA per 50 g body weight. Based on this, a 50 kg woman would require treatment with 15 mg of DNA per dose. Of course, this dosage amount may be adjusted upward or downward, as is routinely done in such treatment protocols, depending on the results of the initial clinical trials and the needs of a particular patient. These clinical trials are anticipated to show utility of Bik T33D, S35D, and/or T33DS35D and other neu-suppressing gene products for the treatment of HER2/neu-overexpressing cancers in humans. Dosage and frequency regimes will initially be based on the data obtained from in vivo animal studies, as is done frequently in the art.

D. Electroporation

In certain embodiments of the present invention, the expression construct is introduced into the cell via electroporation. Electroporation involves the exposure of a suspension of cells and/or DNA to a high-voltage electric discharge.

Transfection of eukaryotic cells using electroporation has been quite successful. Mouse pre-B lymphocytes have been transfected with humankappa-immunoglobulin genes (Potter et al., 1984), and/or rat hepatocytes have been transfected with the chloramphenicol acetyltransferase gene (Tur-Kaspa et al., 1986) in this manner.

E. Calcium Phosphate and/or DEAE-Dextran

In other embodiments of the present invention, the expression construct is introduced to the cells using calcium phosphate precipitation. HumanKB cells have been transfected with adenovirus 5 DNA (Graham and Van Der Eb, 1973) using this technique. Also in this manner, mouse L(A9), mouse C127, CHO, CV-1, BHK, NIH3T3 and/or HeLa cells were transfected with a neomycin marker gene (Chen and Okayama, 1987), and/or rat hepatocytes were transfected with a variety of marker genes (Rippe et al., 1990).

In another embodiment, the expression construct is delivered into the cell using DEAE-dextran followed by polyethylene glycol. In this manner, reporter plasmids were introduced into mouse myeloma and/or erythroleukemia cells (Gopal, 1985).

F. Particle Bombardment

Another embodiment of the invention for transferring a naked DNA expression construct into cells may involve particle bombardment. This method depends on the ability to accelerate DNA-coated microprojectiles to a high velocity allowing them to pierce cell membranes and/or enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten and/or gold beads.

G. Direct Microinjection and/or Sonication Loading

Further embodiments of the present invention include the introduction of the expression construct by direct microinjection and/or sonication loading. Direct microinjection has been used to introduce nucleic acid constructs into *Xenopus oocytes* (Harland and Weintraub, 1985), and/or LTK-fibroblasts have been transfected with the thymidine kinase gene by sonication loading (Fechheimer et al., 1987).

H. Adenoviral Assisted Transfection

In certain embodiments of the present invention, the expression construct is introduced into the cell using adenovirus assisted transfection. Increased transfection efficiencies have been reported in cell systems using adenovirus coupled systems (Kelleher and Vos, 1994; Cotten et al., 1992; Curiel, 1994).

V. Combination Treatments

In order to increase the effectiveness of a mutant form of Bik, or expression construct coding therefore, it may be desirable to combine these compositions with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver et al., 1992). In the context of the present invention, it is contemplated that Bik gene therapy could be used similarly in conjunction with chemotherapeutic, radiotherapeutic, or immunotherapeutic intervention, in addition to other pro-apoptotic or cell cycle regulating agents.

Alternatively, the gene therapy may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, gene therapy is "A" and the secondary agent, such as radio- or chemotherapy, is "B":

| | | | | | |
|---|---|---|---|---|---|
| A/B/A | B/A/B | B/B/A | A/A/B | A/B/B | B/A/A |
| A/B/B/B | B/A/B/B | B/B/B/A | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

Administration of the therapeutic expression constructs of the present invention to a patient will follow general protocols for the administration of chemotherapeutics, taking into account the toxicity, if any, of the vector. It is expected that the treatment cycles would be repeated as necessary. It also is contemplated that various standard therapies, as well as surgical intervention, may be applied in combination with the described hyperproliferative cell therapy.

A. Chemotherapy

A skilled artisan recognizes that in addition to the Bik mutant forms described herein for the purpose of inhibiting cell growth, other chemotherapeutic agents are useful in the treatment of neoplastic disease. Examples of such chemotherapeutic agents are described in the following Table 4.

Cancer therapies include a variety of combination therapies with both chemical and radiation based treatments. Exemplary embodiments include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing.

TABLE 4

Chemotherapeutic Agents Useful In Neoplastic Disease

| CLASS | TYPE OF AGENT | NONPROPRIETARY NAMES (OTHER NAMES) | DISEASE |
|---|---|---|---|
| Alkylating Agents | Nitrogen Mustards | Mechlorethamine (HN2) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (l-sarcolysin) | Multiple myeloma, breast, ovary |
| | | Chlorambucil | Chronic lymphocytic leukemia, primary macroglobulinemia, Hodgkin's disease, non-Hodgkin's lymphomas |
| | Ethylenimenes and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |

TABLE 4-continued

Chemotherapeutic Agents Useful In Neoplastic Disease

| CLASS | TYPE OF AGENT | NONPROPRIETARY NAMES (OTHER NAMES) | DISEASE |
|---|---|---|---|
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; dimethyltriazenoimidazolecarboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU) Floxuridine (fluorode-oxyuridine; FUdR) | Breast, colon, stomach, pancreas, ovary, head and neck, urinary bladder, premalignant skin lesions (topical) |
| | | Cytarabine (cytosine arabinoside) | Acute granulocytic and acute lymphocytic leukemias |
| | Purine Analogs and Related Inhibitors | Mercaptopurine (6-mercaptopurine; 6-MP) | Acute lymphocytic, acute granulocytic and chronic granulocytic leukemias |
| | | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide Tertiposide | Testis, small-cell lung and other lung, breast, Hodgkin's disease, non-Hodgkin's lymphomas, acute granulocytic leukemia, Kaposi's sarcoma |
| Natural Products | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung and genitourinary tract; Hodgkin's disease, |

TABLE 4-continued

Chemotherapeutic Agents Useful In Neoplastic Disease

| CLASS | TYPE OF AGENT | NONPROPRIETARY NAMES (OTHER NAMES) | DISEASE |
|---|---|---|---|
| | | Plicamycin (mithramycin) | non-Hodgkin's lymphomas Testis, malignant hypercalcemia |
| | | Mitomycin (mitomycin C) | Stomach, cervix, colon, breast, pancreas, bladder, head and neck |
| | Enzymes | l-Asparaginase | Acute lymphocytic leukemia |
| | Biological Response Modifiers | Interferon alfa | Hairy cell leukemia., Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essental thrombocytosis, malignant melanoma |
| | Methyl Hydrazine Derivative | Procarbazine (N-methylhydrazine, MIH) | Hodgkin's disease |
| | Adrenocortical Suppressant | Mitotane (o,p'-DDD) | Adrenal cortex |
| | | Aminoglutethimide | Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstilbestrol Ethinyl estradiol (other preparations available) | Breast, prostate |
| | Antiestrogen | Tamoxifen | Breast |
| | Androgens | Testosterone propionate Fluoxymesterone (other preparations available) | Breast |
| | Antiandrogen | Flutamide | Prostate |
| | Gonadotropin-releasing hormone analog | Leuprolide | Prostate |

B. Radiotherapy

Other factors that cause DNA damage and have been used extensively include what are commonly known as □-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with Ad-Bik gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, the secondary treatment is a secondary gene therapy in which a second therapeutic polynucleotide is administered before, after, or at the same time a first therapeutic polynucleotide encoding all of part of a mutant form of Bik. Delivery of a vector encoding either a full length or truncated mutant form of Bik in conjunction with a second vector encoding one of the following gene products will have a combined anti-hyperproliferative effect on target tissues. Alternatively, a single vector encoding both genes may be used. A variety of proteins are encompassed within the invention, some of which are described below.

1. Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

2. Inhibitors of Cellular Proliferation

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently mutated gene in common human cancers. It is mutated in over 50% of human NSCLC (Hollstein et al., 1991) and in a wide spectrum of other tumors.

The p53 gene encodes a 393-amino acid phosphoprotein that can form complexes with host proteins such as large-T antigen and E1B. The protein is found in normal tissues and cells, but at concentrations which are minute by comparison with transformed cells or tumor tissue.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are known to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Another inhibitor of cellular proliferation is p16. The major transitions of the eukaryotic cell cycle are triggered by cyclin-dependent kinases, or CDK's. One CDK, cyclin-dependent kinase 4 (CDK4), regulates progression through the G1. The activity of this enzyme may be to phosphorylate Rb at late G1. The activity of CDK4 is controlled by an activating subunit, D-type cyclin, and by an inhibitory subunit, the p16INK4 has been biochemically characterized as a protein that specifically binds to and inhibits CDK4, and thus may regulate Rb phosphorylation (Serrano et al., 1993; Serrano et al., 1995). Since the p16INK4 protein is a CDK4 inhibitor (Serrano, 1993), deletion of this gene may increase the activity of CDK4, resulting in hyperphosphorylation of the Rb protein. p16 also is known to regulate the function of CDK6.

p16INK4 belongs to a newly described class of CDK-inhibitory proteins that also includes p16B, p19, p21Waf1/Cip1, and p27KIP1. The p16INK4 gene maps to 9Bik, a chromosome region frequently deleted in many tumor types. Homozygous deletions and mutations of the p16INK4 gene are frequent in human tumor cell lines. This evidence suggests that the p16INK4 gene is a tumor suppressor gene. This interpretation has been challenged, however, by the observation that the frequency of the p16INK4 gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type p16INK4 function by transfection with a plasmid expression vector reduced colony formation by some human cancer cell lines (Okamoto, 1994; Arap, 1995).

Other genes that may be employed according to the present invention include Rb, APC, DCC, NF-1, NF-2, WT-1, MEN-I, MEN-II, zac1, p'73, VHL, MMAC1/PTEN, DBCCR-1, FCC, rsk-3, p27, p27/p16 fusions, Bik/p27 fusions, anti-thrombotic genes (e.g., COX-1, TFPI), PGS, Dp, E2F, ras, myc, neu, raf, erb, fms, trk, ret, gsp, hst, abl, E1A, p300, genes involved in angiogenesis (e.g., VEGF, FGF, thrombospondin, BAI-1, GDAIF, or their receptors) and MCC.

3. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., BclXL, BclW, BclS, Mcl-1, A1, Bfl-1) or counteract Bcl-2 function and promote cell death (e.g., Bax, Bak, Bik, Bim, Bid, Bad, Harakiri).

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

Hormonal therapy may also be used in conjunction with the present invention or in combination with any other cancer therapy previously described. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

VI. Pharmaceutical Preparations

Pharmaceutical compositions of the present invention comprise an effective amount of one or more forms of mutant Bik or additional agent dissolved or dispersed in a pharmaceutically acceptable carrier or excipient. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one Bik mutant form or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated. In a specific embodiment, the mutant Bik composition is administered in a liposome.

The Bik mutant form may comprise different types of carriers depending on whether it is to be administered in solid, liquid or aerosol form, and whether it need to be sterile for such routes of administration as injection. The present invention can be administered intravenously, intradermally, intraarterially, intraperitoneally, intralesionally, intracranially, intraarticularly, intraprostaticaly, intrapleurally, intratracheally, intranasally, intravitreally, intravaginally, rectally, topically, intratumorally, intramuscularly, intraperitoneally, subcutaneously, intravesicularlly, mucosally, intrapericardially, orally, topically, locally, using aerosol, injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

The Bik mutant form may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

In other embodiments, one may use eye drops, nasal solutions or sprays, aerosols, mouthwashes, or inhalants in the present invention. Such compositions are generally designed to be compatible with the target tissue type. In a non-limiting example, nasal solutions are usually aqueous solutions designed to be administered to the nasal passages in drops or sprays. Nasal solutions are prepared so that they are similar in many respects to nasal secretions, so that normal ciliary action is maintained. Thus, in preferred embodiments the aqueous nasal solutions usually are isotonic or slightly buffered to maintain a pH of about 5.5 to about 6.5. In addition, antimicrobial preservatives, similar to those used in ophthalmic preparations, drugs, or appropriate drug stabilizers, if required, may be included in the formulation. For example, various commercial nasal preparations are known and include drugs such as antibiotics or antihistamines.

In certain embodiments the Bik mutant form is prepared for administration by such routes as oral ingestion. In these embodiments, the solid composition may comprise, for example, solutions, suspensions, emulsions, tablets, pills, capsules (e.g., hard or soft shelled gelatin capsules), sustained release formulations, buccal compositions, troches, elixirs, suspensions, syrups, wafers, or combinations thereof. Oral compositions may be incorporated directly with the food of the diet. Preferred carriers for oral administration comprise inert diluents, assimilable edible carriers or combinations thereof. In other aspects of the invention, the oral composition may be prepared as a syrup or elixir. A syrup or elixir, and may comprise, for example, at least one active agent, a sweetening agent, a preservative, a flavoring agent, a dye, a preservative, or combinations thereof.

In certain preferred embodiments an oral composition may comprise one or more binders, excipients, disintegration agents, lubricants, flavoring agents, and combinations thereof. In certain embodiments, a composition may comprise one or more of the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc.; or combinations thereof the foregoing. When the dosage unit form is a capsule, it may contain, in addition to materials of the above type, carriers such as a liquid carrier. Various other materials may be present as coatings or to otherwise modify the physical form of the dosage unit. For instance, tablets, pills, or capsules may be coated with shellac, sugar or both.

Additional formulations which are suitable for other modes of administration include suppositories. Suppositories are solid dosage forms of various weights and shapes, usually medicated, for insertion into the rectum, vagina or urethra. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle that contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

VII. Site-Directed Mutagenesis

Structure-guided site-specific mutagenesis represents a powerful tool for the dissection and engineering of protein-ligand interactions (Wells, 1996, Braisted et al., 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Brown et al., 1996; Zeng et al., 1996; Burton and Barbas, 1994; Yelton et al., 1995; Jackson et al., 1995; Short et al., 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Exemplary Materials and Methods

Cell Lines

Human breast cancer cell lines MCF-7, MDA-MB-231, MDA-MB-435, ovarian cancer cell line SKOV-ip1 and the human prostate carcinoma cell line PC-3 were purchased from the American Type Culture Collection (Rockville, Md.) and cultured according to the vendor's instructions.

Plasmids Construction and Site-Directed Mutagenesis

Bik, Luc, and GFP-expressing plasmids were constructed by inserting the cDNAs of Bik, Luc, and GFP, respectively, into the pcDNA3 vector containing a cytomegalovirus promoter. Site-directed mutagenesis was performed according to the manufacturer's protocol (Clontech Inc.). Bik residues threonine 33 and serine 35 aspartate by using the following primers: for T33D, 5'-GGCATGACTGACGATGAAGAGGACCTG-3' (SEQ ID NO:1), and for S35D, 5'-GTTCTTGGCATGGATGACTCTGAACAGG-3' (SEQ ID NO:2). The sequences of three Bik mutant constructs were verified by automated sequencing.

Formulation

The non-viral gene delivery system, termed SN, was essentially a cationic liposome, which is formulated as described previously (Zou et al., 2002).

Transfection

Cells were cultured for 24 h in six-well plates with 1 ml/well of DMEM/F12 medium with 10% FBS (Life Technologies, Inc., Gaithersburg, Md.) until 60-70% confluence was reached. The liposomal DNA (SN-DNA) was directly added into the culture plates at a ratio of 2 μg of DNA/106 cells. Twenty-four h later, the transfection efficiency was determined by counting the GFP-positive cells under a fluorescence microscope and expressing the result as a percentage of total cells. Six random fields with >200 cells/field were counted for each sample. All experiments were repeated three times independently.

Western Blot Analysis

Protein lysate was prepared with RIPA-B cell lysis buffer containing 20 mM Na2PO4 (pH 7.4), 150 mM NaCl, 1% Triton X-100, 100 mM NaF, 2 mM Na3VO4, 5 mM phenylmethylsulfonyl fluoride, 1% aprotinin, and 10 μg/ml leupeptin. Goat anti-Bik polyclonal antibody was perchanced from Santa Cruz Biotechnology (Santa Cruz, Calif.). Donkey anti-goat IgG peroxidase (Jackson) was used as secondary antibody. Western blots were developed by enhanced chemiluminescence (ECL; Amersham).

Luciferase Assays

To determine the Bik dose effect on cell proliferation, different cancer cells were co-transfected with 50 ng of CMV-luc and an increasing amount (0, 0.5, or 2 μg) of CMV-Bik. The total amount of DNA transfected at each dose was kept constant (2.05 μg) by adding an appropriate amount of pcDNA3 vector. Forty-eight hrs after transfection, cells were harvested, and luc activity was measured using the luc assay system (Promega) according to the protocol supplied by the manufacturer. The relative activities were calculated by setting the luc activities obtained from transfections without CMV-Bik (0 μg) at 100%. The data represent mean±SD of three independent experiments.

Apoptosis Assay

For in vitro studies, standard fluorescence-activated cell sorter analysis was used to determine the apoptosis of the cells. Briefly, the cells were transfected with SN-bik or other agents. 12 or 24 hrs after transfection, the apoptotic cells were assessed by flow cytometric detection of sub-G1 DNA content after being stained with propidium iodide. Fields with >2000 cells in each were randomly selected, and the apoptotic versus nonapoptotic cells were counted.

Ex Vivo Tumor Inhibition

Human breast cancer cell line MCF-7 and prostate cancer cell lines PC-3 cells were transfected by SN-bik or SN-luc. Twenty-four h after transfection, the cells were carefully trypsinized, harvested, and inoculated into the MFPs of nude mice (2×106 cells/tumor). The volume of the resulting tumor was measured weekly.

Anti-Tumor Activity Tests

To study tumor growth inhibition, female nude mice were inoculated with 2×106 of breast cancer cells/tumor into the MFPs. Two weeks later, when most tumors exceeded 4×4 mm, the tumor-bearing mice were randomly divided into three groups with 5 mice in each group. The mice in all treatment groups received i.v. injections of SN-bik three times a week for 3 weeks, at a dose of 15 μg of DNA/mouse. The mice in control groups were injected with the same dose of SN-luc or the same volume of PBS. The tumor volume was measured weekly. To assess animal survival and the increase in life span, the same tumor models and the same therapeutic treatments were used. The experiment was terminated on day 200 after tumor inoculation.

Statistical Analysis

All statistical tests used in this study are two-sided log-rank statistical tests.

Example 2

Construction of Exemplary Bik Mutants

The Bik single mutant T33D, S35D and double mutant T33DS35D, in which the residues 33 (threonine) and 35 (serine) were changed to aspartate acid residues respectively or together, were constructed by site-directed mutagenesis (Clontech; La Jolla, Calif.). After confirming the mutant Bik constructs by DNA sequencing, Western blot with a Bik antibody demonstrated production of the different Bik mutants expressed in HBK293 cell after transient transfection. A formulation of cationic lipid (SN) was used to deliver the pro-apoptotic mutant Bik gene into different human cancer cells in vitro and in vivo (Zou et al., 2002).

Example 3

In Vitro Testing of Exemplary Bik Mutants

To test whether the Bik mutants inhibited human cancer cell line growth in vitro better than wide type Bik, transient transfection assay was performed to evaluate the cell growth inhibition effect of mutant Bik, in which a fixed amount (50 ng) of CMV-luc was co-transfected with an increasing amount (0, 0.5, and 2 μg) of CMV-Bik wide type and mutants in different human cancer cells, including human breast cancer cell lines MDA-MB-231, MDA-MB-468, MCF-7, prostate cancer cell line PC-3 and ovary cancer cell line SKOV-ip1. Because the apparent luc activity is indicative of living cells, the relative luciferase activity could be used as the index of cell growth and proliferation (FIG. 1).

In FIG. 1A, western blot analysis of Bik and mutants protein expression after transient transfection in 293T cells is shown. Actin was used as an equal loading control. In FIGS. 1B through 1F, human breast cancer cell lines MDA-MB-468 (FIG. 1B), MCF-7 (FIG. 1C), MDA-MB-231 (FIG. 1D), ovary cancer cell line skov-ip1 (FIG. 1E) and prostate cancer cell line PC-3 (FIG. 1F) were cotransfected with 50 ng of CMV-luc and an increasing amount (0, 0.5, or 2 μg) of CMV-Bik wide type or mutants. The relative activities were calculated by setting the luciferase activities obtained from transfections without CMV-Bik (0 μg) at 100%. The data represent means of three independent experiments; bars, SD; stars (*) mean significant difference, compared with wide type (P<0.05).

While the wild type and mutant Bik expression caused overall growth inhibition in a dose-dependent manner, the Bik mutants, especially the T33DS35D mutant, exhibited stronger growth inhibitory effect on different cancer cells, and the expression level was proportional to the growth-inhibitory activity. Thus, mutant Bik is very potent against numerous cancer cell types both in vitro and in vivo. Its effect is independent of the expression level of Her-2/neu oncogene.

Figure 2:
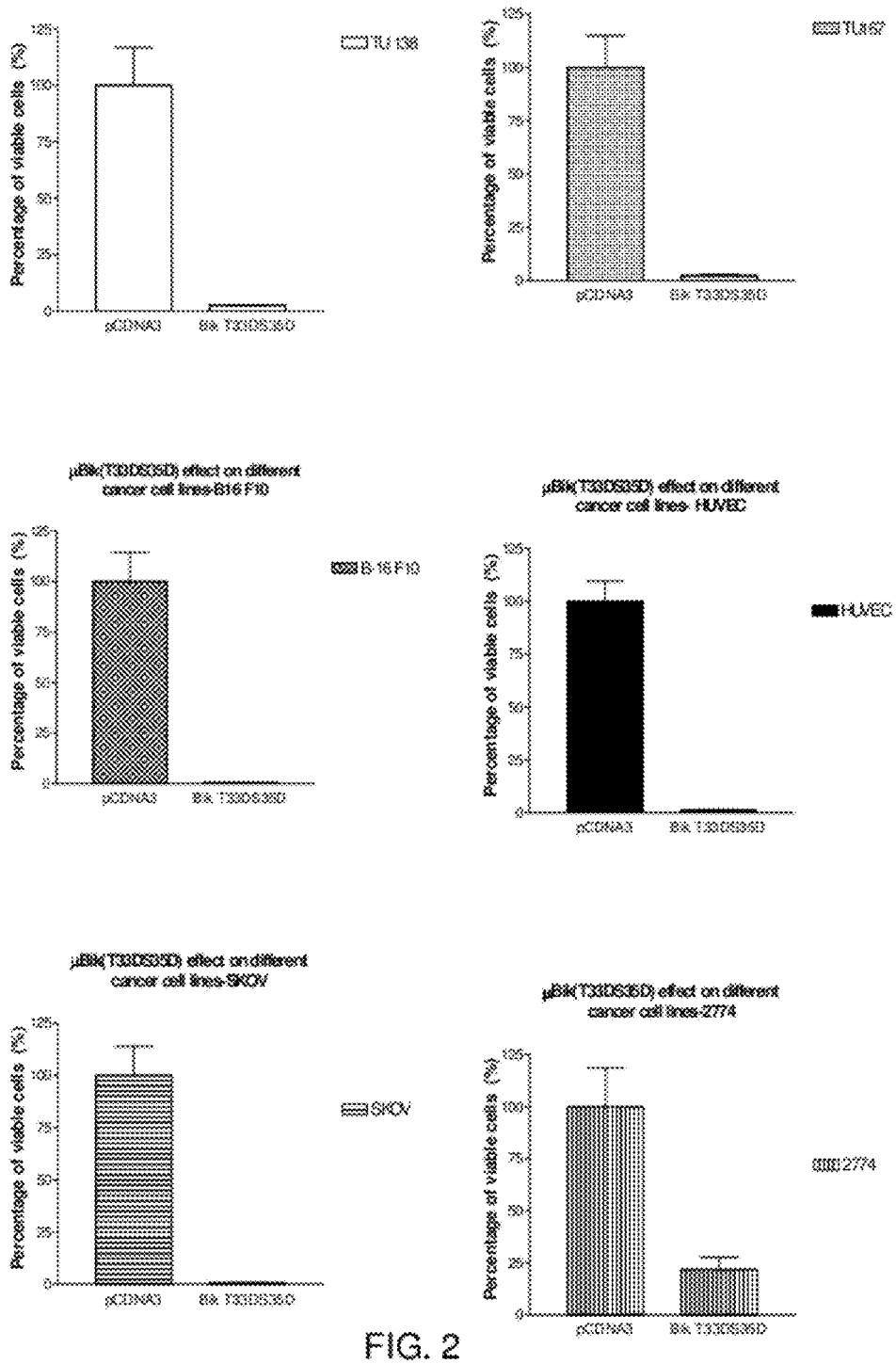
FIG. 2 shows that the Bik mutants exhibited stronger cell-killing effect in different human cancer cell lines.

Using similar methods, and as illustrated in FIG. 2, Bik mutant T33DS35D also exhibits potent anticancer effect on head and neck cancer cells (TU138 and TU167), melanoma (B16F10), ovarian (2774 and SKOV. SKOV is not a Her-2/neu overexpressing cell, as opposed to SKOV-ip1), and endothelial cells (Human umbilical vascular endothelial cells, HUVEC). Thus, in addition to SKOV-ip1, which is a Her-2/neu overexpressing cancer cell, the bik mutants also demonstrate potent inhibitory effects on cells without Her-2/neu overexpression.

Example 4

FACS Analysis of Activity of Bik Mutants

The pro-apoptotic gene Bik is known to elicit apoptosis in a variety of malignant cells. To examine whether the mutant Bik will cause improved cell-killing effect or apoptosis on different cancer cells, standard fluorescence-activated cell sorter analysis (FACS) was used to assay apoptosis of the cancer cells. Briefly, the cells were transfected with SN-Bik or other agents.

Specifically, human breast cancer cell lines MCF-7 and prostate cancer cell line PC-3 were cotransfected with 100 ng of CMV-GFP and 2 µg of CMV-Bik wide type or mutants. pcDNA3 transfected cells were used as control. Twelve or twenty-four hours after transfection, the apoptotic cells were harvested and assessed by flow cytometric detection of sub-G1 DNA content after being stained with propidium iodide. The data represent means of three independent experiments; bars, SD; stars (*) mean significant difference, compared with wide type ($P<0.05$).

Figure 3:
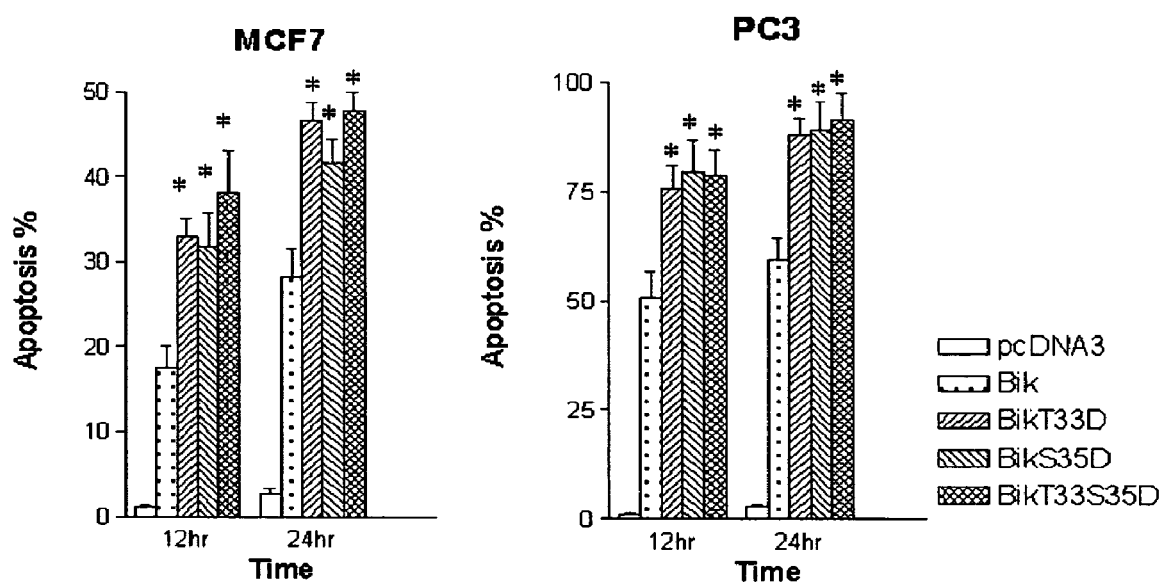
FIG. 3 illustrates that the Bik mutants exhibit strong cell-killing in additional human cancer cell lines.

Twelve or twenty-four hours after transfection, the apoptotic cells were assessed by flow cytometric detection of sub-G1 DNA content after being stained with propidium iodide. In the MCF-7 cell, the different Bik mutants-induced 40% to 80% more apoptosis than the wild type Bik (FIG. 3). The onset of apoptosis was also early than the wild type, as early as 8 h after the transfection. In the PC-3 cell lines similar phenomena was also observed. The results indicate that mutant Bik can induce significant cancer cell apoptosis, stronger and earlier than the wt Bik.

Example 5

Ex Vivo Testing of Exemplary Bik Mutants

One of the most critical biological properties for a tumor suppressor gene is its ability to reduced tumorigenicity in vivo. To test the possibly better anti-tumor activity of different Bik mutants, an ex vivo tumorigenicity assay was performed in a nude mice cancer model. Human breast cancer cell lines MCF-7 and prostate cancer cell line PC-3 were transfected with CMV-Bik wild type or mutants delivered by SN liposome in culture plates. pcDNA3 transfected cells were used as control. Twenty-four hours later, the treated cells were carefully harvested and inoculated into the mammary fat pads (mfp) (for MCF-7) or subcutaneous connective tissue (for PC-3) of nude mice. Four million cells were inoculated for MCF-7 and one million cells for PC-3. Empty vector pcDNA3-transfected cells were used as a control. The inoculated tumor size was measured weekly.

Specifically, human breast cancer cell lines MCF-7 ($4\times10^6$ cells, each mouse implanted 0.72 mg 17 β-estradiol pellet subcutaneously 2 weeks before inoculation) and prostate cancer cell line PC-3 ($1\times10^6$ cells) were transfected with CMV-Bik wide type or mutants delivered by SN liposome in culture plates. pcDNA3 transfected cells were used as control. Twenty-four hours later, the treated cells were harvested and inoculated in the mammary fat pads (mfp) (for MCF-7) or subcutaneous connective tissue (for PC-3) of nude mice, with 8 mice in each group. Tumor sizes were measured weekly, as showed in FIG. 4A. After 7 weeks, the mice were scarified and the tumor weight were measured as showed in FIG. 4B. In the each group, there was tumor-formatting rate. bars, SD; stars (*) denote mutants having significant difference, compared with wide type ($P<0.05$); stars (**) denote wild type Bik having significant difference, compared with pcDNA3 control ($P<0.05$).

Figure 4A:
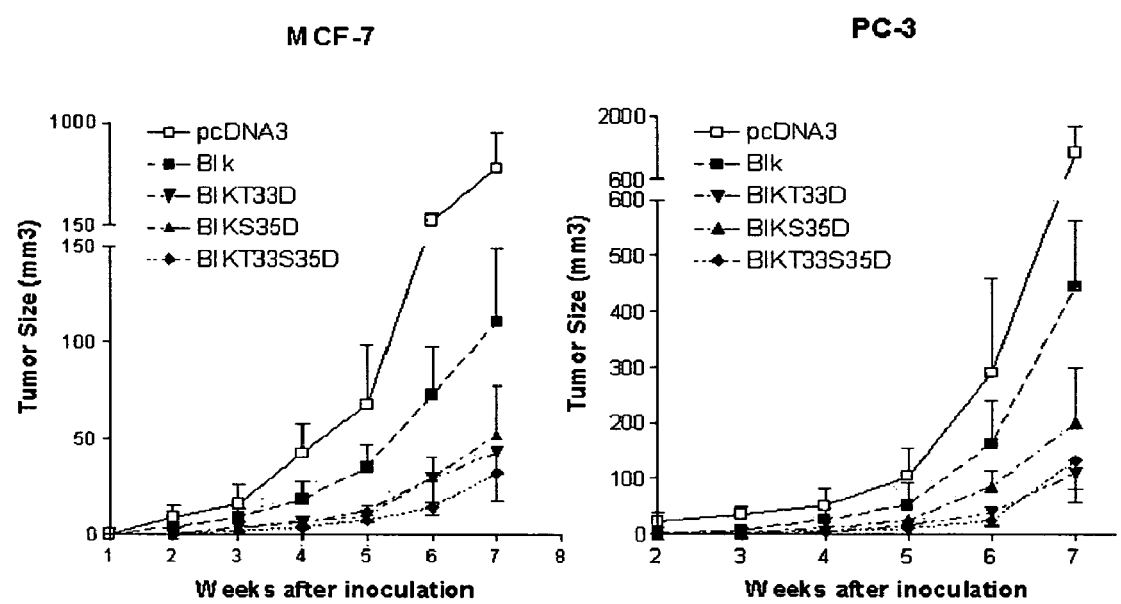
FIGS. 4A through 4B illustrate that the Bik mutants exhibited stronger tumor suppression effect in ex vivo assay.
Figure 4B:
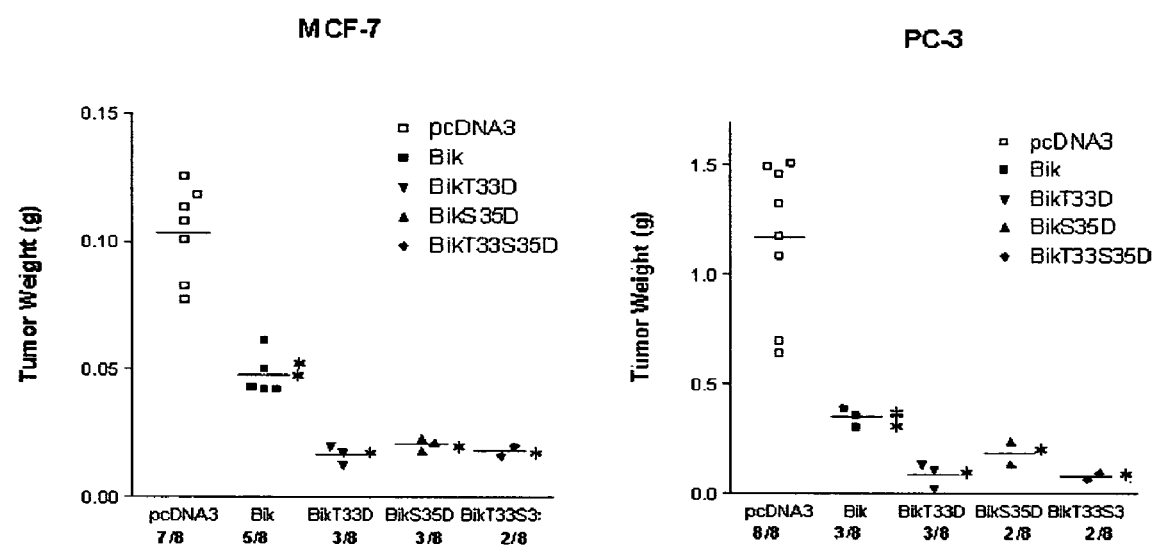

This "ex vivo test" bypassed the gene delivery problems in vivo and showed that under the optimal gene delivery condition, tumor cells with mutant Bik had less tumor growth ability than wide type Bik in vivo (FIG. 4A). SN-Bik delayed tumor growth in mice by at least 3 weeks compared with the pcDNA3 control. The tumor volume ratios of wt Bik versus 3 Bik mutants treatment groups during weeks 7 ranged from 2.1 to 3.7 for MCF-7 cell and from 2.2 to 4.1 for PC-3 cell, suggesting a strong tumor suppression activity by mutant Bik treatment in vivo. The data in FIG. 4 represent the mean±standard deviation of tumors size of 8 mice in each group. Furthermore, the average tumor size (measured by weight) of the wt Bik was about 2 to 4 folds than that of different Bik mutant groups (FIG. 4B). In MCF-7 group, mutant Bik also had less tumor taking-rate.

Example 6

In Vivo Testing of Exemplary Bik Mutants

The above studies showed that three mutant Bik forms could induce apoptosis and inhibit tumor cell growth better than wild type Bik in vitro and ex vivo, and the anti-tumor activity of SN-delivered Bik mutants was further compared with wt Bik in orthotopic breast cancer model and subcutaneous prostate cancer model.

Because the double mutant T33DS35D Bik is the strongest mutant of the three Bik mutants in apoptosis assay in vitro and tumor growth ex vivo assay, the Bik T33DS35D (Bik DD) was used as a representative of the three Bik mutants to compare with the wt Bik in the following in vivo study. Mice with established tumors were then treated with SN-wt Bik, SN-Bik T33DS35D or SN-pcDNA3. SN-Bik T33DS35D injection significantly inhibited tumor growth in mice compared with the SN-Bik and SN-pcDNA-treated mice.

Figure 5A:
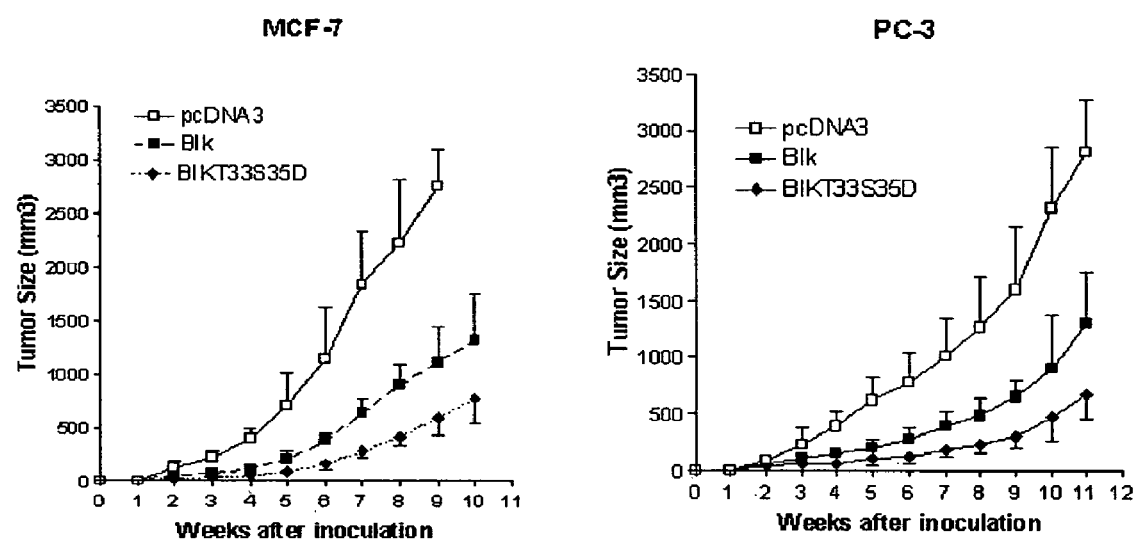
FIGS. 5A through 5B demonstrate that the mutant Bik gene delivered by SN significantly inhibited growth of human tumors in mice.
Figure 5B:
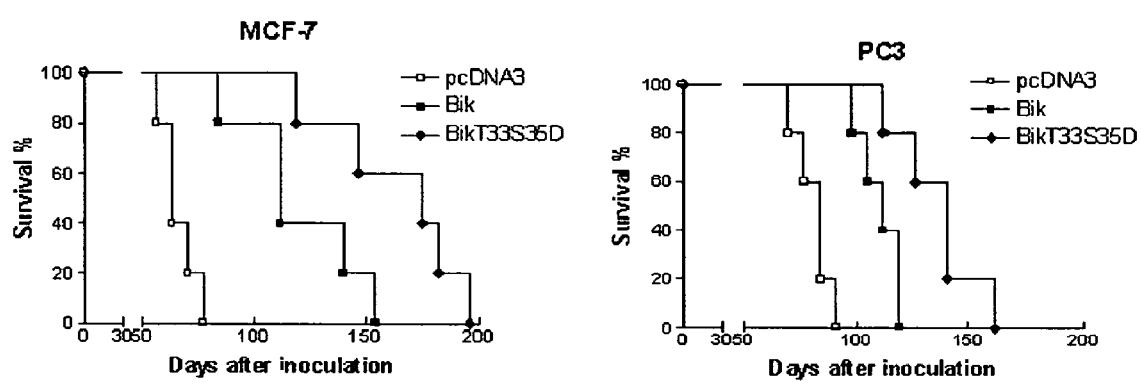

Specifically, in FIG. 5A, orthotopic human breast cancer MCF-7 cell (mammary fat pads, 4×106 cells/mouse, each mouse implanted 0.72 mg 17 β-estradiol pellet subcutaneously 2 weeks before inoculation) and ectopic human prostate cancer PC3 cell (subcutaneous, 1×106 cells/mouse) models in mice were used. One week later, the mice bearing tumors were randomly divided into three groups with 5 mice in each. One group received multiple injections of SN-DNA, 15 µg DNA/mouse, three times a week for a total of 12 treatments, orthotopic breast cancer by intravenous injection and ectopic prostate cancer by intra-tumor injection, the other group received same doses of SN-pcDNA3. The tumor volume was measured weekly. In FIG. 5B, the mutant Bik gene delivered by SN significantly prolonged the life of mice with orthotopic or ectopic human cancer. The data shown in the FIG. represent the mean±standard deviations from 5 individual mice. Bars, S. Dak.)

By weeks 3 to 5, the mean tumor volume of SN-Bik-treated mice was higher than that of SN-Bik T33S35D-treated mice in two models. The most significant tumor suppression effect could be observed by week 8 and 9, with an approximate 2-3-fold difference in tumor volumes between the wide type and mutant treatment groups (P<0.05; FIG. 5A). Treatment by SN-Bik T33S35D significantly increased the survival rate of the treated mice compared with the control groups treated with SN-wt Bik (P<0.05; FIG. 5B). The median survival time was 175 days for Bik T33S35D treatment vs. 112 days for Bik in MCF-7 cells, 140 days vs. 105 days in PC3 cells. The results indicate that SN-Bik T33S35D inhibited about 50% of the tumor growth in these human cancer models and significantly increased the survival rates.

A systemic gene therapy approach for breast cancer was developed, consisting of a nonviral gene delivery system (SN) and a proapoptotic gene, bik. The SN-Bik gene complex induced significant apoptosis in four breast cancer cell lines in vitro as well as in orthotopic tumor tissues in nude mice (Zou et al., 2002). Systemically administered SN-Bik significantly inhibited the growth and metastasis of human breast cancer cells implanted in nude mice and prolonged the life span of the treated animals. The Bik gene is a potent inducer for apoptosis, independent of p53. Like Bad (Wang et al., 1999) and Bid (Desagher et al., 2001), Bik is regulated by phosphorylation (residues threonine 33 and serine 35) Unlike Bad, phosphorylation increases the pro-apoptotic potency of Bik. The mechanism is presently unknown, possibly by a casein kinase II-related enzyme (Verma et al., 2000). The phosphatase PP2A might negatively regulate its function (Klumpp and Krieglstein, 2002). The post-translational phosphorylation of Bik, in specific embodiments, results in conformational changes to cause release from an inactive complex and increased affinity or accessibility to antiapoptotic Bcl-2 homologues.

The results showed that transfection of Bik mutants (T33D, S35D and T33DS35D) was much more potent than wild type (wt) Bik to inhibit cell proliferation and enhance apoptosis induction of various human cancer cells and to inhibit tumor growth in mice in ex vivo and in vivo models. Thus, this shows that mutant Bik gene is more potent than wt Bik to induce cell death, and SN-Bik is useful for a therapeutic agent of cancer.

Obviously, methods disclosed herein have proven useful for specific Bik mutants in the context of the invention. Following the teachings provided herein, one of skill in the art can prepare and test any number of mutants for anti-cell proliferative activity, antitumor activity, pro-apoptotic activity, or a combination thereof.

Example 7

Testing of Exemplary Bik Mutants as Therapeutic Agents

Bik mutants as they relate to anti-tumor activity are tested in an animal study, such as cell lines, cell culture, and/or models in addition to or other than those described in the preceding Examples. In general embodiments of the present invention, mutants are delivered by a vector, such as a liposome, adenoviral vector, or combination thereof, into nude mice models for their anti-tumor activity. Once the anti-tumor activity is demonstrated, potential toxicity is further examined using immunocompetent mice, followed by clinical trials.

In a specific embodiment, the preferential growth inhibitory activity of mutant Bik is tested in animal. Briefly, cancer cell lines are administered into mammary fat-pad of nude mice to generate a breast xenografted model. Although, as described herein, any cancer cell is within the scope of the present invention irrespective of its genotype or expression levels, (such as, for example, whether it is HER-2/neu-positive or HER-2/neu-negative), in a specific embodiment HER-2/neu overexpressing breast cancer cell lines (such as, for example, SKBR3 and/or MDA-MB361) are utilized, such as for testing. After the tumors reach a particular size, the Bik mutant and/or wild-type Bik control is administered into the mouse, such as, for example, intravenously injected in an admixture with an acceptable carrier, such as liposomes. The tumor sizes and survival curve from these treatments are compared and statistically analyzed. In a preferred embodiment, the mutant Bik is substantially the same as or better in its inhibition of the growth of tumor compared to that of wild-type Bik.

Example 8

Preparation of Additional Bik Mutants

Based on the data in previous Examples and the teachings elsewhere in the specification, in addition to the knowledge in the art, a skilled artisan would be motivated and capable of generating additional Bik mutants and, furthermore, able to determine the usefulness in the context of the invention using methodology disclosed herein.

Example 9

Testing of Additional Bik Mutants

Once Bik mutants other than the exemplary mutants disclosed herein are generated, testing using a cell culture in a relevant cell line(s) is performed, such as described herein. Furthermore, testing of the Bik mutants using FACS analysis is performed, such as described herein. Also, testing of the additional Bik mutants using ex vivo systems or in vivo systems as described herein may be employed, in specific embodiments.

Example 10

Figure 6A:
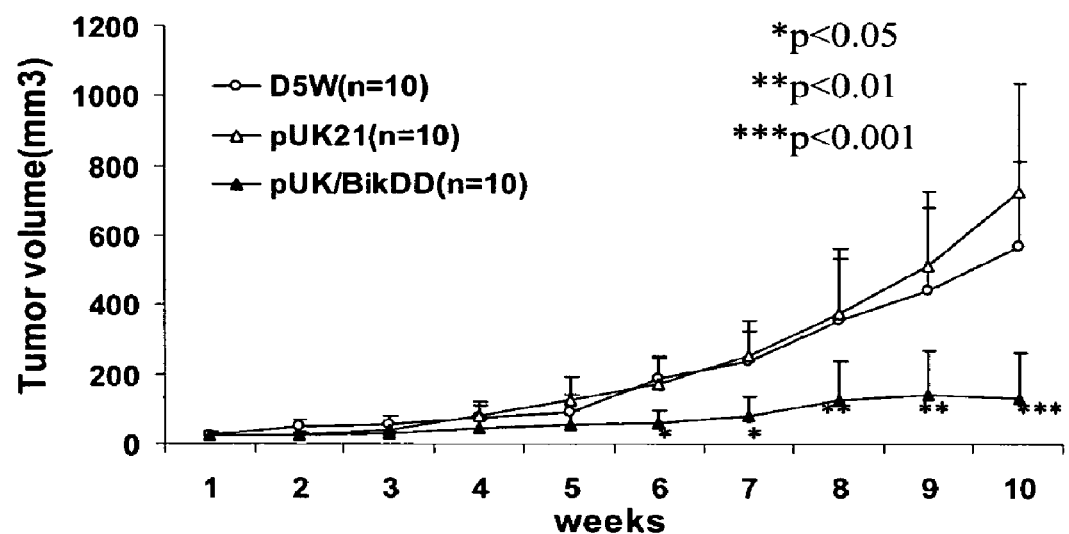
FIGS. 6A and 6B show that an exemplary Bik mutant (BikDD) polynucleotide demonstrated a significant suppression of tumor growth and an increase in survival in a breast cancer orthotopic model.
Figure 6B:
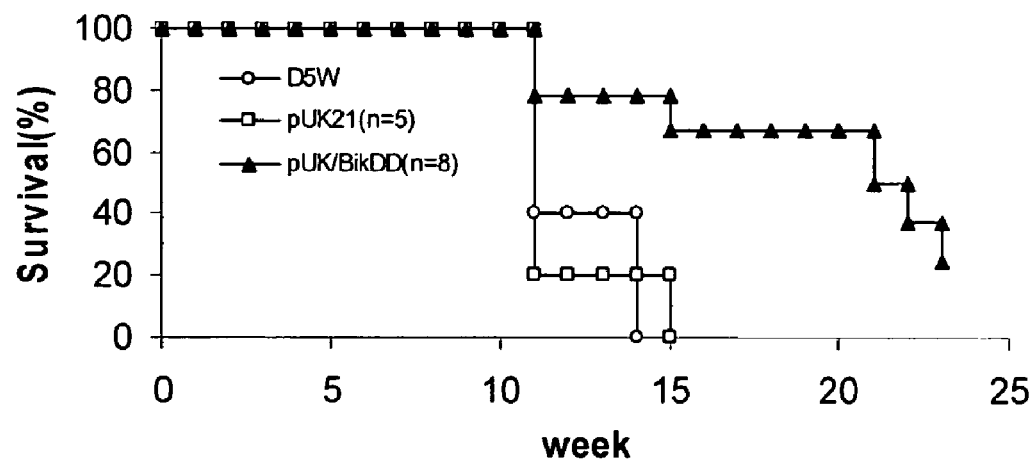

Anti-Cancer Effect of Mutant Bik in Breast, Ovarian and Pancreatic Cancer Models An exemplary Bik mutant (BikDD) polynucleotide demonstrated a significant suppression of tumor growth and an increase in survival in a breast cancer orthotopic model. Human breast cancer cells MDA-MB-231 ($2\times10^6$ cells) were inoculated into the mammary fat pads (MFP) of nude mice. After 1 week, the mice bearing tumors were randomly divided into five groups with 5 or 8 mice in each group. The mice in all treatment groups received weekly i.v. injections of the either vector (pUK21) or BikDD (pUK/BikDD) (15 µg DNA/mouse) delivered using the NIH-liposome for ten weeks. The mice in the control group received injections of 5% Dextrose (D5W). In FIG. 6A, tumor volume was measured and recorded weekly. FIG. 6B shows that BikDD increased the survival rate of mice bearing MDA-MB-231 orthotopic tumors. The data shown in the FIGS. 6A and 6B represent the mean and standard deviations from 5 or 8 individual mice.

Figure 7A:
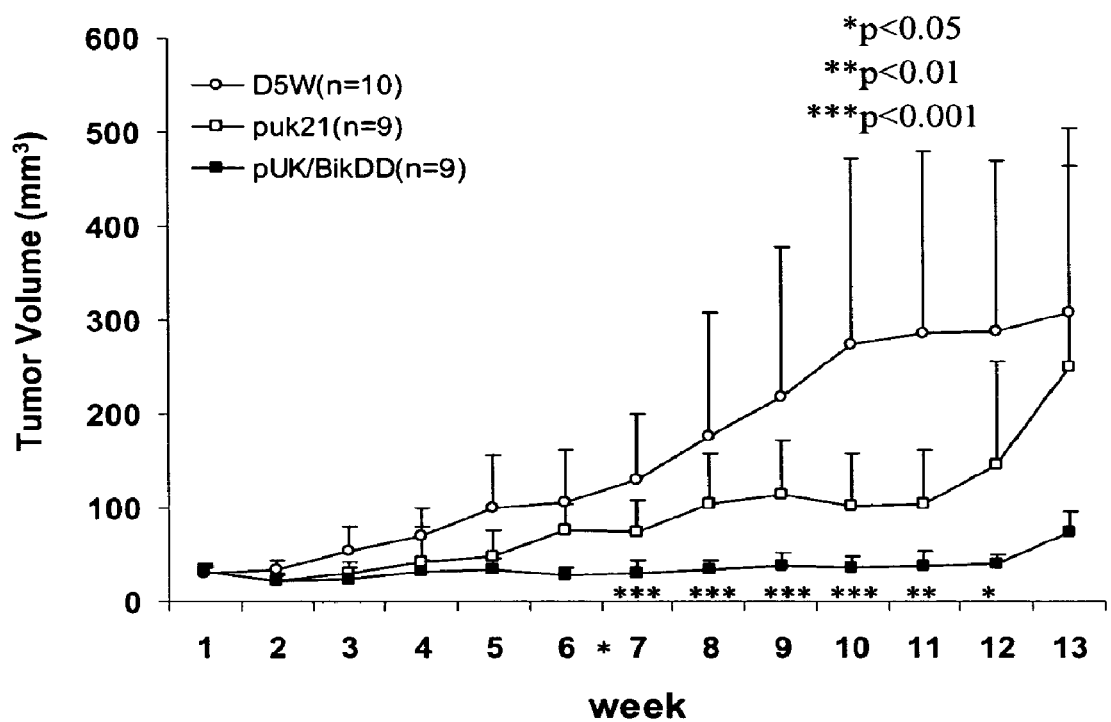
FIGS. 7A and 7B show that the Bik mutant (BikDD) gene demonstrated a significant suppression of tumor growth and an increase in survival in a breast cancer orthotopic model.
Figure 7B:
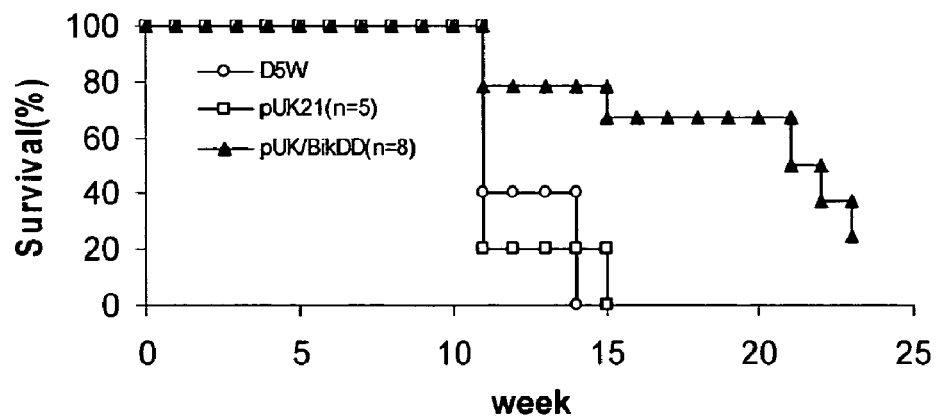

Also, the Bik mutant (BikDD) gene demonstrated a significant suppression of tumor growth and an increase in survival in a breast cancer orthotopic model. Human breast cancer cells MDA-MB-468 ($3\times10^6$ cells), were inoculated into the mammary fat pads (MFP) of nude mice. After 1 week, the mice bearing tumors were randomly divided into five groups with 9 or 10 mice in each group. The mice in all treatment groups received weekly i.v. injections of the either vector (pUK21) or BikDD (pUK/BikDD) (45 µg DNA/mouse) delivered using the NIH-liposome for ten weeks. The mice in the control group received injections of 5% Dextrose (D5W). In FIG. 7A, tumor volume was measured and recorded weekly. In FIG. 2B, BikDD increased the survival rate of mice bearing MDA-MB-231 orthotopic tumors. The data shown in the FIGS. 7A and 7B represent the mean and standard deviations from 9 or 10 individual mice.

Figure 8:
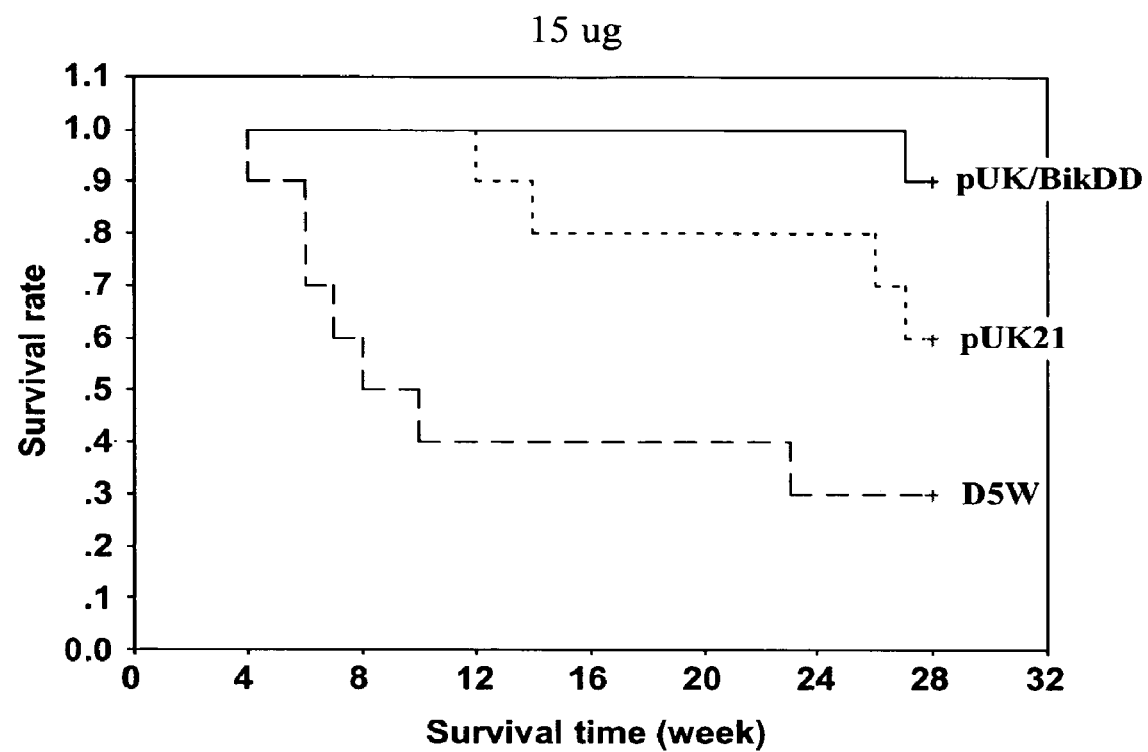
FIG. 8 shows that treatment with the Bik mutant (BikDD) gene increases the survival of mice in a ovarian cancer orthotopic model.

In FIG. 8, treatment with the Bik mutant (BikDD) gene increases the survival of mice in a ovarian cancer orthotopic model. Human ovarian cancer cells, 2774 ($2\times10^6$ cells), were inoculated intraperitononeally (i.p.) into nude mice. The mice were randomly split into 3 groups of ten mice each. The mice in all treatment groups received weekly i.p. injections of the either vector (pUK21) or BikDD (pUK/BikDD) (15 µg DNA/mouse) delivered using the NIH-liposome for twelve weeks. The mice in the control group received injections of 5% Dextrose (D5W). The data shown in the figures represent the mean and standard deviations from 10 individual mice.

Figure 9:
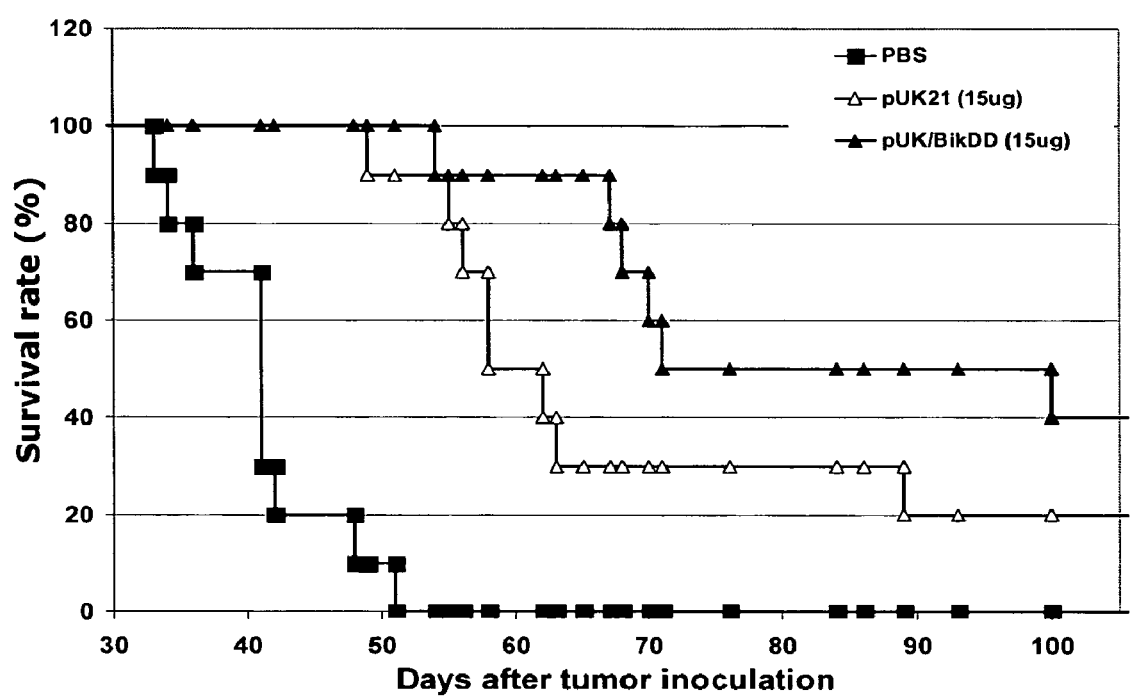
FIG. 9 demonstrates that treatment with the Bik mutant (BikDD) gene increases the survival of mice in a pancreatic cancer orthotopic model.

In FIG. 9, treatment with the Bik mutant (BikDD) gene increases the survival of mice in a pancreatic cancer orthotopic model. Pancreatic cancer cells, Pan02 ($5\times10^4$ cells), were inoculated into nude mice. The mice were randomly split into 3 groups of ten mice each. The mice in all treatment groups received weekly i.p. injections of the either vector (pUK21) or BikDD (pUK/BikDD) (15 µg DNA/mouse) delivered using the NIH-liposome for eleven weeks. The mice in the control group received injections of PBS.

Example 11

Cancer Tissue-Specific Expression of Mutant Bik

Current cancer therapies, such as chemotherapy (CT) and radiotherapy, have low selectivity for tumor cells and side effects for normal tissues. To minimize the side effects, these therapies are generally given in an intermittent manner, allowing normal cells to recover between treatment cycles. However, during the recovery period, some surviving cancer cells become more resistant to the treatment because of gene mutation. Consequently, cancer recurrence or progression may occur. Tumor-targeting gene therapy can minimize treatment side effects and the risk of developing resistance by acting on the tumor-specific signaling pathways. In the present invention, tissue-specific promoters are used for targeting gene therapy of mutant Bik, such as for breast cancer, pancreatic cancer, and prostate cancer.

Breast Cancer-Specific Expression of Mutant Bik

Breast cancer-specific expression of mutant Bik employs two exemplary promoters that are described herein and presented in further detail in U.S. Provisional Patent Application 60/559,111, entitled "Cancer-Specific Promoters" by Mien-Chie Hung, Yan Li, Yong Wen, Chi-Ping Day, Kun-Ming Rau, Xiaoming Xie, Zheng Li, filed simultaneously herewith and incorporated by reference herein in its entirety.

Topoisomerase IIα Breast Cancer-Specific Expression

Figure 10:
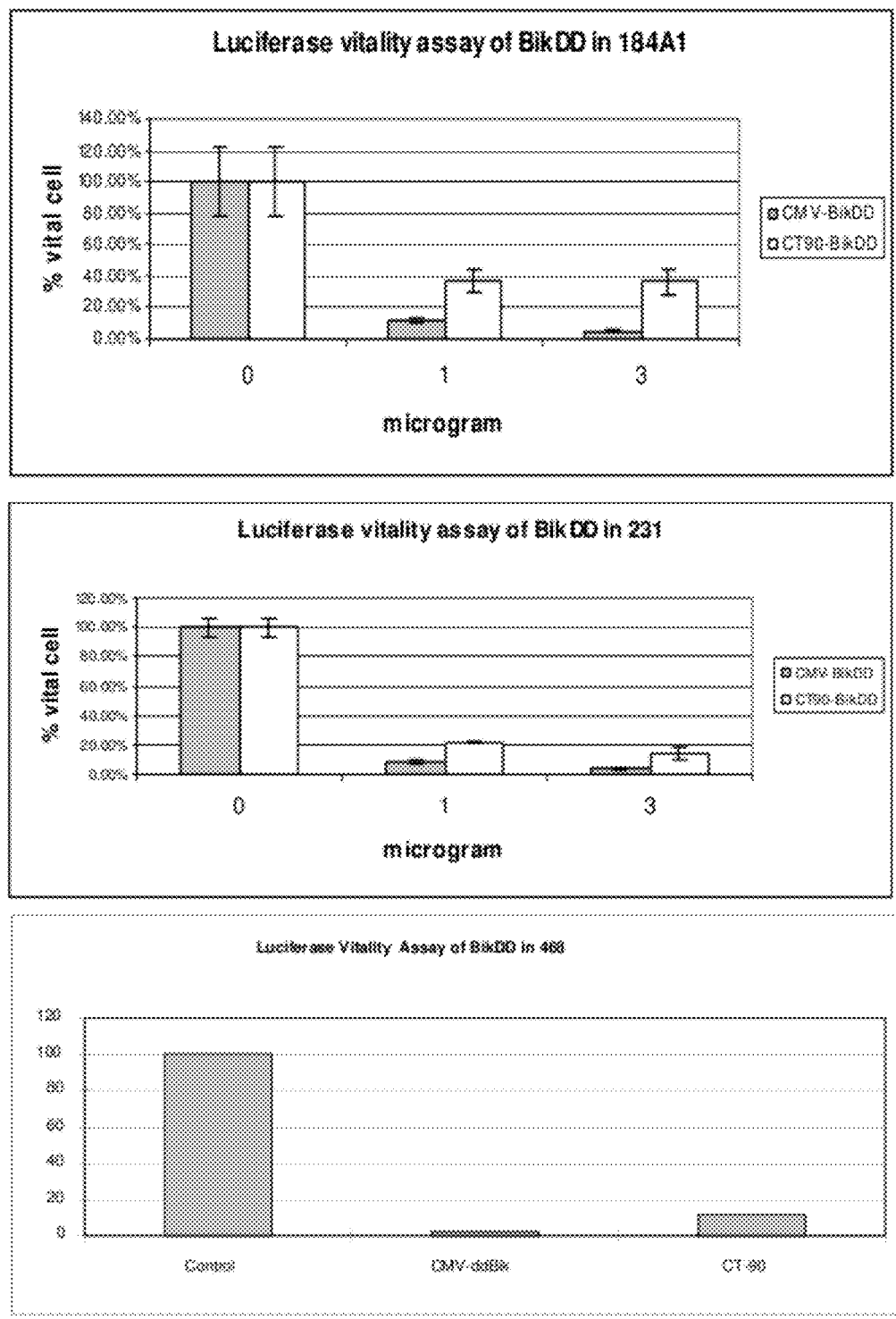
FIG. 10 shows in vitro killing assay of CT90BikDD and CMV-BikDD in different cell lines. The Y-axis value indicates the percentage of vital cells after treatment.

A therapeutic construct was generated that comprises topoisomerase IIα control sequence, such as the CT90 region (SEQ ID NO:26), that was operatively linked to CMV enhancer (SEQ ID NO:25), and the composite construct comprising both sequences (SEQ ID NO:37) was operatively linked to a polynucleotide encoding mutant Bik to regulate its expression. The construct is detailed herein but described further in U.S. Provisional Patent Application 60/559,111, entitled "Cancer-Specific Promoters" by Mien-Chie Hung, Yan Li, Yong Wen, Chi-Ping Day, Kun-Ming Rau, Xiaoming Xie, Zheng Li, filed simultaneously herewith and incorporated by reference herein in its entirety. A particular mutant Bik construct comprising sequence encoding the BikDD mutant is hereinafter referred to as CT90-BikDD. This construct was co-transfected with a luciferase reporter vector into breast cancer cell lines MDA-MB-231 and 468, and the normal breast epithelium cell line 184A1, and then the cell-killing effect was determined by a luciferase vitality assay. The CMV promoter-driven BikDD vector (CMV-BikDD) and empty vector were used as positive and negative controls, respectively. While CMV-BikDD killed all three cell lines to a nearly equal extent, CT90-BikDD killed breast cancer cells preferentially (FIG. 10), indicating that the killing effect of CT90-BikDD is selective for breast cancer cells. Therefore, CT90 is useful in breast cancer-targeting gene therapy.

Figure 11:
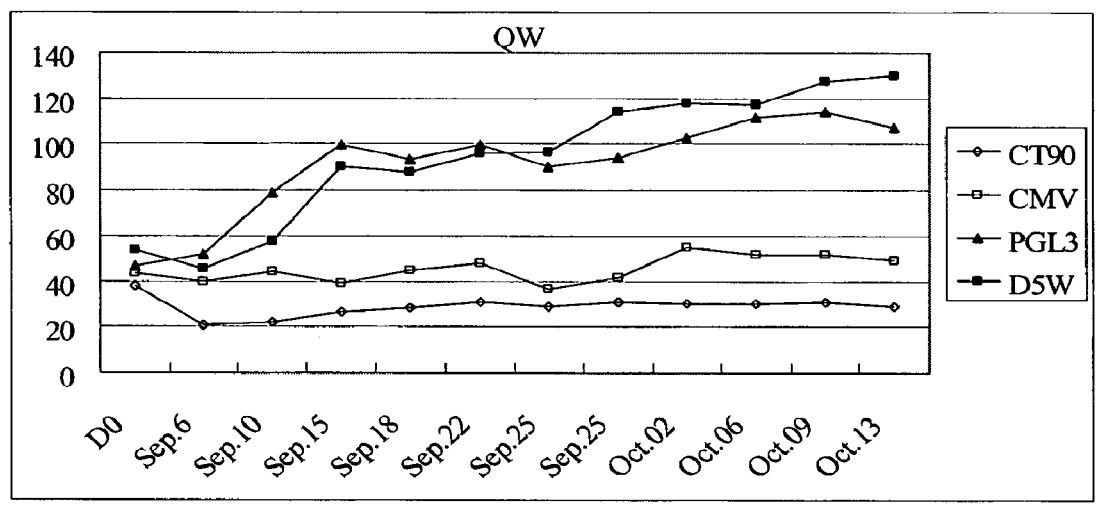
FIG. 11 shows in vivo anti-tumor effect of CT90-BikDD gene therapy. Breast cancer cell line MDA-MB-231 was inoculated 2.5×106 per mouse and mice were treated once per week by liposome-complexed CT0-BikDD, CMV-BikDD, empty vector pGL3, and dextrose buffer D5W as no-treatment control. Tumor size (Y-axis value) was measured twice per week during treatment and showed in the figure. The X-axis indicates the treatment dates.

Next, the anti-tumor effect of this breast cancer-targeting gene therapy was characterized in vivo. One week after inoculating breast cancer MDA-MB-231 cells into mammary fat pads, the nude mice were treated once per week with liposome-complexed CT90-BikDD (therapeutic group), CMV-BikDD (positive control), and CMV-PGL3 (mock treatment), or dextrose buffer D5W as a no-treatment control. Each mouse was intravenously injected with 15 □g of liposome-complexed DNA construct, once per week, and tumor size was measured regularly. The CT90-BikDD group showed a superior tumor suppressive effect compared to CMV-BikDD or CMV-PGL3 (FIG. 11).

Figure 12A:
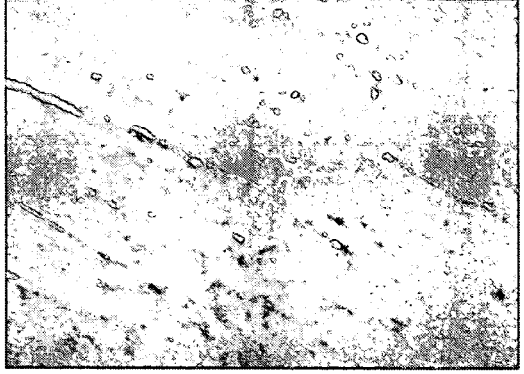
FIGS. 12A-12E show therapeutic effects of CT90-BikDD breast cancer targeting gene therapy in an exemplary orthotopic mouse model.
Figure 12A:
Figure 12A:
Figure 12A:
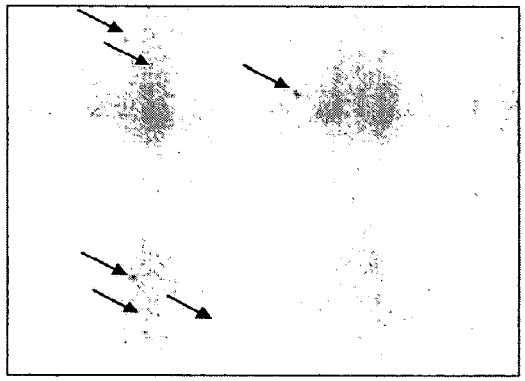
Figure 12B:
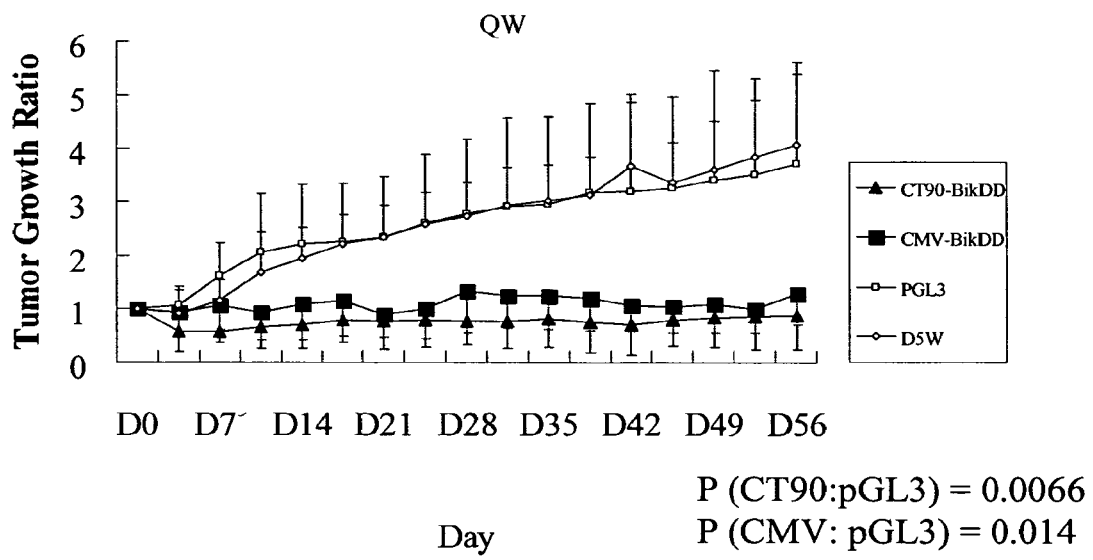
Figure 12C:
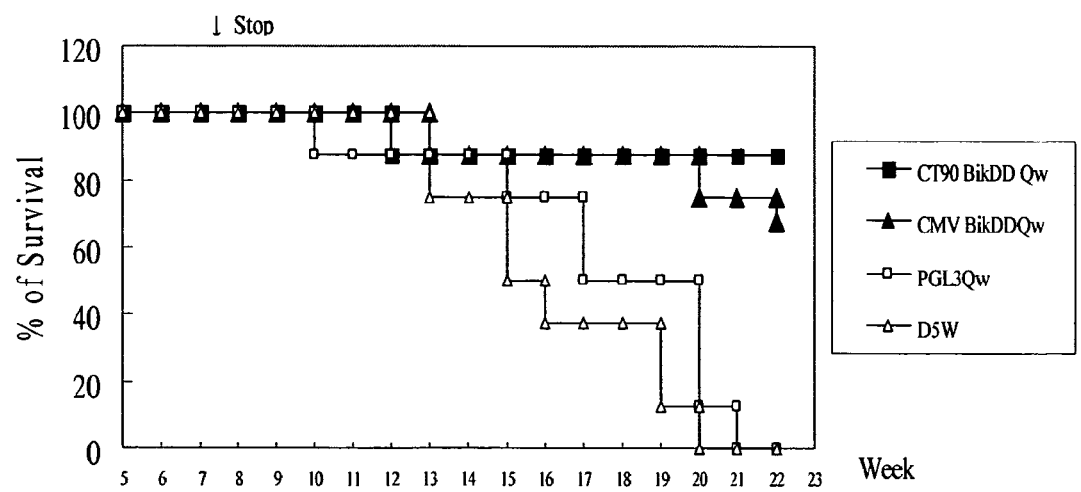
Figure 12D:
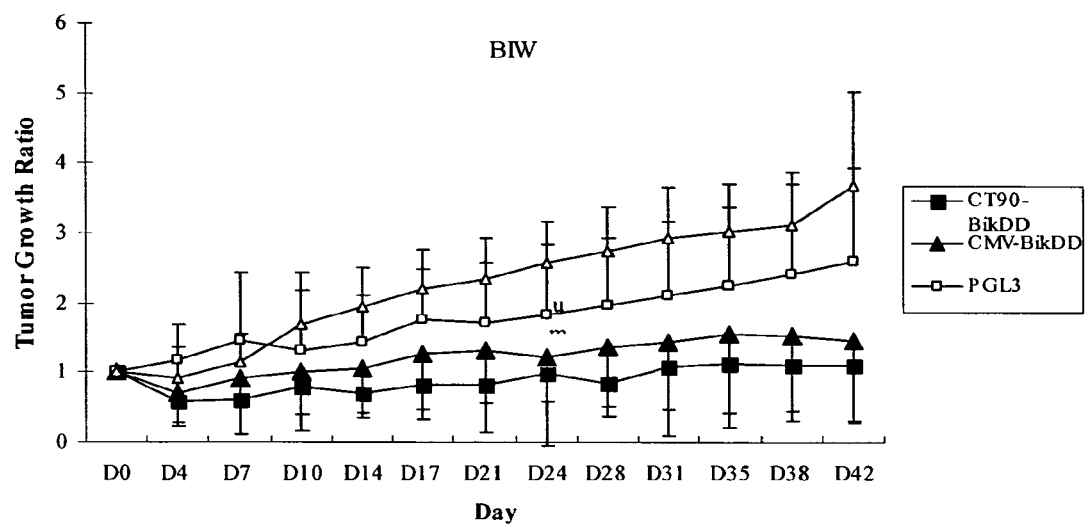
Figure 12E:
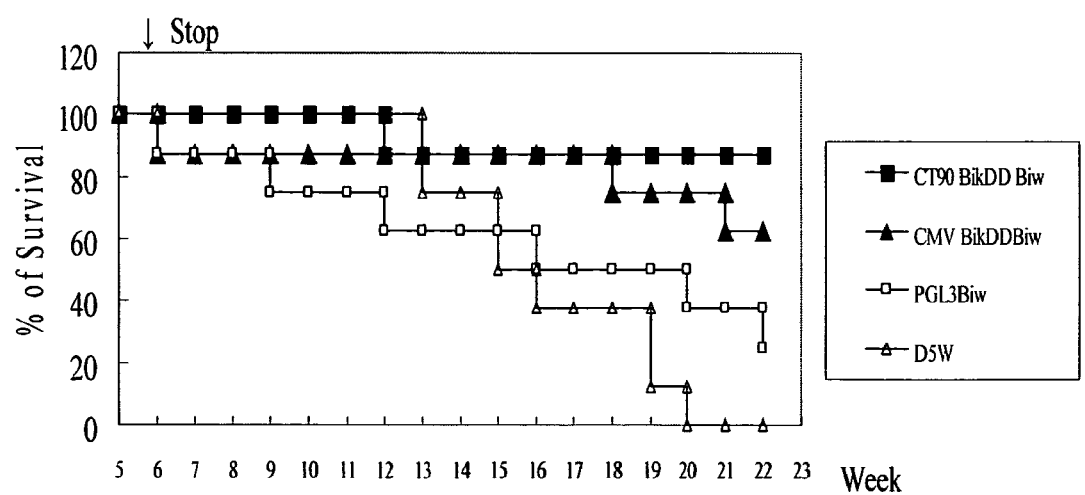

Therapeutic effects of CT90-BikDD breast cancer construct were also demonstrated in an orthotopic mouse model wherein liposome-complexed CT90-BikDD targets breast cancer cells (FIG. 12A). Liposome-complexed CT90-BikDD or CMV-BikDD constructs were administered into mice carrying MDA-MB-468 breast cancer xenograft. The mice were sacrificed 72 hours after injection, and tumor and major organs were removed and fixed. In situ hybridization was performed on the tissue sections to detect BikDD mRNA expression. The results of tumor and heart were shown. The arrows indicate positive cells. In FIGS. 12B and 12D, tumor size record during gene therapy treatment is demonstrated. Mice carrying MDA-MB-231 breast cancer xenograft received treatment of 15-µg liposome complexed CT90-BikDD, CMV-BikDD, empty vector pGL3, or 5% dextrose in water through i.v. injection. Each treatment group had ten mice. The mice were treated once a week (QW, FIG. 12B) or twice a week (BIW, FIG. 12D) for eight weeks, and the tumor size was measured and recorded twice a week. The p values from T-test for CT90 vs. pGL3 (P(CT90:pGL3)) and CMV vs. pGL3 (P(CMV:pGL3)) were shown. FIGS. 12C and 12E show survival record of mice in QW (FIG. 12C) or BIW (FIG. 12E) group. The treatment was stopped in the eighth week, and the mice were kept alive until morbid status defined by institute regulation. The survival number each week was recorded.

Figure 13:
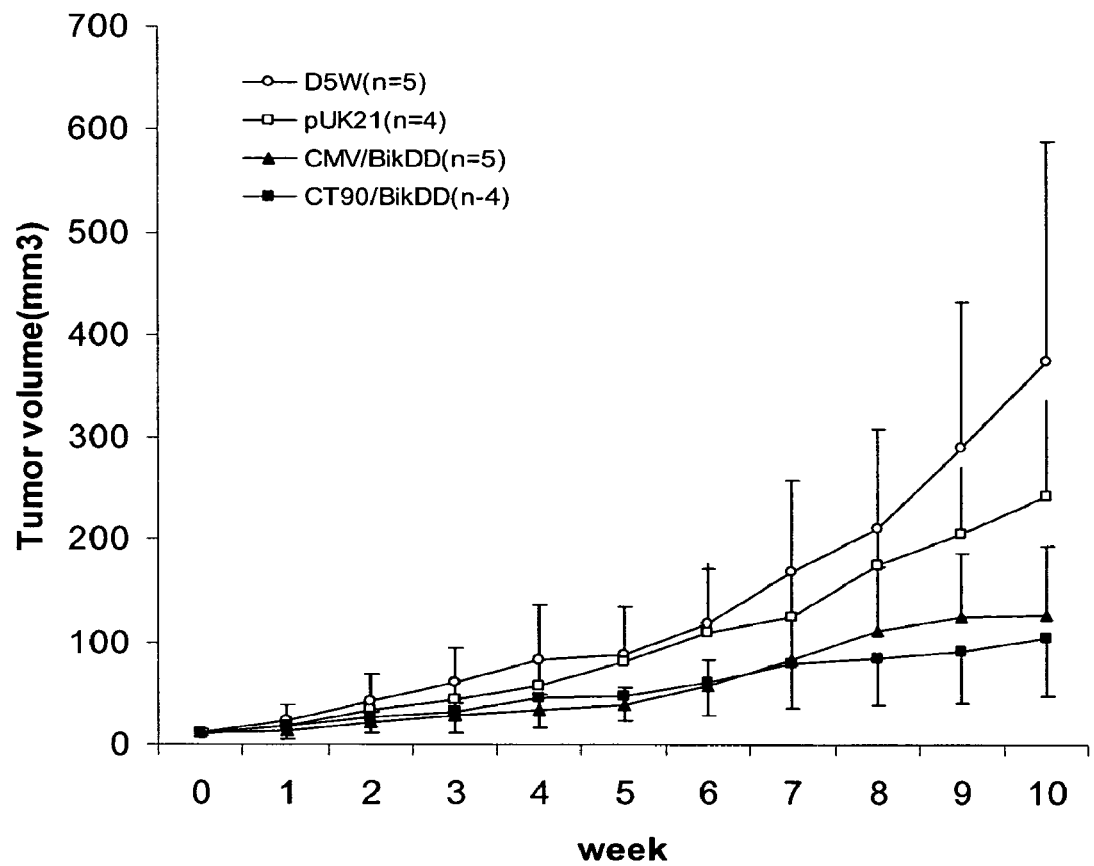
FIG. 13 illustrates gene therapy of Bik-DD in MDA-MB-468 xenograft mice.

Gene therapy of Bik-DD in MDA-MB-468 xenograft mice is illustrated in FIG. 13. Mice carrying MDA-MB-468 breast cancer xenograft received treatment of 15-µg liposome-complexed CT90-BikDD, CMV-BikDD, empty vector pUK21, or 5% dextrose in water through i.v. injection, for example. Each treatment group had ten mice. The mice were treated once a week for eight weeks, and the tumor size was measured and recorded twice a week.

Transferrin Receptor Breast Cancer-Specific Expression

The present inventors also demonstrate in U.S. Provisional Patent Application 60/559,111, entitled "Cancer-Specific Promoters" by Mien-Chie Hung, Yan Li, Yong Wen, Chi-Ping Day, Kun-Ming Rau, Xiaoming Xie, Zheng Li, filed simultaneously herewith and incorporated by reference herein, that at least part of the transferrin receptor (TR) promoter, such as that comprising SEQ ID NO:27 (CTR116), possesses breast cancer specificity, and in combination with a CMV promoter enhancer (SEQ ID NO:25), for example, it can regulate expression of mutant Bik for effective breast cancer-specific expression. The full CTR116 control sequence (SEQ ID NO:38) comprises SEQ ID NO:25 operatively linked to SEQ ID NO:27.

In further embodiments of the present invention, the respective CT90 and CTR116 elements are also narrowed further to identify even smaller segments within that retain breast cancer-specific expression activity. For example, deletion constructs may be made of these respective regions, and their tissue specificity is tested to identify the smaller segments that maintain the ability to direct expression in breast cancer tissue.

Pancreatic Cancer-Specific Expression of Mutant Bik

The present inventors may utilize pancreatic cancer-specific promoter sequences to control expression of a polynucleotide encoding a mutant Bik polypeptide. One particular but exemplary pancreatic cancer-specific promoter is described herein and is presented in further detail in U.S. Provisional Patent Application 60/559,111, entitled "Cancer-Specific Promoters" by Mien-Chie Hung, Yan Li, Yong Wen, Chi-Ping Day, Kun-Ming Rau, Xiaoming Xie, Zheng Li, filed simultaneously herewith and incorporated by reference herein in its entirety.

Generally, an operably linked minimal CCKAR promoter and TSTA construct (wherein the TSTA sequence may be Gal4VP2, for example) operably linked to WPRE regulates expression of mutant Bik polypeptide. The two-step transcriptional amplification (activation) (TSTA) sequence preferably augments the transcriptional activity of cellular promoters (Iyer, Wu et al. 2001; Zhang, Adams et al. 2002) such as CCKAR. In this system, the first step involves the tissue-specific expression of the fusion protein of GAL4-VP16 or GAL4-VP2, for example. In the second step, GAL4-VP16 or GAL4-VP2 in turn, drives target gene expression under the control of GAL4 response elements in a minimal promoter. Also, the TSTA sequence may comprise the G5E4T sequence (SEQ ID NO:36), as an example, which comprises five 17-bp GAL4 binding sites positioned 23 bases from the TAT box of the E4 gene of adenovirus (Carey et al., 1990). Post-transcriptional regulation of mutant Bik may also be employed in pancreatic cancer utilizing a regulatory element such as WPRE. Thus, a composite construct for pancreatic cancer-specific expression is comprised in SEQ ID NO:34, which includes at least CCKAR (SEQ ID NO:28), GAL4-VP2 (SEQ ID NO:30 or SEQ ID NO:33), G5E4T (SEQ ID NO:36), and WPRE (SEQ ID NO:29).

In particular embodiments of the present invention, constructs are similarly generated comprising these or similar pancreatic-specific promoters operatively linked to a polynucleotide encoding a mutant Bik, followed by introduction into a mammal in need of pancreatic cancer therapy treatment based on analogous methods described herein. Parameters are easily optimized by those of skill in the art, such as delivery mode, concentration of composition, and so forth.

In further embodiments of the present invention, the pancreatic cancer-specific element(s) is narrowed further to identify one or more smaller segments within that retain pancreatic cancer-specific expression activity. For example, deletion constructs may be made of these respective regions, and their tissue specificity is characterized to identify the smaller segments that maintain the ability to direct expression in pancreatic cancer tissue.

Prostate Cancer-Specific Expression of Mutant Bik

A prostate cancer-specific promoter sequence is employed to control expression of a polynucleotide encoding a mutant Bik polypeptide. One particular but exemplary pancreatic cancer-specific promoter is described herein and is presented in further detail in U.S. Provisional Patent Application 60/559,111, entitled "Cancer-Specific Promoters" by Mien-Chie Hung, Yan Li, Yong Wen, Chi-Ping Day, Kun-Ming Rau, Xiaoming Xie, Zheng Li, filed simultaneously herewith and incorporated by reference herein in its entirety. In specific embodiments, a prostate cancer-specific promoter that regulates expression of mutant Bik in both androgen-dependent and androgen-independent manners is utilized.

Generally, the hTERT promoter is operatively linked to a two-step transcriptional amplification (activation) (TSTA) sequence that preferably augments the transcriptional activity of cellular promoters (Iyer, Wu et al. 2001; Zhang, Adams et al. 2002). GAL4-VP16 fusion protein or GAL4-VP2 fusion protein may be utilized. In this system, the first step involves the tissue-specific expression of the GAL4-VP16 (or GAL4-VP2, for example) fusion protein. In the second step, GAL4-VP16, in turn, drives target gene expression under the control of GAL4 response elements in a minimal promoter. The use of TSTA preferably leads to amplified levels of the transgene expression. The promoter further comprises ARR2 prostate-cancer specific element (SEQ ID NO:31). The post-transcriptional regulatory element of the woodchuck hepatitis virus (WPRE), which involves modification of RNA polyadenylation, RNA export, and/or RNA translation (Donello, Loeb et al., 1998), is operatively linked to pARR2-hTERT-TSTA to produce pARR2.hTERTp-TSTA-mutant Bik-WPRE. In a specific aspect of the invention, the promoter is effective in both androgen-dependent and androgen-independent prostate cancers. Thus, a composite construct for prostate cancer-specific expression is comprised in SEQ ID NO:35, which includes at least ARR2 (SEQ ID NO:31), hTERT (SEQ ID NO:32), GAL4-VP2 (SEQ ID NO:30 or SEQ ID NO:33), G5E4T (SEQ ID NO:36), and WPRE (SEQ ID NO:29).

In further embodiments of the present invention, the respective prostate cancer-specific element(s) is narrowed further to identify one or more even smaller segments within that retain prostate cancer-specific expression activity. For example, deletion constructs may be made of these respective regions, and their tissue specificity is tested to identify the one or more smaller segments that maintain the ability to direct expression in prostate cancer tissue.

Example 12

Clinical Trials

This example is concerned with the development of human treatment protocols using the Bik mutant protein, peptide, or polypeptide or a nucleic acid encoding the Bik mutant protein, peptide, or polypeptides, alone or in combination with other anti-cancer drugs. The Bik mutant protein, peptide, or polypeptide or a nucleic acid encoding the Bik mutant protein, peptide, or polypeptides, and anti-cancer drug treatment will be of use in the clinical treatment of various cancers involving, for example, Akt activation in which transformed or cancerous cells play a role. Such treatment will be particularly useful tools in anti-tumor therapy, for example, in treating patients with ovarian, breast, prostate, pancreatic, brain, colon, and lung cancers that are resistant to conventional chemotherapeutic regimens.

The various elements of conducting a clinical trial, including patient treatment and monitoring, will be known to those of skill in the art in light of the present disclosure. The following information is being presented as a general guideline for use in establishing the Bik mutant protein, peptide, or polypeptide or a nucleic acid encoding the Bik mutant protein, peptide, or polypeptides, in clinical trials.

Patients with advanced, metastatic breast, epithelial ovarian carcinoma, pancreatic, colon, or other cancers chosen for clinical study will typically be at high risk for developing the cancer, will have been treated previously for the cancer which is presently in remission, or will have failed to respond to at least one course of conventional therapy. In an exemplary clinical protocol, patients may undergo placement of a Tenckhoff catheter, or other suitable device, in the pleural or peritoneal cavity and undergo serial sampling of pleural/peritoneal effusion. Typically, one will wish to determine the absence of known loculation of the pleural or peritoneal cavity, creatinine levels that are below 2 mg/dl, and bilirubin levels that are below 2 mg/dl. The patient should exhibit a normal coagulation profile.

In regard to the Bik mutant protein, peptide, or polypeptide or a nucleic acid encoding the Bik mutant protein, peptide, or polypeptides, and other anti-cancer drug administration, a Tenckhoff catheter, or alternative device may be placed in the pleural cavity or in the peritoneal cavity, unless such a device is already in place from prior surgery. A sample of pleural or peritoneal fluid can be obtained, so that baseline cellularity, cytology, LDH, and appropriate markers in the fluid (CEA, CA15-3, CA 125, PSA, p38 (phosphorylated and un-phosphorylated forms), Akt (phosphorylated and un-phosphorylated forms) and in the cells (Bik mutant proteins, peptides or polypeptides or nucleic acids encoding the same) may be assessed and recorded.

In the same procedure, the Bik mutant protein, peptide, or polypeptide or a nucleic acid encoding the Bik mutant protein, peptide, or polypeptides, may be administered alone or in combination with the other anti-cancer drug. The administration may be in the pleural/peritoneal cavity, directly into the tumor, or in a systemic manner. The starting dose may be 0.5 mg/kg body weight. Three patients may be treated at each dose level in the absence of grade>3 toxicity. Dose escalation may be done by 100% increments (0.5 mg, 1 mg, 2 mg, 4 mg) until drug related grade 2 toxicity is detected. Thereafter dose escalation may proceed by 25% increments. The administered dose may be fractionated equally into two infusions, separated by six hours if the combined endotoxin levels determined for the lot of the Bik protein, peptide, or polypeptide or a nucleic acid encoding the Bik mutant protein, peptide, or polypeptides, and the lot of anti-cancer drug exceed 5 EU/kg for any given patient.

The Bik mutant protein, peptide, or polypeptide or a nucleic acid encoding the Bik mutant protein, peptide, or polypeptides, and/or the other anti-cancer drug combination, may be administered over a short infusion time or at a steady rate of infusion over a 7 to 21 day period. The Bik mutant protein, peptide, or polypeptide or a nucleic acid encoding the Bik mutant protein, peptide, or polypeptides, infusion may be administered alone or in combination with the anti-cancer drug and/or emodin like tyrosine kinase inhibitor. The infusion given at any dose level will be dependent upon the toxicity achieved after each. Hence, if Grade II toxicity was reached after any single infusion, or at a particular period of time for a steady rate infusion, further doses should be withheld or the steady rate infusion stopped unless toxicity improved. Increasing doses of the Bik mutant protein, peptide, or polypeptide or a nucleic acid encoding the mutant protein, peptide, or polypeptides, in combination with an anti-cancer drug will be administered to groups of patients until approximately 60% of patients show unacceptable Grade III or IV toxicity in any category. Doses that are $\frac{2}{3}$ of this value could be defined as the safe dose.

Physical examination, tumor measurements, and laboratory tests should, of course, be performed before treatment and at intervals of about 3-4 weeks later. Laboratory studies should include CBC, differential and platelet count, urinalysis, SMA-12-100 (liver and renal function tests), coagulation profile, and any other appropriate chemistry studies to determine the extent of disease, or determine the cause of existing symptoms. Also appropriate biological markers in serum should be monitored e.g. CEA, CA 15-3, p38 (phosphorylated and non-phopshorylated forms) and Akt (phosphorylated and non-phosphorylated forms), p185, etc.

To monitor disease course and evaluate the anti-tumor responses, it is contemplated that the patients should be examined for appropriate tumor markers every 4 weeks, if initially abnormal, with twice weekly CBC, differential and platelet count for the 4 weeks; then, if no myelosuppression has been observed, weekly. If any patient has prolonged myelosuppression, a bone marrow examination is advised to rule out the possibility of tumor invasion of the marrow as the cause of pancytopenia. Coagulation profile shall be obtained every 4 weeks. An SMA-12-100 shall be performed weekly. Pleural/peritoneal effusion may be sampled 72 hours after the first dose, weekly thereafter for the first two courses, then every 4 weeks until progression or off study. Cellularity, cytology, LDH, and appropriate markers in the fluid (CEA, CA15-3, CA 125, ki67 and Tunel assay to measure apoptosis, Akt) and in the cells (Akt) may be assessed. When measurable disease is present, tumor measurements are to be recorded every 4 weeks. Appropriate radiological studies should be repeated every 8 weeks to evaluate tumor response. Spirometry and DLCO may be repeated 4 and 8 weeks after initiation of therapy and at the time study participation ends. An urinalysis may be performed every 4 weeks.

Clinical responses may be defined by acceptable measure. For example, a complete response may be defined by the disappearance of all measurable disease for at least a month. Whereas a partial response may be defined by a 50% or greater reduction of the sum of the products of perpendicular diameters of all evaluable tumor nodules or at least 1 month with no tumor sites showing enlargement. Similarly, a mixed response may be defined by a reduction of the product of perpendicular diameters of all measurable lesions by 50% or greater with progression in one or more sites.

REFERENCES

All patents and publications mentioned in the specification are indicative of the level of those skilled in the art to which the invention pertains. All patents and publications are herein incorporated by reference in their entirety to the same extent as if each individual publication was specifically and individually indicated to be incorporated by reference.

Patents

U.S. Pat. No. 4,683,202
U.S. Pat. No. 4,797,368
U.S. Pat. No. 4,879,236
U.S. Pat. No. 5,139,941

U.S. Pat. No. 5,220,007
U.S. Pat. No. 5,284,760
U.S. Pat. No. 5,354,670
U.S. Pat. No. 5,366,878
U.S. Pat. No. 5,389,514
U.S. Pat. No. 5,635,377
U.S. Pat. No. 5,641,484
U.S. Pat. No. 5,670,488
U.S. Pat. No. 5,789,166
U.S. Pat. No. 5,798,208
U.S. Pat. No. 5,830,650
U.S. Pat. No. 5,871,986
U.S. Pat. No. 5,925,565
U.S. Pat. No. 5,928,906
U.S. Pat. No. 5,935,819

PUBLICATIONS

Anderson, L. M., Krotz, S., Weitzman, S. A., and Thimmapaya, B. (2000). Breast cancer-specific expression of the *Candida albicans* cytosine deaminase gene using a transcriptional targeting approach. Cancer Gene Ther 7, 845-852.

Bartke, T., Siegmund, D., Peters, N., Reichwein, M., Henkler, F., Scheurich, P., and Wajant, H. p53 upregulates cFLIP, inhibits transcription of NF-kappaB-regulated genes and induces caspase-8-independent cell death in DLD-1 cells, Oncogene. 20: 571-80, 2001.

Boyd, J. M., Gallo, G. J., Elangovan, B., Houghton, A. B., Malstrom, S., Avery, B. J., Ebb, R. G., Subramanian, T., Chittenden, T., Lutz, R. J., and et al. Bik, a novel death-inducing protein shares a distinct sequence motif with Bcl-2 family proteins and interacts with viral and cellular survival-promoting proteins, Oncogene. 11: 1921-8, 1995.

Carey, M., Leatherwood, J., and Ptashne, M. A potent GAL4 derivative activates transcription at a distance in vitro, Science 247:710-712, 1990.

Daniel, P. T., Pun, K. T., Ritschel, S., Sturm, I., Holler, J., Dorken, B., and Brown, R. Expression of the death gene Bik/Nbk promotes sensitivity to drug-induced apoptosis in corticosteroid-resistant T-cell lymphoma and prevents tumor growth in severe combined immunodeficient mice, Blood. 94: 1100-7, 1999.

Desagher, S., Osen-Sand, A., Montessuit, S., Magnenat, E., Vilbois, F., Hochmann, A., Journot, L., Antonsson, B., and Martinou, J. C. Phosphorylation of bid by casein kinases I and II regulates its cleavage by caspase 8, Mol. Cell. 8: 601-11, 2001.

Emami, K. H. and Carey, M. (1992) A synergistic increase in potency of a multimerized VP16 transcriptional activation domain. EMBO J. 11:5005-5012.

Han, J., Sabbatini, P., and White, E. Induction of apoptosis by human Nbk/Bik, a BH3-containing protein that interacts with E1B 19K, Mol Cell Biol. 16: 5857-64, 1996.

Iyer, M., Wu, L., Carey, M., Wang, Y., Smallwood, A., and Gambhir, S. S. (2001). Two-step transcriptional amplification as a method for imaging reporter gene expression using weak promoters. Proc. Natl. Acad. Sci. 98:14595-14600.

Katabi, M. M., Chan, H. L., Karp, S. E., and Batist, G. (1999). Hexokinase type II: a novel tumor-specific promoter for gene-targeted therapy differentially expressed and regulated in human cancer cells. Hum Gene Ther 10, 155-164.

Klumpp, S. and Krieglstein, J. Serine/threonine protein phosphatases in apoptosis, Curr Opin Pharmacol. 2: 458-62, 2002.

Lu, H., Zhang, Y., Roberts, D. D., Osborne, C. K., and Templeton, N. S. (2002). Enhanced gene expression in breast cancer cells in vitro and tumors in vivo. Mol Ther 6, 783-792.

Maeda, T., J, O. W., Matsubara, H., Asano, T., Ochiai, T., Sakiyama, S., and Tagawa, M. (2001). A minimum c-erbB-2 promoter-mediated expression of herpes simplex virus thymidine kinase gene confers selective cytotoxicity of human breast cancer cells to ganciclovir. Cancer Gene Ther 8, 890-896.

Mathai, J. P., Germain, M., Marcellus, R. C., and Shore, G. C. Induction and endoplasmic reticulum location of BIK/NBK in response to apoptotic signaling by E1A and p53, Oncogene. 21: 2534-44, 2002.

Nettelbeck, D. M., Jerome, V. and Muller, R. (2000) Gene therapy: designer promoters for tumour targeting. Trends Genet. 16:174-181.

Panaretakis, T., Pokrovskaja, K., Shoshan, M. C., and Grander, D. Activation of Bak, Bax, and BH3-only Proteins in the Apoptotic Response to Doxorubicin, J Biol. Chem. 277: 44317-26, 2002.

Puthalakath, H. and Strasser, A. Keeping killers on a tight leash: transcriptional and post-translational control of the pro-apoptotic activity of BH3-only proteins, Cell Death Differ. 9: 505-12, 2002.

Qiao, J., Doubrovin, M., Sauter, B. V., Huang, Y., Guo, Z. S., Balatoni, J., Akhurst, T., Blasberg, R. G., Tjuvajev, J. G., Chen, S. H., and Woo, S. L. (2002). Tumor-specific transcriptional targeting of suicide gene therapy. Gene Ther 9, 168-175.

Sadowski I, Ma J, Triezenberg S, Ptashne M. GAL4-VP16 is an unusually potent transcriptional activator. Nature. 1988 Oct. 6; 335(6190):563-4.

Sato, M., Johnson, M., Zhang, L., Zhang, B., Le, K., Gambhir, S. S., Carey, M., Wu, L. (2003) Optimization of adenoviral vectors to direct highly amplified prostate-specific expression for imaging and gene therapy. Mol. Ther. 8(5): 726-737.

Takeuchi M, Shichinohe T, Senmaru N, Miyamoto M, Fujita H, Takimoto M, Kondo S, Katoh H, Kuzumaki N. The dominant negative H-ras mutant, N116Y, suppresses growth of metastatic human pancreatic cancer cells in the liver of nude mice. Gene Ther. 2000 March; 7(6):518-26.

Theodorakis, P., Lomonosova, E., and Chinnadurai, G. Critical requirement of BAX for manifestation of apoptosis induced by multiple stimuli in human epithelial cancer cells, Cancer Res. 62: 3373-6, 2002.

Verma, S., Zhao, L., and Chinnadurai, G. Phosphorylation of the Pro-Apoptotic Protein BIK: Mapping of Phosphorylation sites and Effect on Apoptosis, J Biol. Chem. 17: 17, 2000.

Wang, H. G., Pathan, N., Ethell, I. M., Krajewski, S., Yamaguchi, Y., Shibasaki, F., McKeon, F., Bobo, T., Franke, T. F., and Reed, J. C. Ca2+-induced apoptosis through calcineurin dephosphorylation of BAD, Science. 284: 339-43, 1999.

Wang X P, Yazawa K, Yang J, Kohn D, Fisher W E, Brunicardi F C. Specific gene expression and therapy for pancreatic cancer using the cytosine deaminase gene directed by the rat insulin promoter. J Gastrointest Surg. 2004 January; 8(1):98-108.

Wesseling J G, Yamamoto M, Adachi Y, Bosma P J, van Wijland M, Blackwell J L, Li H, Reynolds P N, Dmitriev I, Vickers S M, Huibregtse K, Curiel D T. Midkine and cyclooxygenase-2 promoters are promising for adenoviral vector gene delivery of pancreatic carcinoma. Cancer Gene Ther. 2001 December; 8(12):990-6.

Zhang, L., Adams, J. Y., Billick, E., Ilagan, R., Iyer, M., Le, K., Smallwood, A., Gambhir, S. S., Carey, M., Wu, L. (2002) Molecular engineering of a two-step transcription amplification (TSTA) system for transgene delivery in prostate cancer. Mol. Ther. 5(3): 223-232.

Zou, Y., Peng, H., Zhou, B., Wen, Y., Wang, S. C., Tsai, E. M., and Hung, M. C. Systemic tumor suppression by the proapoptotic gene bik, Cancer Res. 62: 8-12, 2002.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

We claim:

1. A polynucleotide construct comprising a nucleic acid sequence encoding a Bik polypeptide having anti-tumor activity, anti-cell proliferation activity, and/or pro-apoptotic activity, wherein the construct further comprises a tissue-specific control sequence operatively linked to the sequence encoding the Bik polypeptide and wherein the Bik polypeptide comprises a Thr33 to Asp33 substitution, a Ser35 to Asp35 substitution, or both.

2. The polynucleotide of claim 1, further defined as being comprised in a liposome.

3. The polynucleotide of claim 1, wherein the polynucleotide encodes a protein comprising the amino acid sequence of SEQ ID NO:7, SEQ ID NO:8, or SEQ ID NO:9.

4. The polynucleotide of claim 1, wherein the polynucleotide encodes SEQ ID NO:3 comprising a Thr33 to Asp33 substitution, a Ser35 to Asp35 substitution, or both.

* * * * *